(12) United States Patent
Nakanishi

(10) Patent No.: US 9,570,691 B2
(45) Date of Patent: Feb. 14, 2017

(54) AMBIENT TEMPERATURE LIQUID-FORM ORGANIC MATERIALS AND USE THEREOF

(75) Inventor: Takashi Nakanishi, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 786 days.

(21) Appl. No.: 13/878,013

(22) PCT Filed: Oct. 7, 2011

(86) PCT No.: PCT/JP2011/073240
§ 371 (c)(1),
(2), (4) Date: May 10, 2013

(87) PCT Pub. No.: WO2012/046849
PCT Pub. Date: Apr. 12, 2012

(65) Prior Publication Data
US 2013/0234125 A1    Sep. 12, 2013

(30) Foreign Application Priority Data

Oct. 7, 2010 (JP) ................................. 2010-227174

(51) Int. Cl.

| | | |
|---|---|---|
| *C09B 23/00* | (2006.01) | |
| *C09B 23/14* | (2006.01) | |
| *H01L 51/00* | (2006.01) | |
| *B82Y 10/00* | (2011.01) | |
| *C07D 487/22* | (2006.01) | |
| *C09B 1/00* | (2006.01) | |
| *C09B 23/01* | (2006.01) | |
| *C09B 23/08* | (2006.01) | |
| *C09B 29/01* | (2006.01) | |
| *C09B 29/12* | (2006.01) | |
| *C09B 29/34* | (2006.01) | |
| *C09B 47/00* | (2006.01) | |
| *C09B 57/00* | (2006.01) | |
| *C09B 69/10* | (2006.01) | |
| *C09D 11/50* | (2014.01) | |
| *H01G 9/20* | (2006.01) | |
| *H01L 51/42* | (2006.01) | |
| *H01L 51/50* | (2006.01) | |

(52) U.S. Cl.
CPC .......... *H01L 51/0077* (2013.01); *B82Y 10/00* (2013.01); *C07D 487/22* (2013.01); *C09B 1/00* (2013.01); *C09B 23/0066* (2013.01); *C09B 23/086* (2013.01); *C09B 23/148* (2013.01); *C09B 29/0003* (2013.01); *C09B 29/12* (2013.01); *C09B 29/34* (2013.01); *C09B 47/00* (2013.01); *C09B 57/00* (2013.01); *C09B 69/101* (2013.01); *C09B 69/106* (2013.01); *C09B 69/109* (2013.01); *C09D 11/50* (2013.01); *H01L 51/005* (2013.01); *H01L 51/0047* (2013.01); *H01L 51/0052* (2013.01); *H01G 9/2063* (2013.01); *H01L 51/42* (2013.01); *H01L 51/50* (2013.01); *H01L 2224/45144* (2013.01); *H01L 2224/48091* (2013.01); *H01L 2224/48247* (2013.01); *H01L 2224/48257* (2013.01); *Y02E 10/549* (2013.01)

(58) Field of Classification Search
None
See application file for complete search history.

(56) References Cited

FOREIGN PATENT DOCUMENTS

| | | |
|---|---|---|
| JP | 2008-255291 | 10/2008 |
| JP | 2009-139214 | 6/2009 |
| WO | 03/008475 | 1/2003 |
| WO | 2007/081490 | 7/2007 |

OTHER PUBLICATIONS

Wu et al, Chem. Mater. 2011, 23, 4618-4624.*
International Search Report issued Dec. 27, 2011 in International (PCT) Application No. PCT/JP2011/073240.
A. Chowdhury et al., "Transient Characteristics of Light-Emitting Devices based on Langmuir-Blodgett Films of a Porphyrin Derivative", Synthetic Metals, vol. 122, No. 2, pp. 243-247, 2001.
M. J. Plater et al., "Metallated Porphyrins Containing Lead(II), Copper(II) or Zinc(II)", Tetrahedron, vol. 58, No. 12, pp. 2415-2422, 2002.
C. Yang et al., "Polyphenylenes and Poly(phenyleneethynylene)s with 9,10-Anthrylene Subunits", Macromolecular Chemistry and Physics, vol. 207, No. 13, pp. 1107-1115, 2006.
S. Kim et al., "Tris[oligo(1,4-phenylenevinylene)]methylium Dyes", European Journal of Organic Chemistry, vol. 12, pp. 1976-1983, 2009.
W. Pisula et al., "Relation Between Supramolecular Order and Charge Carrier Mobility of Branched Alkyl Hexa-peri-Hexabenzocoronenes", Chemistry of Materials, vol. 18, No. 16, pp. 3634-3640, 2006.

* cited by examiner

*Primary Examiner* — Alicia L Otton
(74) *Attorney, Agent, or Firm* — Wenderoth, Lind & Ponack, L.L.P.

(57) ABSTRACT

An organic material consisting of a π-conjugated molecule which is in a liquid form at ambient temperature and use thereof are provided. The ambient temperature liquid-form organic material according to the present invention consists of a π-conjugated molecule having 2 or more side chains, the 2 or more side chains are same or different side chains selected from the group consisting of a branched alkyl chain, an alkyl chain having a polymerization site at a terminal, an oligosiloxane chain, a fluorocarbon chain, an oligoethylene glycol chain and derivatives thereof, and each of the 2 or more side chains is bound directly or via a substituent to the π-conjugated molecule.

8 Claims, 74 Drawing Sheets

610

AMBIENT TEMPERATURE LIQUID-FORM ORGANIC MATERIALS AND USE THEREOF

TECHNICAL FIELD

The present invention relates to an organic material which is in a liquid form at ambient temperature and use thereof.

BACKGROUND ART

Recently, porphyrin derivatives which are in a liquid form at ambient temperature were developed (see, for example, Patent Literature 1). Patent Literature 1 discloses porphyrin derivatives represented by the formula shown below:

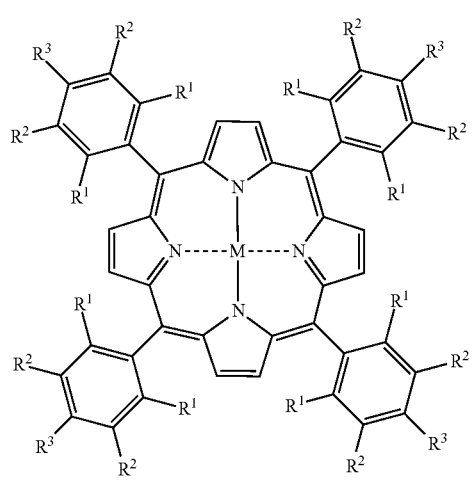

[C.1]

According to Patent Literature 1, in the formula shown above, M denotes an atom or a compound capable of forming a covalent bond or a coordinate bond with 2H (hydrogen atoms) or tetraphenyl porphyrin. Each of $R^1$, $R^2$ and $R^3$ denotes, independently from each other, a hydrogen atom, or an alkoxy group having 7 to 15 carbon atoms represented by $OR^4$, $R^4$ is a substituted or unsubstituted alkyl group having 7 to 15 carbon atoms, identical meanings are applicable within all $R^1$s, all $R^2$s and all $R^3$s, respectively. Each of $R^2$ and $R^3$ is an alkoxy group having 7 to 15 carbon atoms represented by $OR^4$ and $R^1$ is a hydrogen atom, or each of $R^1$ and $R^3$ is an alkoxy group having 7 to 15 carbon atoms represented by $OR^4$ and $R^2$ is a hydrogen atom, or each of $R^1$ and $R^2$ is an alkoxy group having 7 to 15 carbon atoms represented by $OR^4$ and $R^3$ is a hydrogen atom, or, each of $R^1$, $R^2$ and $R^3$ is an alkoxy group having 7 to 15 carbon atoms represented by $OR^4$.

Since the porphyrin derivatives in Patent Literature 1 have 3 to 5 alkoxy groups having a certain number of the carbon atoms in a certain position on the phenyl ring, they have a liquid property at room temperature (25° C. to 40° C.) without containing any solvent and also have a high thermostability.

SUMMARY OF THE INVENTION

Problems to be Solved by the Invention

Nevertheless, the phenyl ring of the porphyrin derivatives of Patent Literature 1 requires a large number of alkoxy groups, which limits to keep high density of the porphyrin. As a result, the properties inherent in the porphyrin may not sufficiently be exerted. It is also advantageous that ambient temperature liquid-form organic materials other than the porphyrin can be obtained.

Accordingly, an object of the invention is to provide an organic material which is in the form of a liquid at ambient temperature and consists of a π-conjugated molecule as well as use thereof.

Means for Solving the Problems

The ambient temperature liquid-form organic material according to the present invention consists of a π-conjugated molecule having 2 or more side chains, and the 2 or more side chains are same or different side chains selected from the group consisting of a branched alkyl chain, an alkyl chain having a polymerization site at a terminal, an oligosiloxane chain, a fluorocarbon chain, an oligoethylene glycol chain and derivatives thereof, and each of the 2 or more side chains are linked to the π-conjugated molecule directly or via a substituent, thereby accomplishing the object.

The branched alkyl chain is bound directly to the π-conjugated molecule, and the branched alkyl chain is represented by the formula shown below:

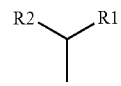

[C.2]

wherein the R1 is a substituted or unsubstituted alkyl group consisting of 4 or more carbon atoms, the R2 is a substituted or unsubstituted alkyl group consisting of 6 or more carbon atoms, the number of the carbon atoms of the R1 may be smaller than the number of the carbon atoms of the R2.

The branched alkyl chain is bound to the π-conjugated molecule via a substituent, and the branched alkyl chain is represented by the formula shown below:

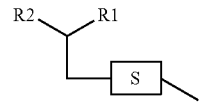

[C.3]

wherein the R1 is a substituted or unsubstituted alkyl group consisting of 4 or more carbon atoms, the R2 is a substituted or unsubstituted alkyl group consisting of 6 or more carbon atoms, the number of the carbon atoms of the R1 may be smaller than the number of the carbon atoms of the R2, and the S may be a substituent.

The substituent may be at least one selected from the group consisting of phenyl, benzyl, methylene, amido, ester, ether, thioether and urea.

The combination of the R1 and R2 can be selected from the group consisting of the formulae:

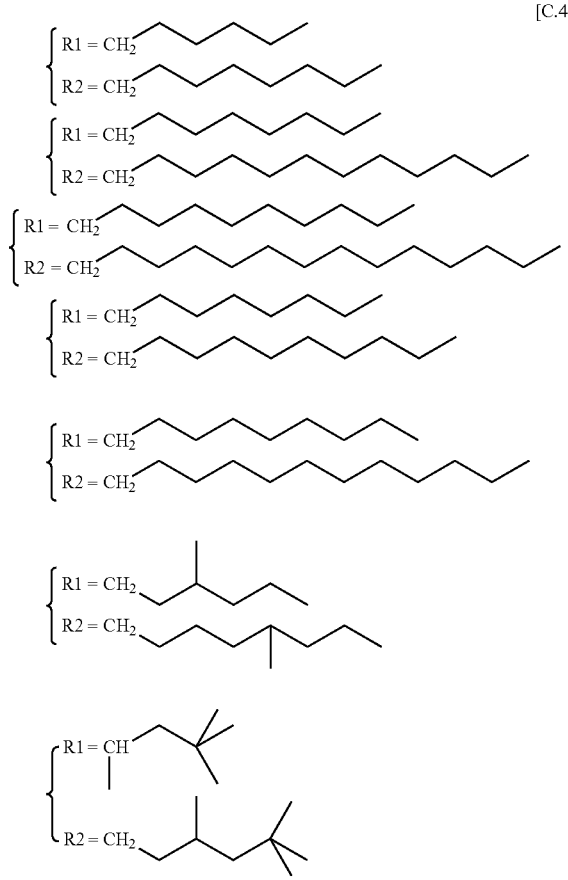

[C.4]

The alkyl group having a polymerization site at the terminal can be selected from the group consisting of a terminal olefin $\{-(CH_2)_n-CH=CH_2\}$, a terminal dienyl $\{-(CH_2)_n-CH=CH-CH=CH_2\}$, a terminal acrylic acid ester $\{-(CH_2)_n-OC(=O)CH=CH_2\}$, a terminal methacrylic acid ester $\{-(CH_2)_n-OC(=O)C(CH_3)=CH_2\}$ and a terminal epoxy group $\{-(CH_2)_n-CHOCH_2\}$ (wherein each n satisfies $6 \leq n \leq 14$).

The oligosiloxane chain can be selected from the group consisting of $-(Si-R_a(R_b))_n-H$, $-(Si-R_a(R_b))_n-SiH_3$ and $-(Si-R_a(R_b))_n-Si(CH_3)_3$ (wherein n satisfies $2 \leq n \leq 10$, and the combination of $R_a$ and $R_b$ is selected from the group consisting of $\{R_a=H, R_b=H\}$, $\{R_a=H, R_b=CH_3\}$ and $\{R_a=CH_3, R_b=CH_3\}$).

The fluorocarbon chain may be $-(CF_2)_nCF_3$, (wherein n satisfies $5 \leq n \leq 9$).

The oligoethylene glycol chain may be $-(O-CH_2-CH_2)_n-OH$ or $-(O-CH_2-CH_2)_n-OCH_3$ (n satisfies $2 \leq n \leq 10$).

The π-conjugated molecule may exhibit absorption in ultraviolet or visible wavelength region.

The π-conjugated molecule can be selected from the group consisting of porphyrin, phthalocyanine, oligo(p-)phenylene vinylene, oligo(p-)phenylene ethylene, perylene, perylenebisimido, fluorene, anthracene, tetracene, pentacene, pyrene, azobenzene, stilbene, diallylethene, oligophenylene, oligothiophene, oxal-based pigment and derivatives thereof.

The π-conjugated molecule is porphyrin and may be represented by any of the followings:

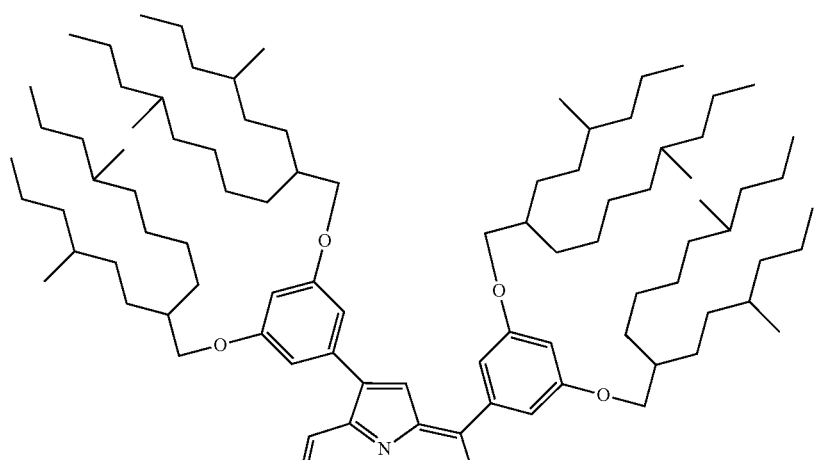

[C.5]

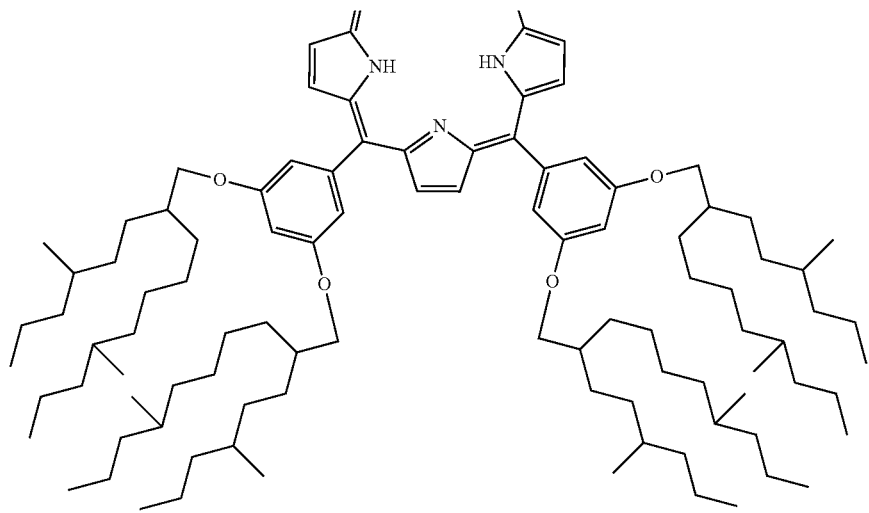
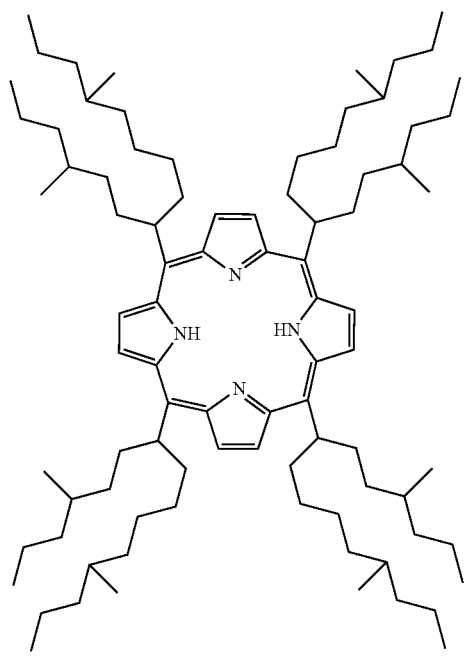

The π-conjugated molecule is anthracene and may be represented by any of the followings:
[C.6]
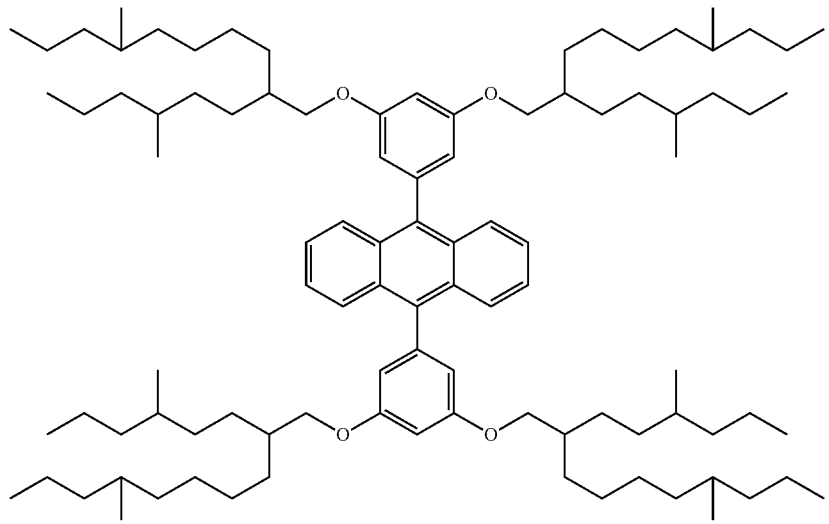
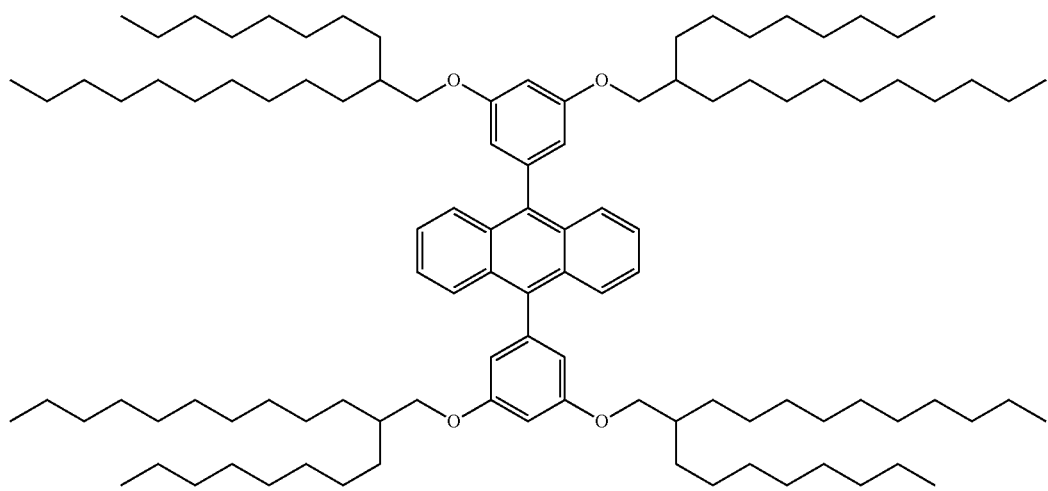
The π-conjugated molecule is oligo(p-)phenylene vinylene and may be represented by any of the followings:
[C.7]
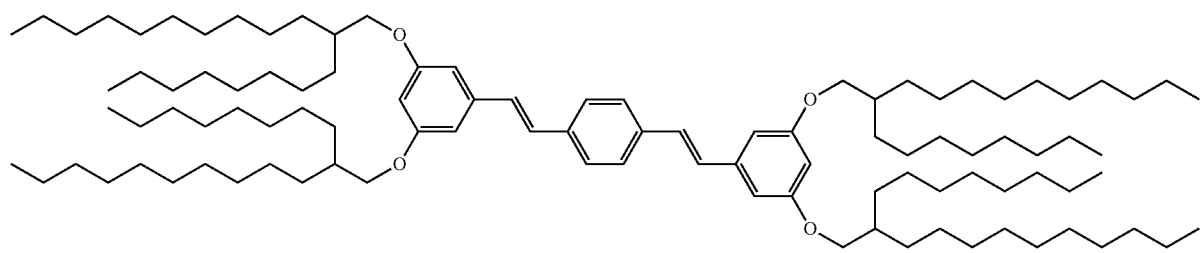

-continued
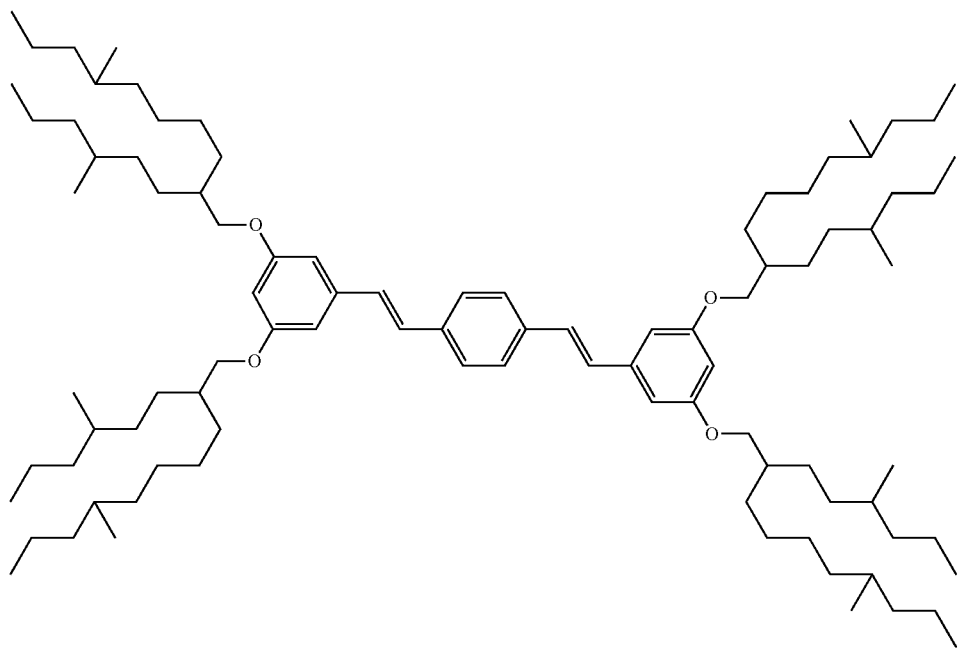
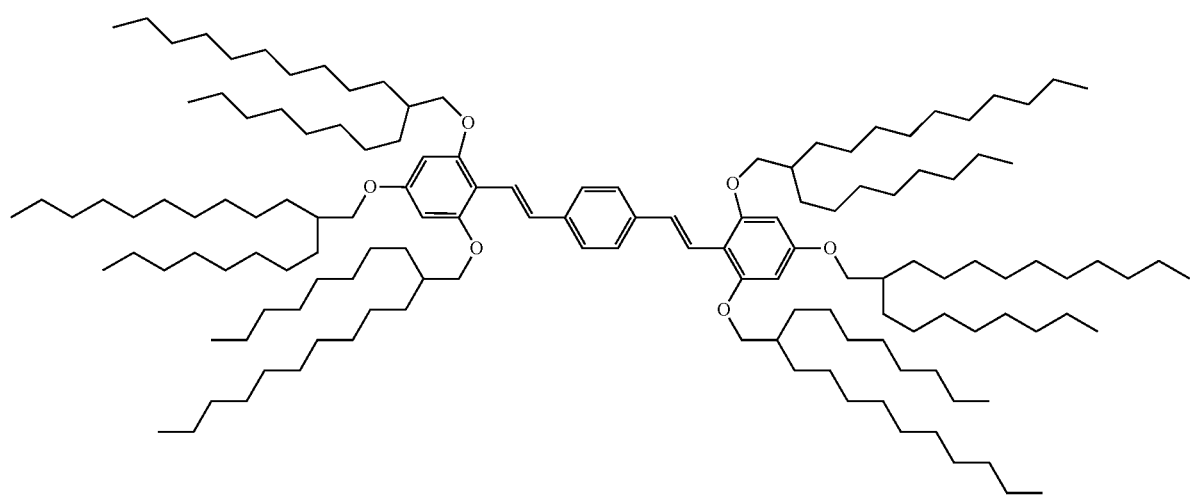
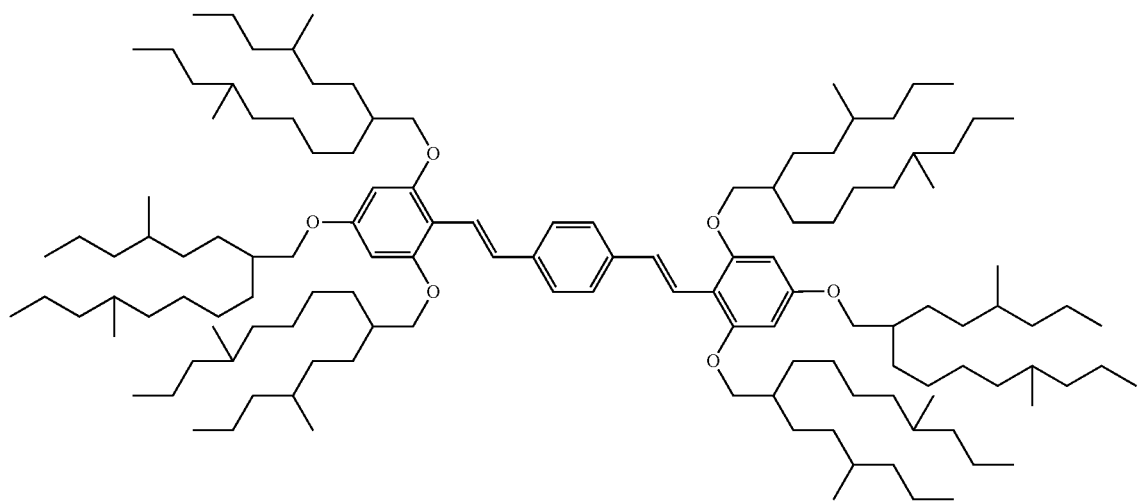 [SMILES: CCCC(C)CCCCC(CCC(C)CCC)COc1cc(OCC(CCCCC(C)CCC)CCC(C)CCC)c(/C=C/c2ccc(/C=C/c3c(OCC(CCCCC(C)CCC)CCC(C)CCC)cc(OCC(CCCCC(C)CCC)CCC(C)CCC)cc3OCC(CCCCC(C)CCC)CCC(C)CCC)cc2)c(OCC(CCCCC(C)CCC)CCC(C)CCC)c1]

The π-conjugated molecule is fluorene and may be represented by the following:

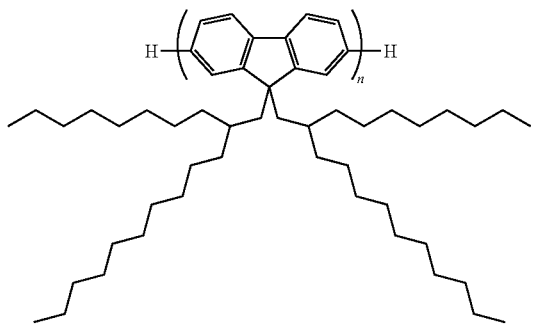

[C.8]

(wherein n is an integer of 1 or more).

The π-conjugated molecule is stilbene and may be represented by the following:

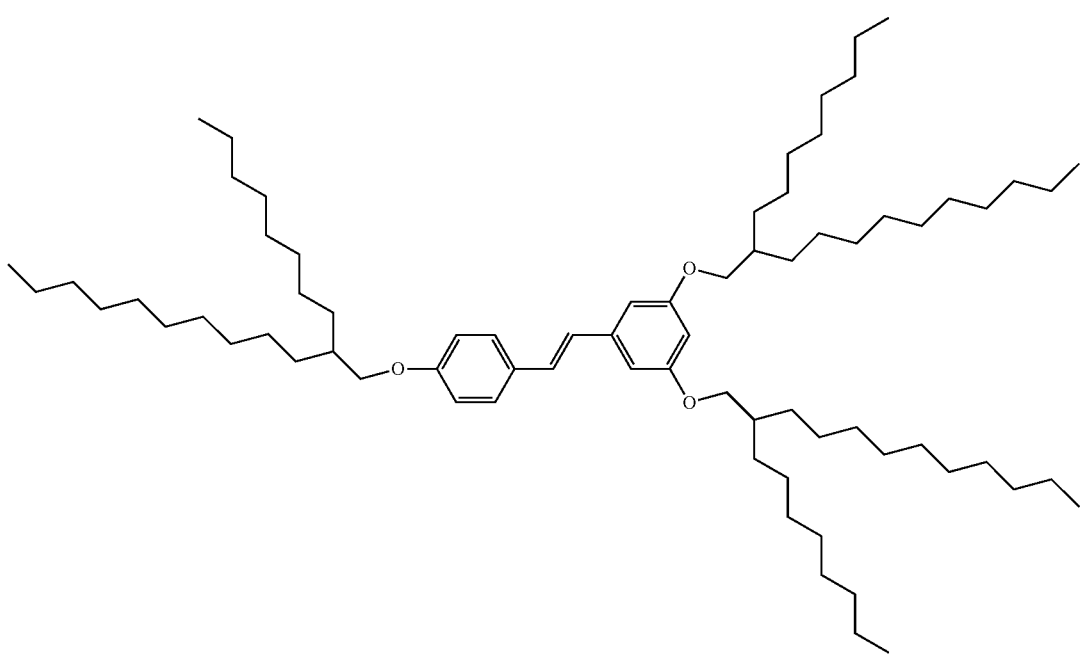

[C.9]

The π-conjugated molecule is azobenzene and may be represented by the following:

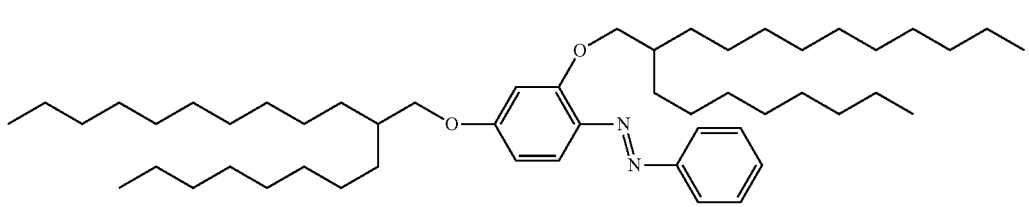

[C.10]

The π-conjugated molecule may have a coordinated metal.

The π-conjugated molecule is selected from the group consisting of 2,2'-bipyridine, 1,10-phenanthroline, terpyridine, cyclic π-conjugated molecule and derivatives thereof and the metal can be selected from the group consisting of Mg, Al, Si, Ti, V, Cr, Mn, Fe, Co, Ni, Cu, Zn, Ga, Ge, Ru, Rh, Pd, Sn, Os, Pt, Au, Ce, Nd, Eu and Lu.

The π-conjugated molecule may be a ferrocene derivative.

The luminescent material according to the present invention consists of the ambient temperature liquid-form organic material, thereby accomplishing the object.

The ink material according to the present invention consists of the ambient temperature liquid-form organic material, thereby accomplishing the object.

The photovoltaic device according to the present invention comprises, a transparent electrode, a photovoltaic part and a counter electrode, and the photovoltaic part comprises the ambient temperature liquid-form organic material, thereby accomplishing the object.

The photovoltaic part comprises an electron donor and an electron acceptor, and the solvent for the electron donor and electron acceptor can be the ambient temperature liquid-form organic material.

The photovoltaic part comprises an electron donor and an electron acceptor, and the electron donor is the ambient temperature liquid-form organic material, and the electron acceptor can be an ambient temperature liquid-form fullerene.

Advantage of the Invention

The ambient temperature liquid-form organic material according to the present invention consists of a π-conjugated molecule having 2 or more side chains directly or via a substituent. By selecting certain side chains and by allowing the π-conjugated molecule to possess 2 or more selected side chains, the π-π interaction between the π-conjugated molecules is inhibited. As a result, the π-conjugated molecules undergo isolation and dispersion, because of which an ambient temperature liquid-form organic material can be provided.

The ambient temperature liquid-form organic material according to the present invention maintains, at ambient temperature, its liquid form while exhibiting the properties inherent in the π-conjugated molecule (luminescent property, color chromogenic property, optoelectronic property, conductivity). The ambient temperature organic material according to the present invention can be used, without need of a solvent, a matrix material and the like, as a π-conjugated molecule's luminescent property-based luminescent material, a π-conjugated molecule's pigment (chromogenicity)-based ink material, a π-conjugated molecule's conductivity-based conductive material. Also when the ambient temperature liquid-form organic material according to the present invention is employed as a photovoltaic part of a photovoltaic device utilizing an optoelectronic property, a thinner and compacter product can be obtained since no solvent for the photovoltaic device is needed.

MODE FOR CARRYING OUT THE INVENTION

Embodiment 1

Figure 1:
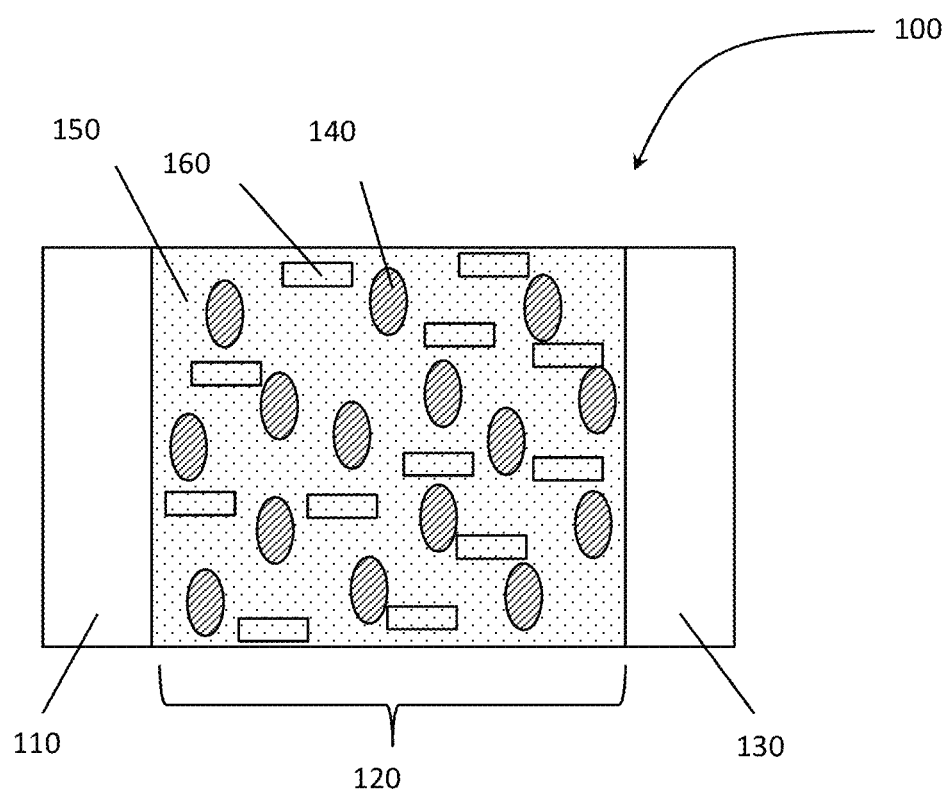
FIG. 1 shows a schematic view of a photovoltaic device employing an ambient temperature liquid-form organic material of the present invention.

In Embodiment 1, the ambient temperature liquid-form organic material according to the present invention is described.

The ambient temperature liquid-form organic material according to the present invention consists of a π-conjugated molecule having 2 or more side chains. Herein the 2 or more side chains are selected from the group consisting of a branched alkyl chain, an alkyl chain having a polymerization site at a terminal, an oligosiloxane chain, a fluorocarbon chain, an oligoethylene glycol chain and derivatives thereof. The 2 or more side chains may be same or different. Furthermore, each of the 2 or more side chains is bound directly or via a substituent to the π-conjugated molecule.

We discovered that, by selecting the certain side chains as the side chains and by allowing the π-conjugated molecule to possess the 2 or more selected side chains, the π-π interaction between the π-conjugated molecules is inhibited. As a result, we were successful in allowing any π-conjugated molecule to be in the form of a liquid at ambient temperature.

As used herein, an "ambient temperature" means a temperature within the range from 10° C. to 40° C. Also as used herein, a "liquid form" means an isotropic fluid exhibiting a flowability in the absence of solvents, matrix materials and the like. As used herein, a "π-conjugated molecule" means a molecule having a π-conjugated electron system, i.e., having a wide range of the molecular wave function on a plane.

When the certain side chain is a branched alkyl chain and is bound directly to the π-conjugated molecule, the branched alkyl chain is represented preferably by the formula shown below:

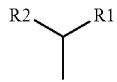

[C.11]

wherein, R1 is a substituted or unsubstituted alkyl group having at least 4 carbon atoms. R2 is a substituted or unsubstituted alkyl group having at least 6 carbon atoms. The number of the carbon atoms in R1 is smaller than that in R2.

By using such a branched alkyl chain, the π-π interaction between the π-conjugated molecules is inhibited efficiently in spite of an extremely small number of the side chains when compared with the alkoxy group of Patent Literature 1. As a result, the π-conjugated molecules undergo isolation and dispersion at a higher density when compared with Patent Literature 1, because of which an ambient temperature liquid-form organic material can be provided at a high concentration. Such an ambient temperature liquid-form organic material is preferable since it allows the properties inherent in the π-conjugated molecule to be exerted easily.

When the certain side chain is a branched alkyl chain and is bound via a substituent to the π-conjugated molecule, the branched alkyl chain is represented preferably by the formula shown below:

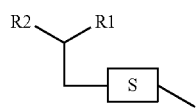

[C.12]

wherein, R1 and R2 are same to the R1 and R2. S represents a substituent.

Also in this case, the branched alkyl chain serves to inhibit the π-π interaction between the π-conjugated molecules efficiently while the possession of the substituent S by the branched alkyl chain allows the R1 and R2 substituents to be introduced readily into the π-conjugated molecule, thereby allowing the π-conjugated molecule to be liquefied surly at ambient temperature. Also as a result of the introduction of the substituent, the room temperature liquid-form organic material of the invention is imparted with an enhanced freedom of material design.

The substituent S is at least one selected from the group consisting of phenyl, benzyl, methylene, amido, ester, ether, thioether and urea. Any such a substituent S allows the substituents R1 and R2 to be introduced into the π-conjugated molecule without changing the characteristics of the π-conjugated molecule.

When the π-conjugated molecule of the ambient temperature liquid-form organic material according to the present invention has a branched alkyl chain via a substituent, the branched alkyl chain has at least one substituent S, and when the branched alkyl chain has two or more substituent Ss, then the second substituent S may be shared.

The combination of R1 and R2 in the branched alkyl chain is selected preferably from the group consisting of the formulae shown below. As a result, the π-π interaction between the π-conjugated molecules can surely be inhibited, thereby ensuring the ambient temperature liquefaction. The substituted R1 and R2 allow their one or more hydrogen atoms for example in the alkyl group to be substituted with a halogen atom, an aromatic group, a cyano group, a nitro group, an alkoxy group and the like, which are not limitative as far as the advantage of the invention can be realized.

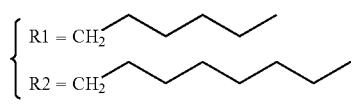

[C.13]

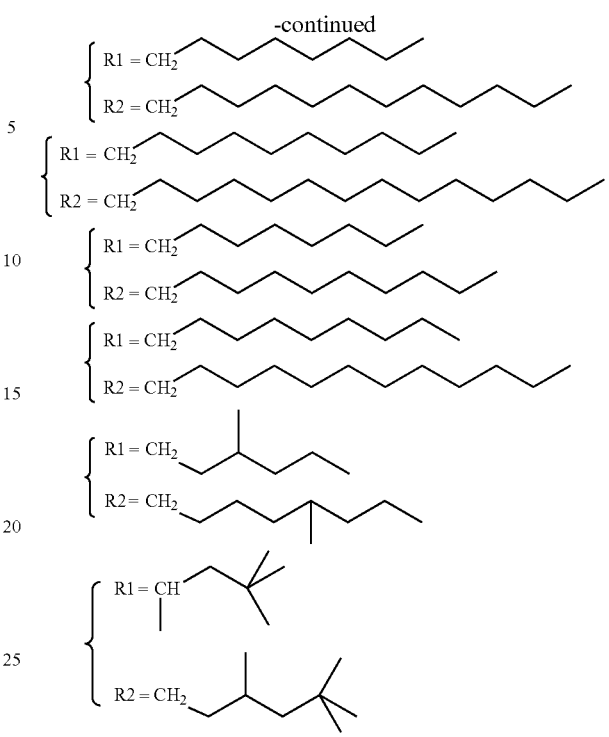

-continued

When the ambient temperature liquid-form organic material of the present invention has 2 or more side chains both of which are the branched alkyl chains bound directly or via a substituent S, the combination of R1 and R2 in each of the 2 or more branched alkyl chains is not limited to be identical with each other, although the combination of R1 and R2 in each of the 2 or more branched alkyl chains is preferably identical in view of convenience of the manufacture.

On the basis of the selection of the combination of R1 and R2 as well as the combination of R1 and R2 with the π-conjugated molecule described below, the viscosity and the melting point can be controlled.

When the certain side chain is an alkyl chain having a polymerization site at a terminal, the alkyl chain having a polymerization site at a terminal is selected preferably from the group consisting of a terminal olefin {—$(CH_2)_n$—CH=$CH_2$}, a terminal dienyl {—$(CH_2)_n$—CH=CH—CH=$CH_2$}, a terminal acrylic acid ester {—$(CH_2)_n$—OC(=O)CH=$CH_2$}, a terminal methacrylic acid ester {—$(CH_2)_n$—OC(=O)C($CH_3$)=$CH_2$} and a terminal epoxy group {—$(CH_2)_n$—CHOCH$_2$} (wherein each n satisfies 6≤n≤14). A number of the carbon atoms of 6 or more allows the π-π interaction of the π-conjugated molecule to be inhibited efficiently, while a number of the carbon atoms exceeding 15 allows the effect of the van der Waals interaction between the alkyl chains to be increased thereby raising the melting point and reducing the density of the π-conjugated molecule. Also since the polymerization site is possessed, an ultraviolet irradiation can be utilized, optionally in combination with an appropriate polymer or monomer, for example, to enable the immobilization of the ambient temperature liquid-form organic material, thus allowing the ambient temperature liquefied organic material to be provided with a further function. The terminal epoxy group is one in which —CHOCH$_2$ forms a 3-membered ring.

When the certain side chain is an oligosiloxane chain, the oligosiloxane chain is selected preferably from the group consisting of —(Si—$R_a$($R_b$))$_n$—H, —(Si—$R_a$($R_b$))$_n$—SiH$_3$ and —(Si—R$_a$(R$_b$))$_n$—Si(CH$_3$)$_3$ (wherein n satisfies 2≤n≤10, and the combination of R$_a$ and R$_b$ is selected from the group consisting of {R$_a$=H, R$_b$=H}, {R$_a$=H, Rb=CH$_3$} and {Ra=CH$_3$, Rb=CH$_3$}). An oligomer degree (n) of 2 or more allows the π-π interaction of the π-conjugated molecule to be inhibited efficiently, while n exceeding 11 yields a polysiloxane chain, resulting in a difficulty in keeping a high density of the π-conjugated molecule. Also since the side chain contains an Si—O—Si (siloxane bond), the binding energy is greater than the C—C bond of the alkyl chain, resulting in an excellent heat resistance which prevents oxidation or decomposition. Furthermore, a weather resistance (UV resistance and radiation resistance) is also possessed advantageously.

When the certain side chain is a fluorocarbon chain, the fluorocarbon chain is represented preferably by —(CF$_2$)$_n$CF$_3$ (n satisfies 5≤n≤9). A number of the carbon atoms of 5 or more allows the π-π interaction of the π-conjugated molecule to be inhibited efficiently, while a number of the carbon atoms exceeding 10 leads to the bulkiness and the rigidity of the fluorocarbon chain resulting in a reduced density and an increased melting point of the π-conjugated molecule. A fluorocarbon chain-bearing ambient temperature liquid-form organic material is not mixed for example with an unsubstituted branched alkyl chain-bearing ambient temperature liquid-form organic material. Thus, the ambient temperature liquid-form organic material is allowed to undergo a phase separation, thus providing the ambient temperature liquid-form organic material with a further function.

When the certain side chain is an oligoethylene glycol chain, the oligoethylene oxide chain is preferably —(O—CH$_2$—CH$_2$)$_n$—OH or —(O—CH$_2$—CH$_2$)$_n$—OCH$_3$ (n satisfies 2≤n≤10). A number of the carbon atoms of 2 or more allows the π-π interaction of the π-conjugated molecule to be inhibited efficiently, while a number of the carbon atoms exceeding 11 yields a polyethylene glycol chain, resulting in a difficulty in keeping a high density of the π-conjugated molecule. Since the oligoethylene glycol chain has flexibility, it can reduced the viscosity of the ambient temperature liquid-form organic material. Also since the oligoethylene glycol chain has a hydrophilicity, it can mix the ambient temperature liquid-form organic material with water or polar solvents. Thus, the ambient temperature liquid-form organic material is provided with a hydrophilicity or allowed to undergo a phase separation with a hydrophobic ambient temperature liquid-form organic material, thus providing the ambient temperature liquid-form organic material with further functions.

The 2 or more of side chains possessed by the ambient temperature liquid-form organic material of the present invention may all be the same or different. In order to impart a function corresponding to the side chain to the ambient temperature liquid-form organic material, the side chains can appropriately be selected.

Also when the 2 or more of side chains possessed by the ambient temperature liquid-form organic material of the present invention is an alkyl chain having a polymerization site at a terminal, an oligosiloxane chain, fluorocarbon chain or an oligoethylene glycol chain and also when each of them is bound via a substituent to the π-conjugated molecule, the substituent is at least one selected from the group consisting of phenyl, benzyl, methylene, amido, ester, ether, thioether and urea described above.

The π-conjugated molecule of the ambient temperature liquid-form organic material of the present invention has 2 or more certain side chains as described above. When 2 or more certain side chains are possessed, the π-π interaction between the π-conjugated molecule is surely inhibited, thereby ensuring the achievement of the ambient temperature liquefaction. For example, when the π-conjugated molecule is fluorene, anthracene, azobenzene, stilbene, pyrene and the like, 2 or more branched alkyl chains allow the ambient temperature liquefaction to be accomplished easily. Thus, since the ambient temperature liquefaction can be achieved even with such a reduced number of the side chains, a benefit can be realized in exerting the intrinsic properties in the π-conjugated molecule.

A larger number of the side chains possessed by the π-conjugated molecule of the ambient temperature liquid-form organic material of the present invention results in a more intense inhibition of the π-π interaction between the π-conjugated molecule and a lower orderling between the π-conjugated molecules, thereby lowering the melting point.

While the π-conjugated molecule in the ambient temperature liquid-form organic material of the present invention is not limited particularly, any π-conjugated molecule can be selected appropriately depending on the application.

When a chromogenicity or a luminescence development is intended, a π-conjugated molecule exhibiting absorption in ultraviolet or visible wavelength region can be selected as a π-conjugated molecule. Such a π-conjugated molecule is referred to also as a pigment, and known as a color agent. More specifically, a π-conjugated molecule having a pigment is selected from the group consisting of porphyrin, phthalocyanine, oligo(p-)phenylene vinylene, oligo(p-)phenylene ethylene, perylene, perylenebisimido, fluorene, anthracene, tetracene, pentacene, pyrene, azobenzene, stilbene, diallylethene, oligophenylene, oligothiophene, oxal-based pigment and derivatives thereof. For example, anthracene and derivatives thereof are advantageous when used in a laser medium employing a UV light as an excitation source, since they exhibit absorptions in the ultraviolet region and also exhibit a blue luminescence.

The π-conjugated molecule having a pigment can be selected depending on the color desired (for example, absorption wavelength).

When the π-conjugated molecule is porphyrin among those listed above, then an ambient temperature liquid-form organic material in which the all of the two or more side chains are branched alkyl chains and which fulfills the formula shown below is preferable. The ambient temperature liquid-form organic material represented by the formula shown below is referred to as P1.

[C.14]

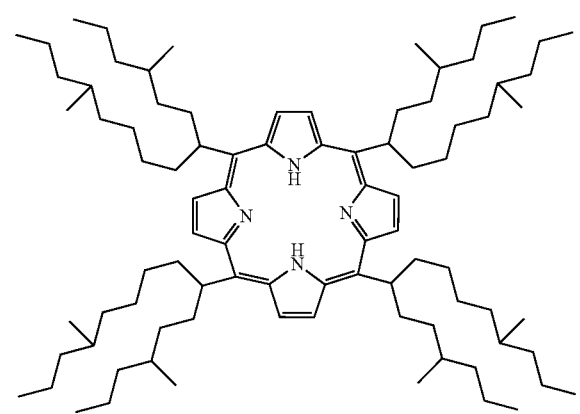

P1 is known to have a glass transition temperature of −13.6° C., and is an ambient temperature liquid-form organic material. In addition, P1 serves as an ink material having a purple color. P1 can serve also as a luminescent material exhibiting a red color luminescence upon a UV light excitation. Furthermore, P1 can constitute a photovoltaic device when used together with an electron acceptor, since it can act as an electron donating solvent or as a liquid-form electron donor itself.

As another ambient temperature liquid-form organic material, the ambient temperature liquid-form organic material wherein the π-conjugated molecule is porphyrin, all of the 2 or more side chains are branched alkyl chains and the substituent S is a combination of phenyl and ether, which is represented by the formula shown below, is exemplified. The ambient temperature liquid-form organic material represented by the formula shown below is referred to as P2.

molecule and on selection of the number or the type of the branched alkyl chains introduced into the selected π-conjugated molecule.

On the other hand, the fluorescence quantum yield of P2 is higher than that of P1. This means that P2 keeps the excitation state for a longer period than P1 does. Thus, it can be understood that the degree of the steric inhibition of the π-π interaction of the π-conjugated molecule can be adjusted while allowing the isolation from the external factors (oxygen and water) thereby sustaining the excitation state over a prolonged period based on selection of the number or the type of the side chains introduced into the π-conjugated molecule.

As a further ambient temperature liquid-form organic material, another ambient temperature liquid-form organic material wherein the π-conjugated molecule is an oligo(p-)phenylene vinylene, all of the 2 or more side chains are

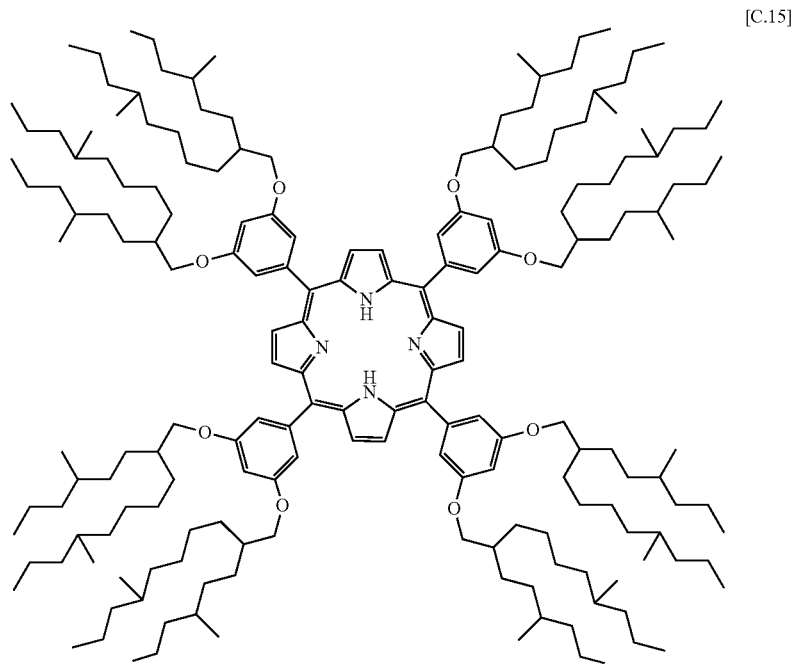 [SMILES: CCCC(C)CCCCC(CCC(C)CCC)COc1cc(OCC(CCCCC(C)CCC)CCC(C)CCC)cc(-c2c3nc(c(-c4cc(OCC(CCCCC(C)CCC)CCC(C)CCC)cc(OCC(CCCCC(C)CCC)CCC(C)CCC)c4)c4ccc([nH]4)c(-c4cc(OCC(CCCCC(C)CCC)CCC(C)CCC)cc(OCC(CCCCC(C)CCC)CCC(C)CCC)c4)c4nc(c(-c5cc(OCC(CCCCC(C)CCC)CCC(C)CCC)cc(OCC(CCCCC(C)CCC)CCC(C)CCC)c5)c5ccc2[nH]5)C=C4)C=C3)c1]

[C.15]

P2 has branched alkyl chains (side chains) each of which has ether as a substituent S, and the branched alkyl chains further share phenyl as a substituent S. Such P2 has the properties similar to those of P1 described above.

The viscosity of P2 is higher than that of P1. The reason lies on the van der Waals interaction between the side chains. Thus, it can be understood that the viscosity of the room temperature liquid-form organic material of the invention can be controlled based on selection of the π-conjugated branched alkyl chains and the substituent S is ether, which satisfies any of the formulae shown below, is preferred. The ambient temperature liquid-form organic material having 4 highly branched alkyl chains (referred to also as hyperbranches) or simply branched alkyl chains (referred to also as a swallowtail) is referred to as OPV1 or OPV2, while the ambient temperature liquid-form organic material having 6 hyperbranch alkyl chains or swallowtail alkyl chains are referred to as OPV3 or OPV4.

[C.16]
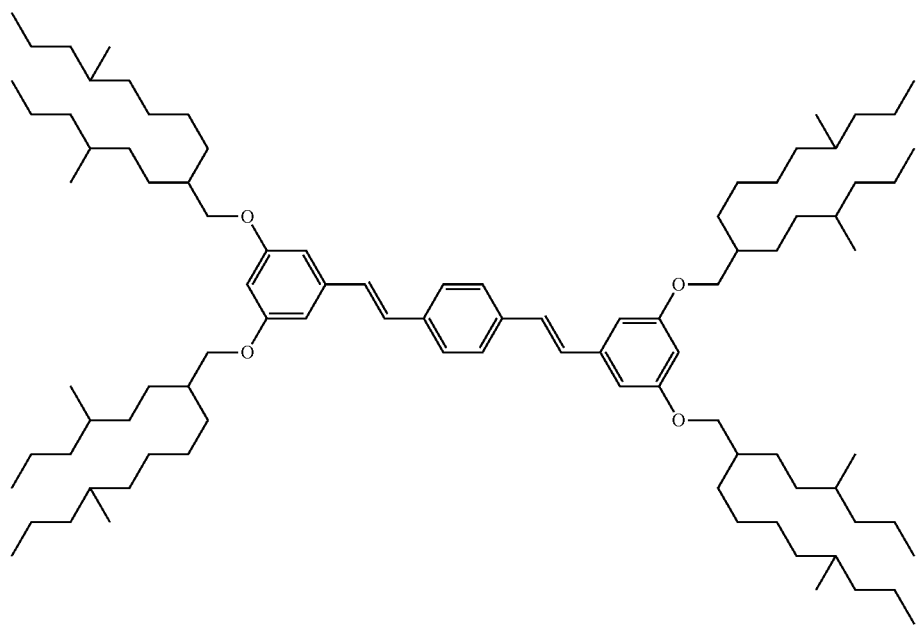
OPV1
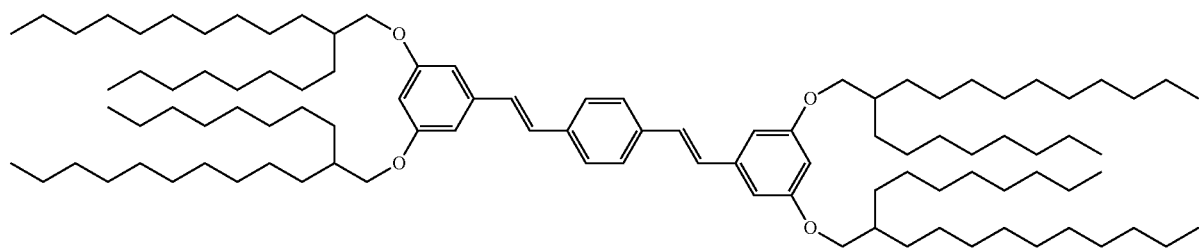
OPV2
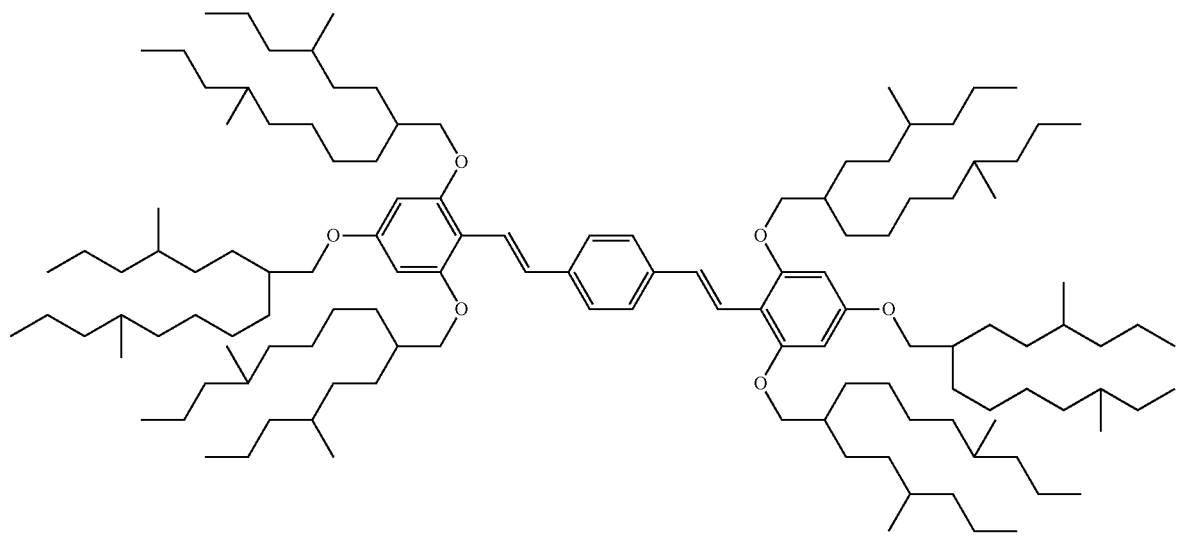
OPV3

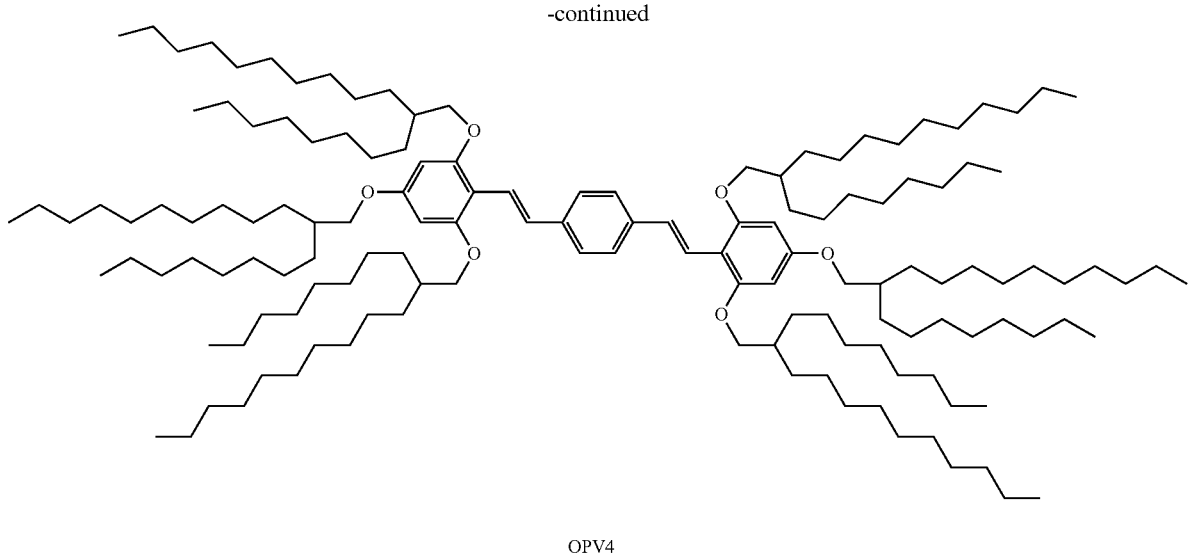

OPV4

Each of OPV1 to OPV4 is a pale yellow color-exhibiting ambient temperature liquid-form organic material. Each of OPV1 to OPV4 can also serve as a luminescent material exhibiting a blue color luminescence upon a UV light excitation and an electronic excitation. Also since each of OPV1 to OPV4 can act, similarly to P1 and P2, as an electron donating solvent or a liquid form electron donor itself, it can constitute a photovoltaic device when used in combination with an electron acceptor.

The viscosity is increased as indicated by OPV4<OPV3=OPV2<OPV1 (thus, OPV4 is the softest and OPV1 is hardest). This means that, resulting from the effective isolation of the π-conjugated molecule (which is OPV here) by the introduced side chains, the viscosity of the ambient temperature liquid-form organic material of the present invention can be controlled based on selection of the π-conjugated molecule and on selection of the number or the type of the branched alkyl chains introduced into the selected π-conjugated molecule.

The fluorescence quantum yield is increased as indicated by OPV1<OPV2<OPV3<OPV4. This also means that, based on selection of the number or the type of the branched alkyl chains introduced into the π-conjugated molecule, the π-π interaction of the π-conjugated molecule can be inhibited more sterically to achieve an isolation from the external factors thereby sustaining the excitation state over a prolonged period.

As a further ambient temperature liquid-form organic material, another ambient temperature liquid-form organic material wherein the π-conjugated molecule is anthracene, all of the 2 or more side chains are branched alkyl chains (hyperbranch or swallowtail) and the substituent S is ether, which satisfies any of the formulae shown below, is preferred. The hyperbranch alkyl chain-bearing ambient temperature liquid-form organic material is referred to as ACN1 and the swallowtail alkyl chain-bearing ambient temperature liquid-form organic material is referred to as ACN2.

[C.17]

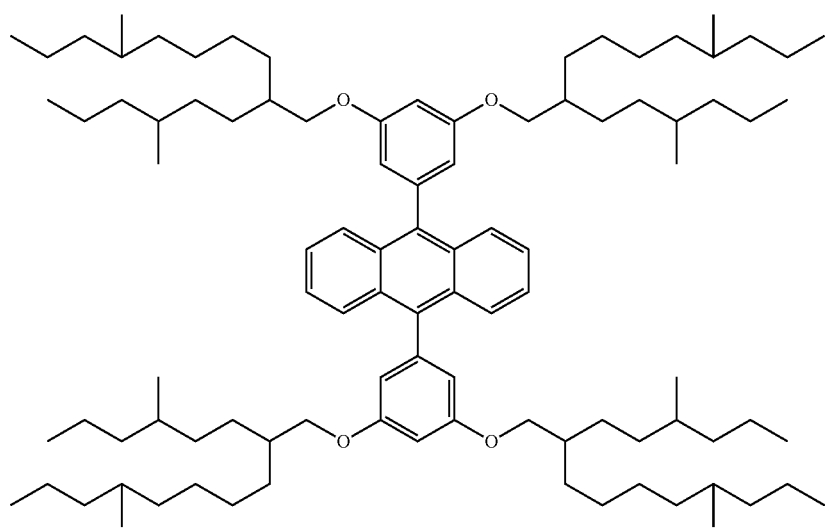

ACN1

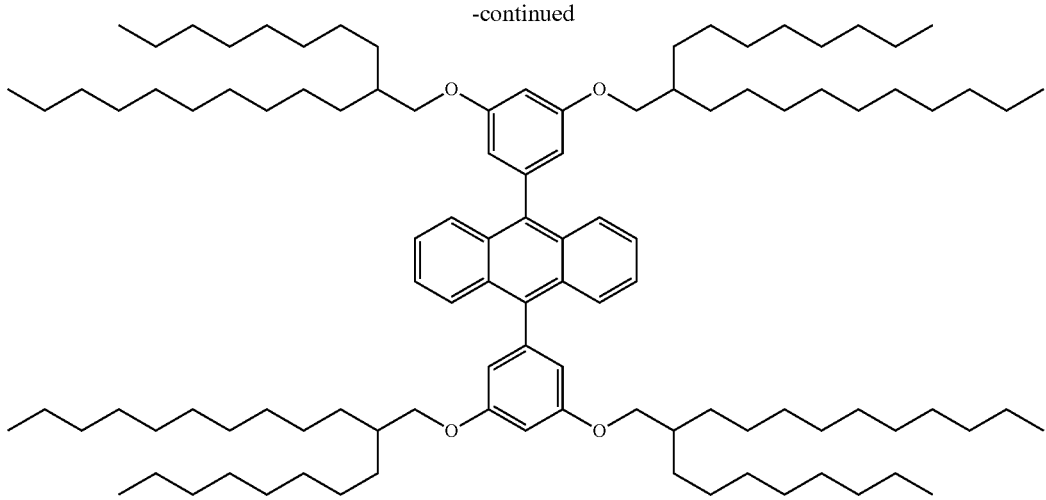

ACN2

Both of ACN1 and ACN2 are pale yellow color-exhibiting ambient temperature liquid-form organic material. ACN1 and ACN2 can be a luminescent material exhibiting a blue color luminescence upon a UV light excitation and an electronic excitation.

As a further ambient temperature liquid-form organic material, another ambient temperature liquid-form organic material wherein the π-conjugated molecule is fluorene and all of the 2 or more side chains are branched alkyl chains (swallowtail), which satisfies the formula shown below, is preferred. In the formula, n is an integer of 1 or more, preferably not more than 5. The ambient temperature liquid-form organic material of n=1 is referred to as FL1 while the ambient temperature liquid-form organic material of n=2 is referred to as FL2 (same applies to all "n"s described below).

[C.18]

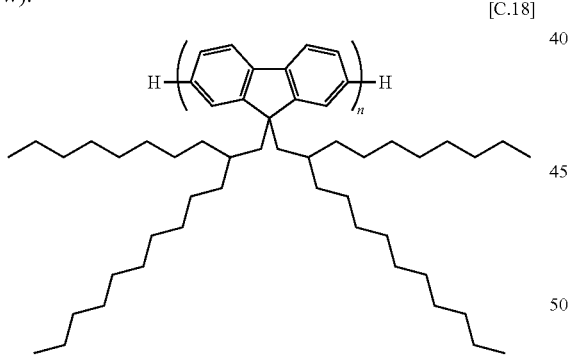

Each of FL2 and FL3 can be a luminescent material exhibiting a blue color luminescence upon a UV light excitation and an electronic excitation. An increased value of "n" leads to a higher viscosity (thus, FL1 is the softest one and an increased value of "n" tends to give an increased hardness). The fluorescence quantum yield tends to be increased as the value of "n" is increased.

As a further ambient temperature liquid-form organic material, another ambient temperature liquid-form organic material wherein the π-conjugated molecule is stilbene, all of the 2 or more side chains are branched alkyl chains (swallowtail) and the substituent S is ether, which satisfies the formula shown below, is preferred. The 3 branched alkyl chain-bearing ambient temperature liquid-form organic material is referred to as STLB.

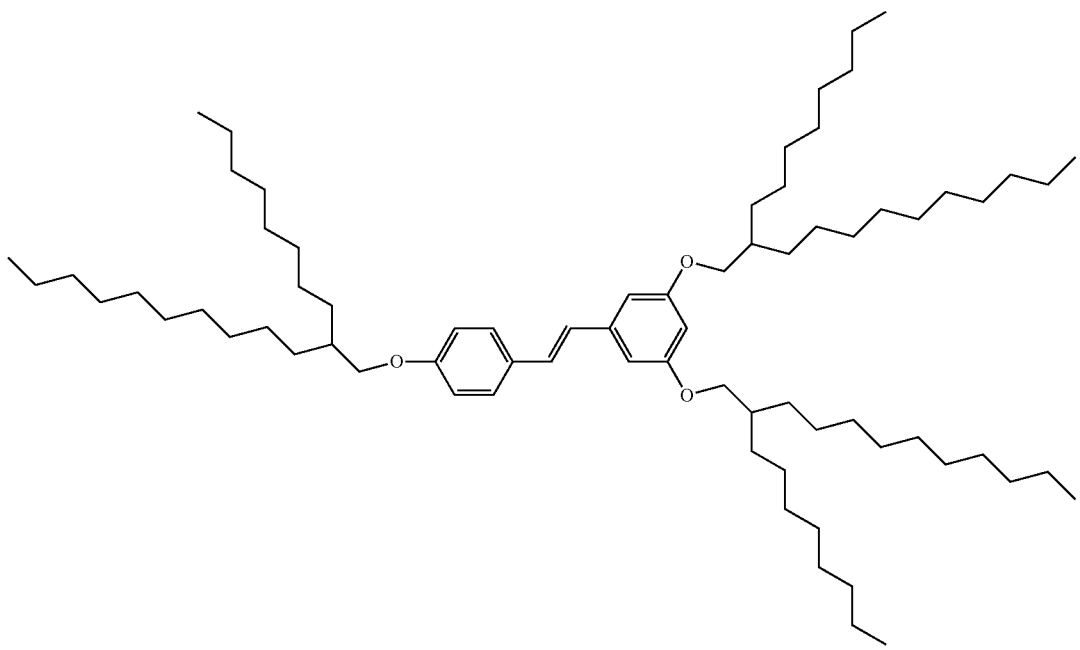

[C.19]

STLB is a colorless transparent ambient temperature liquid-form organic material, and STLB exhibits a trans-cis isomerism upon a UV light irradiation. Since the isomerization reverse reaction requires a photosensitizer, a benefit is realized with an information memory medium in which an optoelectronic information as a cis form is stored in a thermally stable manner.

As a further ambient temperature liquid-form organic material, another ambient temperature liquid-form organic material wherein the π-conjugated molecule is azobenzene, all of the 2 or more side chains are branched alkyl chains (swallowtail) and the substituent S is ether, which satisfies the formula shown below, is preferred. The 2 branched alkyl chain-bearing ambient temperature liquid-form organic material is referred to as AZO.

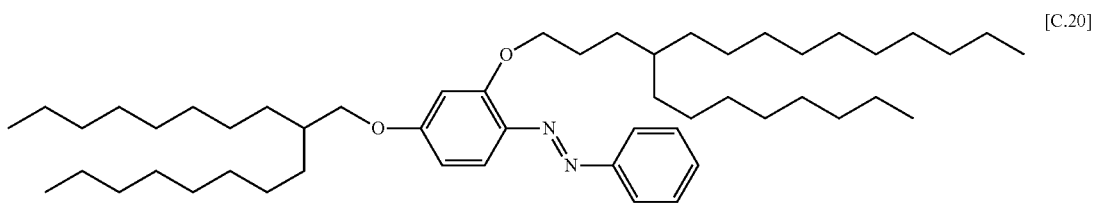 [SMILES: CCCCCCCCCCC(CCCCCCCC)CCCOc1cc(OCC(CCCCCCCC)CCCCCCCC)ccc1/N=N/c1ccccc1]

[C.20]

AZO is a reddish tan ambient temperature liquid-form organic material, and AZO exhibits a trans-cis isomerism upon a UV light irradiation. Since an isomerization reverse reaction occurs readily under a visible light such as a room light, a benefit is realized in inducing a dynamic change accompanying to the photoisomerization.

The 2 or more side chains of P1, P2, OPV1 to OPV4, ACN1, ACN2, FL1 and the like, STLB and AZO described typically above are only illustrative rather than limitative.

A further π-conjugated molecule for the purpose of color development or luminescence and/or development of a property derived from a metal is a metal-coordinating π-conjugated molecule. Typically, the metal-coordinating π-conjugated molecule is selected from the group consisting of 2,2'-bipyridine, 1,10-phenanthroline, terpyridine, cyclic π-conjugated molecule and derivatives thereof. The cyclic π-conjugated molecule may typically be porphyrin, phthalocyanine and derivatives thereof.

The metal coordinated in the π-conjugated molecule is selected typically from the group consisting of Mg, Al, Si, Ti, V, Cr, Mn, Fe, Co, Ni, Cu, Zn, Ga, Ge, Ru, Rh, Pd, Sn, Os, Pt, Au, Ce, Nd, Eu and Lu.

On the basis of the combination of the selected π-conjugated molecule with the metal, an ambient temperature liquid-form organic material developing a desired function of pigment, luminescence, magnetic property and the like can be provided. For example, when the selected π-conjugated molecule is 2,2'-bipyridine and the selected metal is Ru, then the resultant ambient temperature liquid-form organic material can possesses a red color-developing pigment and an electron donating function. Alternatively, when the selected π-conjugated molecule is porphyrin and the selected metal is Pt, then the resultant ambient temperature liquid-form organic material can exhibit a more intense luminescent property when compared with P1 described above. Alternatively, when the selected π-conjugated molecule is porphyrin and the selected metal is Ni or Cu, then the resultant ambient temperature liquid-form organic material can exhibit a magnetic property derived from a spin by Ni or Cu. When the selected metal is Fe, then the resultant ambient temperature liquid-form organic material can have an oxygen supplying ability attributable to Fe. Thus, the π-conjugated molecule and the metal may be selected depending on the desired function.

Also as another metal-coordinating π-conjugated molecule for the purpose of color or luminescence development, a ferrocene derivative can be employed.

In addition, the ambient temperature liquid-form organic material of the present invention enables, as a result of direct introduction of a hydrogen bonding substituent into the π-conjugated molecule, the conversion into an elastomer or a cluster. Thus, the introduction of the hydrogen bonding substituent allows the π-π interaction of the π-conjugated molecule to be maintained to some extent rather than be disrupted completely. As a result, an ambient temperature liquid-form organic material which is in a liquid form and is also an elastomer or a cluster can be obtained. Such a hydrogen bonding substituent is selected from the group consisting of —CH$_2$—OH, —C(=O)—OH, —NH$_2$, —NH—C(=O)— and —C(=O)—NH.

The ambient temperature liquid-form organic material which has been converted into an elastomer or a cluster also has a property inherent in the π-conjugated molecule. Accordingly, an ambient temperature liquid-form organic material which, for example, has an excellent conductivity and is in a paste form is beneficial when applied to an electrochemical capacitor, a conductive paste, a semiconductor device and an actuator, since it enables coating and fabrication without any solvent.

An illustrative method for producing an ambient temperature liquid-form organic material of the present invention is described below. An illustrative method for producing an ambient temperature liquid-form organic material, for example, in which all of the 2 or more side chains are branched alkyl chains and these branched alkyl chains are bound directly to the π-conjugated molecule is shown below.

Step S110: An alcohol consisting of a branched alkyl chain is oxidized to form an aldehyde. Since R1 and R2 mentioned here have the meanings, the description is omitted.

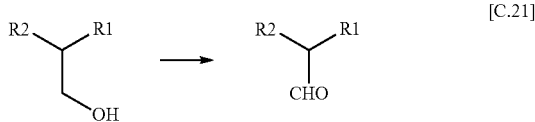

[C.21]

Step S120: The aldehyde obtained in Step S110 is reacted with a π-conjugated molecule source. As a result, the aldehyde obtained in Step S110 is introduced into the π-conjugated molecule. As used herein, the π-conjugated molecule source may be any molecule which becomes the π-conjugated molecule as a result of the reaction.

For example, when obtaining the P1, Step S110 employs an alcohol wherein R1 and R2 are represented by the formulae shown below.

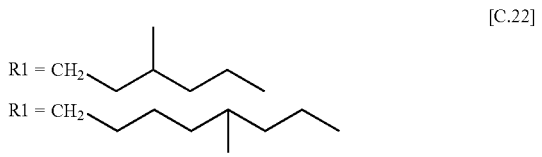

[C.22]

The alcohol is oxidized in the presence of (COCl)$_2$, CH$_2$Cl$_2$, dimethyl sulfoxide (DMSO) and triethylamine.

Then, in Step S120, the aldehyde obtained and pyrrole as a π-conjugated molecule source are refluxed in the presence of p-toluenesulfonic acid hydrate and 2,3,5,6-tetrachloro-1,4-benzoquinone (TCQ). As a result, P1 is obtained.

An illustrative method for producing the ambient temperature liquid-form organic material, for example, in which all of the 2 or more side chains are branched alkyl chain and these branched alkyl chains are bound via substituents to the π-conjugated molecule is shown below. For convenience, the substituent here is the combination of phenyl and ether.

Step S210: The alcohol consisting of branched alkyl chains is halogenated to a halide. Since R1 and R2 mentioned here have the meanings, the description is omitted. X designated here is a halogen element selected from the group consisting of Cl, Br and I. X is preferably Br for the easiness of the reaction.

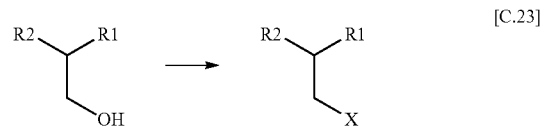

[C.23]

Step S220: Hydroxyphenyl benzaldehyde is reacted with the halide obtained in Step S210 to obtain an ether compound (alkyloxybenzaldehyde).

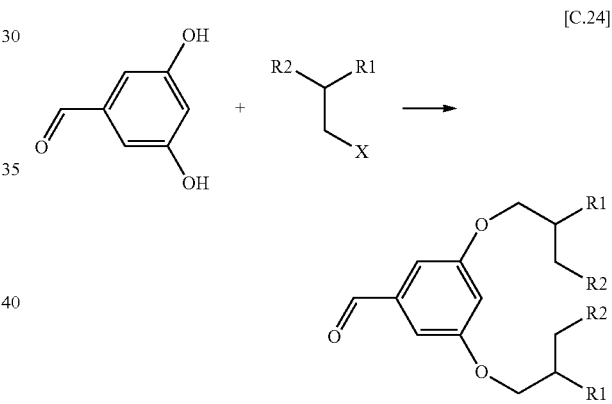

[C.24]

Step S230: The ether compound obtained in Step S220 is reacted with pyrrole as a π-conjugated molecule source. As a result, the ether compound obtained in Step S220 is introduced as a π-conjugated molecule into porphyrin. Thus, ambient temperature liquid-form organic material is obtained.

In Step S210, when using an alcohol wherein R1 and R2 are represented by the formulae shown below, the ambient temperature liquid-form organic material of the P2 is obtained. Also when Step S210 employs an alcohol wherein R1 and R2 are represented by the formulae shown below and Step 230 employs tetraethyl-1,4-phenylenebis(methylene) diphosphonate as a π-conjugated molecule source, the ambient temperature liquid-form organic material of the OPV1 is obtained.

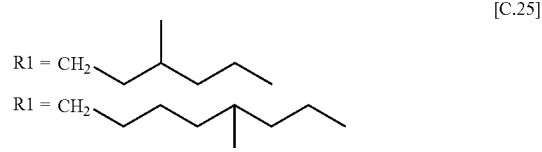

[C.25]

It should be understood that these liquid-form organic material production method of the invention are only illustrative, and may appropriately be modified depending on the type and the number of the 2 or more side chains as well as the type of π-conjugated molecule.

Embodiment 2

The application of the ambient temperature liquid-form organic material of the present invention detailed in Embodiment 1 is described below.

First, the application utilizing the optoelectronic properties possessed by the ambient temperature liquid-form organic material of the present invention is described in detail.

FIG. 1 shows a schematic view of a photovoltaic device employing an ambient temperature liquid-form organic material of the present invention.

The photovoltaic device 100 of the present invention comprises a transparent electrode 110, a photovoltaic part 120 and a counter electrode 130. The photovoltaic part 120 comprises the ambient temperature liquid-form organic material described in Embodiment 1.

The photovoltaic device 100 is constituted so that the light to be optoelectronically converted is incident from the side of the transparent electrode 110. The photovoltaic device 100 may be supported by a supporting substrate allowing for the transmission of the light to be optoelectronically converted, such as a glass substrate, a resin substrate and the like in the side of the transparent electrode 110.

The transparent electrode 110 may be any electrode allowing the light to be optoelectronically converted to transmit to the photovoltaic part 120, which can typically be a transparent conductive film of ITO, $SnO_2$, FTO, ZnO and the like, a metal film such as gold, silver, platinum and the like, a nanoparticle/nanowire, as well as a conductive polymer.

The photovoltaic part 120 comprises an electron donor 140, an electron acceptor 150 and an electrolyte solution 160. The electron donor 140 is the ambient temperature liquid-form organic material described in Embodiment 1. The electron acceptor 150 can be an electron accepting ability-possessing ambient temperature liquid-form organic material such as an ambient temperature liquid fullerene (for example, see International Publication WO2008/004635 pamphlet) and the like. The electrolyte solution 160 may be any electrolyte solution capable of transporting an electron, and a known representative one is an iodine-based electrolyte solution containing iodine ion and iodine.

While FIG. 1 shows an example in which the ambient temperature liquid-form organic material of the present invention can serve as an electron donor 140 itself, the ambient temperature liquid-form organic material of the present invention may be used as a solvent for the electron donor 140 and the electron acceptor 150, with another solid electron donor and/or electron acceptor being dissolved. In such a case, the solid electron donor 140 may for example be porphyrin, perylenebisimido, OPV and a donor inorganic nanoparticle, and the solid electron acceptor 150 may for example be fullerene, phthalocyanine and an acceptor inorganic nanoparticle.

While the counter electrode 130 is not limited particularly, it consists of a metal, carbon or a material similar to that for the transparent electrode 110. The metal may be Au, Ag, Cu, Pt, Rh, Ru, Al, Mg, In and the like.

According to the photovoltaic device 100 of the invention, a photovoltaic part 120 can employ the ambient temperature liquid-form organic material as the electron donor 140 itself, and also as a solvent for the electron donor and the electron acceptor 150, thereby eliminating the need of using an existing solvent for dissolving the electron donor or the electron acceptor. As a result, the photovoltaic device itself can be compact-sized thin film. Also since no solvent is employed, there is no environmental burden, thereby eliminating the deterioration of the performance due to the solvent leakage. The ambient temperature liquid-form organic material enables a high temperature operation because of its involatile nature, resulting in an excellent environment resistance. Furthermore, a highly active molecule can be placed on the surface of the electrode, since the inside of the photovoltaic part 120 is kept always in a state in which the electron donor 140 and the electron acceptor 150 are diffused uniformly. As a result, the deterioration of the performance is suppressed, while a physical defect can spontaneously be repaired by diffusion.

Also in the photovoltaic device 100 of the invention, the photovoltaic part 120 can employ the ambient temperature liquid-form organic material as a solvent for the electron donor 140 and the electron acceptor 150, which allows the electron donor 140 and the electron acceptor 150 to undergo the interaction at a higher density.

The operation of the photovoltaic device 100 of the invention is described below. The light to be converted optoelectronically (for example, a visible light) is incident, via the transparent electrode 110, into the photovoltaic part 120. The incident light excites the electron donor 140 to cause a transition from an electronically ground state into an excited state. The excited electron is injected into the electron acceptor 150, and moves through an outer circuit (not shown) to the counter electrode 130. The electron thus having moved to the counter electrode 130 is transported by the ion in the electrolyte solution 160, and returns to the electron donor 140 again. This process allows an electric energy to be taken out. When the electron donor 140 here is the ambient temperature liquid-form organic material, then the ambient temperature liquid-form organic material will be excited.

The application utilizing the luminescent property possessed by the ambient temperature liquid-form organic material of the present invention is detailed below.

Figure 2:
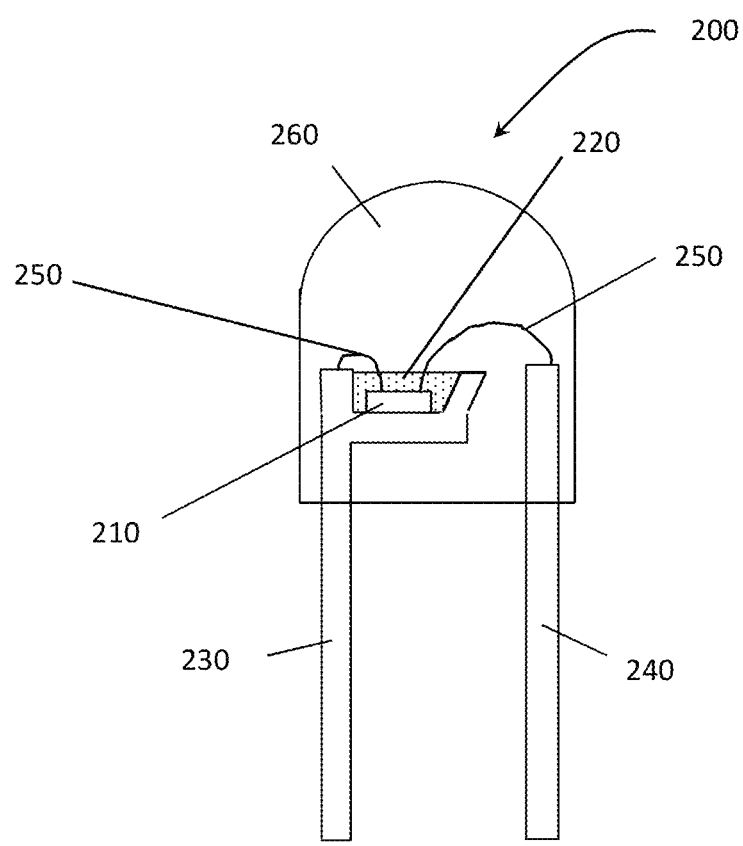
FIG. 2 shows a schematic view of a lighting apparatus employing an ambient temperature liquid-form organic material of the present invention.

FIG. 2 shows a schematic view of a lighting apparatus employing an ambient temperature liquid-form organic material of the present invention.

A lighting apparatus 200 here is a cannonball type white light-emitting diode lamp 200. The lighting apparatus 200 comprises an excitation light source 210 and a wavelength conversion part 220.

More specifically, the excitation light source 210 and the wavelength conversion part 220 are mounted on a lead wire 230. The excitation light source 210 and the lead wires 230, 240 are connected electrically via a fine gold wire 250. The excitation light source 210 and the wavelength conversion part 220 are coated altogether entirely with a transparent substance 260.

The wavelength conversion part 220 comprises the ambient temperature liquid-form organic material described in Embodiment 1 as a luminescent material. The wavelength conversion part 220 may consist of a single ambient temperature liquid-form organic material or a combination thereof, or may consists of such a single material or a combination thereof with a polymeric sealant for sealing the excitation light source 210 such as an epoxy resin.

Since no polymeric sealant is required when the wavelength conversion part 220 employs the ambient temperature liquid-form organic material according to the present invention, problems of a non-uniform mixture of an existing ceramic luminescent material and the polymeric sealant or a precipitation of the existing ceramic luminescent material in the polymeric sealant do not occur. Also since the ambient temperature liquid-form organic material of the present invention is non-volatile, the luminescent property is not changed. Also since the luminescent material is in a liquid form at ambient temperature, the problems do not occur even when the wavelength conversion part 220 employs the ambient temperature liquid-form organic material according to the present invention and the polymeric sealant. Accordingly, the luminescent property and the production yield of the lighting apparatus 200 can be improved.

The operation of the lighting apparatus 200 is described below. The wavelength conversion part 220 employed here consists of the ambient temperature liquid-form organic material which emits a yellow light upon irradiation of a blue light (for example, a wavelength of 450 nm), and the excitation light source 210 is a blue light emission diode device. Via the lead wires 230 and 240, the excitation light source 210 emits the blue light of a wavelength of 450 nm. The blue light is floodlit onto the wavelength conversion part 220, and converted into a yellow light by the ambient temperature liquid-form organic material of the wavelength conversion part 220. The lighting apparatus 200 emits a white light as a mixture of the blue light and the yellow light.

The ambient temperature liquid-form organic material of the present invention emits a light, depending on the selection of the π-conjugated molecule and the type of 2 or more side chains, upon excitation by a vacuum ultraviolet light of 100 to 190 nm, an ultraviolet light of 190 to 380 nm, an electron power and the like. For example, OPV1 to OPV4 are excited by an ultraviolet light to emit a blue light. Accordingly, the ambient temperature liquid-form organic material of the present invention as a luminescent material can be combined with an excitation source such as a vacuum ultraviolet light, an ultraviolet light and an electron power to construct an image display device. The image display device includes a vacuum fluorescent display (VFD), a field emission display (FED), a plasma display panel (PDP), a cathode ray tube (CRT) and the like.

In addition, the luminescent material utilizing the luminescent property of the ambient temperature liquid-form organic material of the present invention can be utilized also in a luminescent paint. Since the ambient temperature liquid-form organic material of the present invention does not require any use of a solvent, the environmental burden is reduced and a problematic change in the luminescent property due to the solvent evaporation is eliminated.

Another application utilizing the luminescent property possessed by the ambient temperature liquid-form organic material of the present invention is detailed below.

Figure 3:
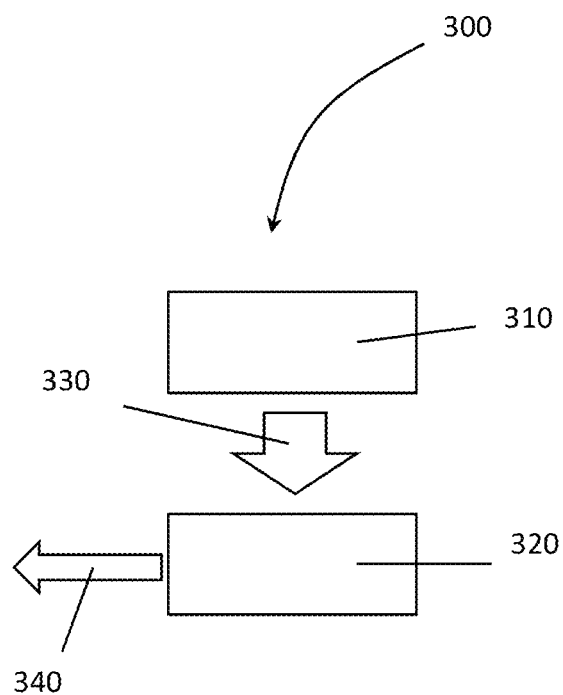
FIG. 3 shows a schematic view of a laser device employing an ambient temperature liquid-form organic material of the present invention.

FIG. 3 shows a schematic view of a laser device employing an ambient temperature liquid-form organic material of the present invention.

A laser device 300 comprises an excitation source 310 and a laser medium 320. The excitation source 310 is any excitation source capable of exciting the laser medium 320, and in the case for example where the laser medium 320 absorbs the ultraviolet light and emits a light, then the excimer laser (excitation wavelength 308 nm) can be used. The laser medium 320 is an ambient temperature liquid-form organic material of the present invention filled in a cell and the like which allow for the transmission of an excitation light 330 from the excitation source 310. Since the ambient temperature liquid-form organic material of the present invention does not require a solvent or a polymer matrix, the deterioration of the luminescent property due to the solvent evaporation is eliminated, and a highly efficient property of the high density luminescent material can be exhibited. As a result, a laser device having an excellent luminescent property can be provided. Also since it needs no solvent, it serves for environmental protection.

It is known that when a fluorescent pigment which is an existing organic material is used as a laser medium, the fluorescent pigment aggregates and the fluorescence quantum yield is reduced, resulting in a reduced gain. In order to prevent this, an existing laser medium consists of the fluorescent pigment dispersed in a transparent polymer matrix at a concentration as low as several percents. The ambient temperature organic material of the invention allow a pigment-bearing π-conjugated molecule to be present at a high density without aggregation, thereby being hopeful in achieving a markedly improved performance.

The operation of such a laser device 300 is described below. In this case, the excitation source 310 is the excimer laser (excitation wavelength 308 nm), and the laser medium 320 is the ambient temperature liquid-form organic material which emits the visible light by the excimer laser. From the excitation source 310, the excitation light 330 is incident on the laser medium 320. By the incident excitation light 330, the laser medium 320 is excited to emit a visible light 340. Such a visible light 340 can be taken for example into an optical fiber (not shown) and then utilized in a detecting device and the like.

The application utilizing the color development by the ambient temperature liquid-form organic material of the present invention is detailed below.

Figure 4:
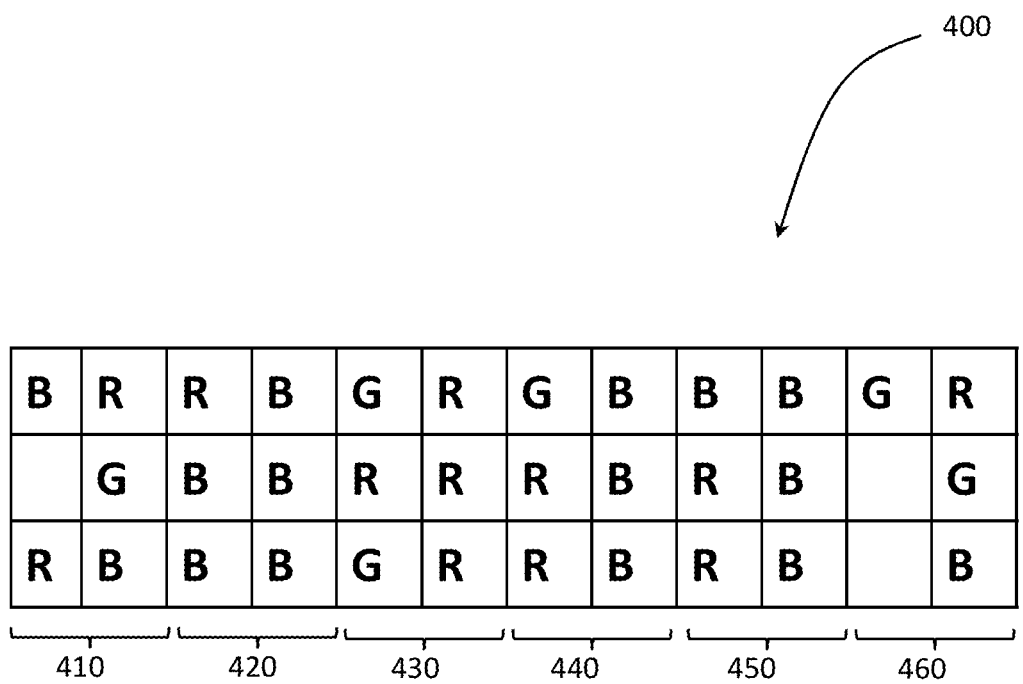
FIG. 4 shows a schematic view of a color barcode employing an ambient temperature liquid-form organic material of the present invention.

FIG. 4 shows a schematic view of a color barcode employing an ambient temperature liquid-form organic material of the present invention.

A color barcode 400 shown in FIG. 4 is a color barcode made based on the table described in FIG. 2 to FIG. 10 in Unexamined Japanese Patent Application Publication No. 2004-355122. In the color barcode 400, the cells of R, G and B are printed respectively by an ink consisting of the ambient temperature liquid-form organic material of the present invention undergoing the color development of RED (red color), an ink consisting of the ambient temperature liquid-form organic material of the present invention undergoing the color development of GREEN (green color) and an ink consisting of the ambient temperature liquid-form organic material of the present invention undergoing the color development of BLUE (blue color). Each color-developing ambient temperature liquid-form organic material can be prepared, as detailed in Embodiment 1, on the basis, for example, of the type of the π-conjugated molecule.

With referring to Unexamined Japanese Patent Application 2004-355122, the color barcode 400 includes a region 410 as a START code, a region 420 as a character "N", a region 430 as a character "I", a region 440 as a character "M", a region 450 as a character "S", and a region 460 as an END code. As a result, the color barcode 400 stores an information "NIMS".

The information possessed by such a color barcode 400 can be read for example by using a barcode reader disclosed in Unexamined Japanese Patent Application 2004-355122.

It is a matter of course that the color barcode shown in FIG. 4 is merely an example, and application can be made not only to a simple dot but also to a two dimensional, QR codes and the like.

As discussed above, a precise and minute drawing is possible when the ambient temperature liquid-form organic material of the present invention is employed as an ink material and used in a color barcode, since the solvent (such as polymeric medium) as an ink material is not needed. Thus, since a highly dense printing and a diverse morphology can be achieved when the ambient temperature liquid-form organic material of the present invention exhibiting a diverse color development is employed as an ink material to make a color barcode, the record density and the information content can be improved.

While the present invention is further detailed below using typical examples, it should be noted that the present invention is not limited to such examples.

Example 1

In Example 1, the P1 was synthesized.

Figure 5:
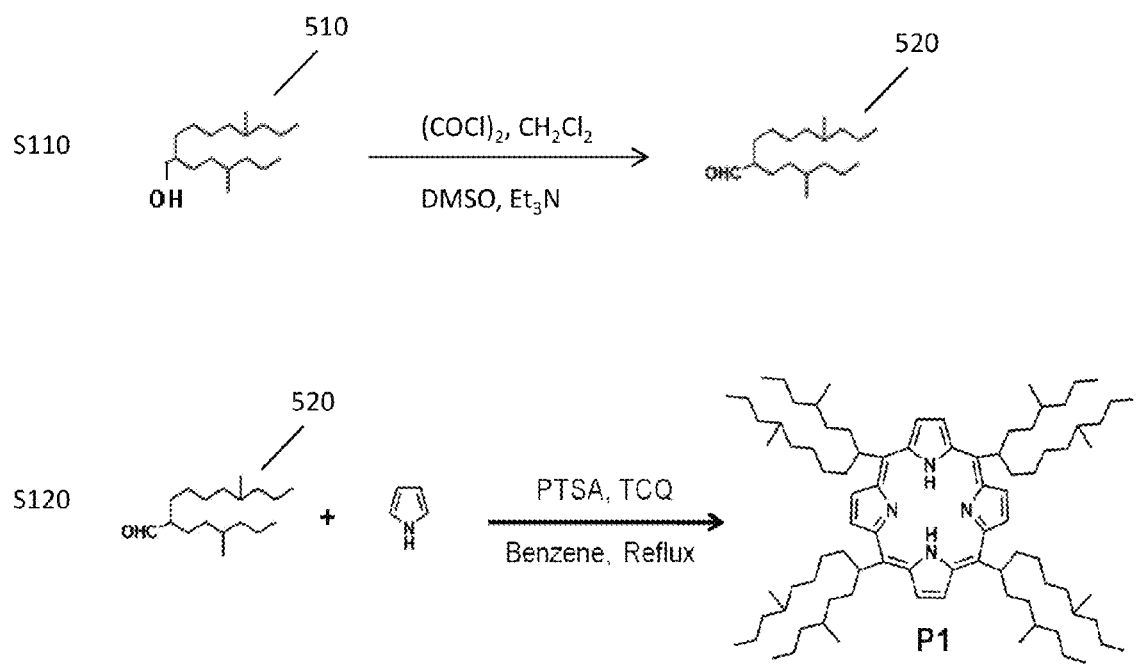
FIG. 5 shows an illustration of the manufacture process for synthesizing P1 of Example 1.

FIG. 5 shows an illustration of the manufacture process for synthesizing P1 of Example 1.

An alcohol 510 was oxidized in the presence of $(COCl)_2$, $CH_2Cl_2$, dimethyl sulfoxide (DMSO) and triethylamine to obtain an aldehyde 520 (Step S110).

Then, a solution of p-toluenesulfonic acid hydrate (p-TsOH·$H_2O$) (20 mg, 0.1 mmol) dissolved in benzene (600 ml) was heated under reflux for 2 hours in a dark place under a nitrogen atmosphere. The heating under reflux employed a round bottom flask (11) fitted with a Dean-Stark trap and a condenser. The aldehyde 520 (2.2 g, 7.5 mmol) obtained in Step S110 and pyrrole (0.5 ml, 7.5 mmol) as a π-conjugated molecule source were added to the solution having been heated under reflux and heated for further 15 minutes. Thereafter, this solution was combined with 2,3,5,6-tetrachloro-1,4-benzoquinone (TCQ) (0.83 g, 3.4 mmol) and heated for further 30 minutes under reflux (Step S120).

The reaction mixture thus obtained was cooled and the solvent was removed under reduced pressure. The residue was dissolved in dichloromethane, filtered through a silica gel short plug, and washed with dichloromethane. The eluent was recovered and dried. The residue was purified by a silica gel column chromatography (n-hexane/chloroform, 9.5:0.5) to obtain a purple liquid (0.8 g, yield: 8.6%).

The purple liquid thus obtained was confirmed to be P1 by a proton nuclear magnetic resonance spectrometry ($^1$H NMR) (DMX400, manufactured by Bruker Corporation), a laser desorption/ionization time-of-flight mass spectrometer (MALDI-TOF-MS) (AXIMA-CFR Plus, manufactured by Shimadzu Corporation) and a UV visible light spectrophotometer UV/vis (Cary 50 Conc, manufactured by Varian Inc.).

$^1$H NMR (400 MHz, $CDCl_3$): δ=−2.32 (br s, 2H, NH), 0.52-0.66 (m, 48H, $CH_3$), 0.90-1.3 (m, 64H, $CH_2$), 1.52-1.71 (m, 8H, $(CH_3)CH(CH_2)_2$, 2.62-2.84 (m, 16H, $C_\beta H$), 5.00-5.11 (m, 4H, $C_\alpha H$), 9.47 (s, 8H, β-pyrrolic H)

MALDI-TOF-MS (matrix:dithranol): $C_{88}H_{150}N_4$: Calculated: 1263.19. Found: 1262.36[M$^+$]

UV-vis (dichloromethane): λ=404 nm (ε=63900M$^{-1}$ cm$^{-1}$), 422 nm (ε=317000M$^{-1}$ cm$^{-1}$), 524 nm (ε=12700M$^{-1}$ cm$^{-1}$), 560 nm (ε=8600M$^{-1}$ cm$^{-1}$), 604 nm (ε=3900M$^{-1}$ cm$^{-1}$), 661 nm (ε=5400M$^{-1}$ cm$^{-1}$)

Figure 16:
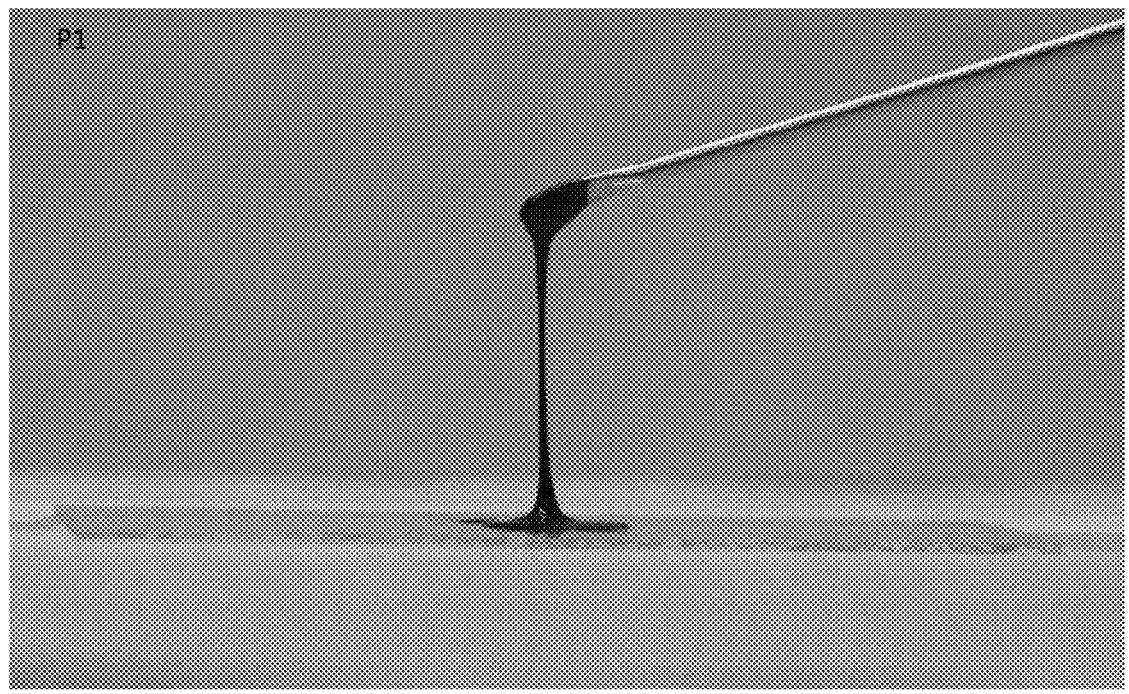
FIG. 16 is an image showing the state of P1 under a visible light according to Example 1.

A high resolution digital color camera (EOS 50D, manufactured by Canon Inc.) was used to take a photograph of the appearance of P1 at room temperature (under the visible light). The results are shown in FIG. 16 and described below.

An absolute PL quantum yield measurement device (C9920-02G, manufactured by Hamamatsu Photonics KK) was used to obtain the absolute fluorescence quantum yield of P1. The measurement results are shown in Table 1 and described below.

The rheology characteristics of P1 were measured at 20° C. using a rheology measurement device (Anton Paar Physica MCR301). For each shear force (γ=0.01, 0.10 and 1.00), the frequency dependencies of the storage modulus G' and the loss modulus G" were obtained. The complex viscosity η* was calculated using Stokes-Einstein's equation and Fick's rule. The results are shown in FIGS. 21, 22, 25 and 26 and described below.

Figure 39:
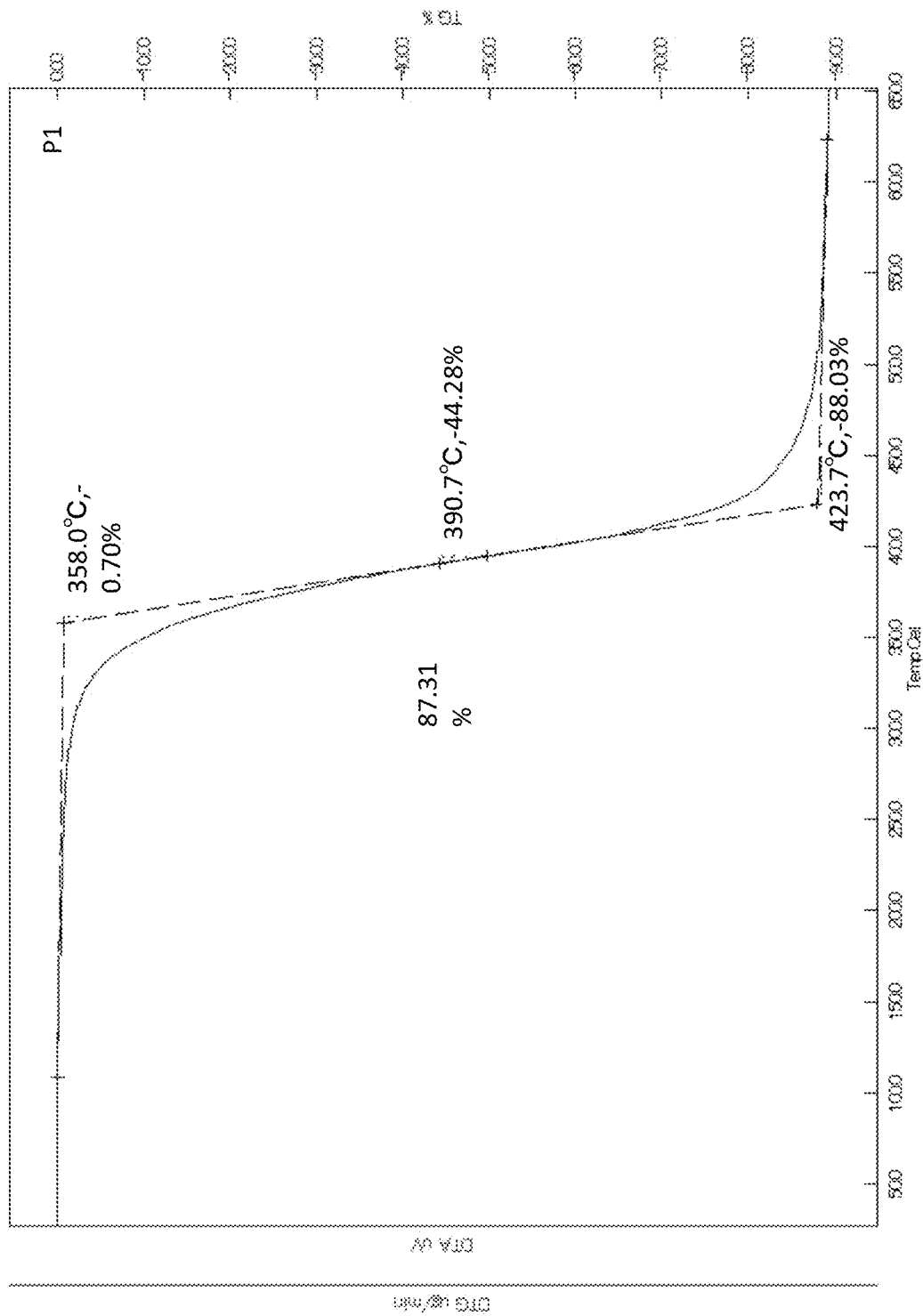
FIG. 39 shows an illustration of the results of thermogravimetric analysis of P1 according to Example 1.

A thermogravimetric measurement device (EXSTAR TG/DTA6200, manufactured by Seiko Instruments Inc.) was used to measure the degradation temperature of P1. At a heating rate of 10° C./min, heating was continued from 20° C. to 650° C. while measuring the change in the weight of P1. The results are shown in FIG. 39 and described below.

Figure 40:
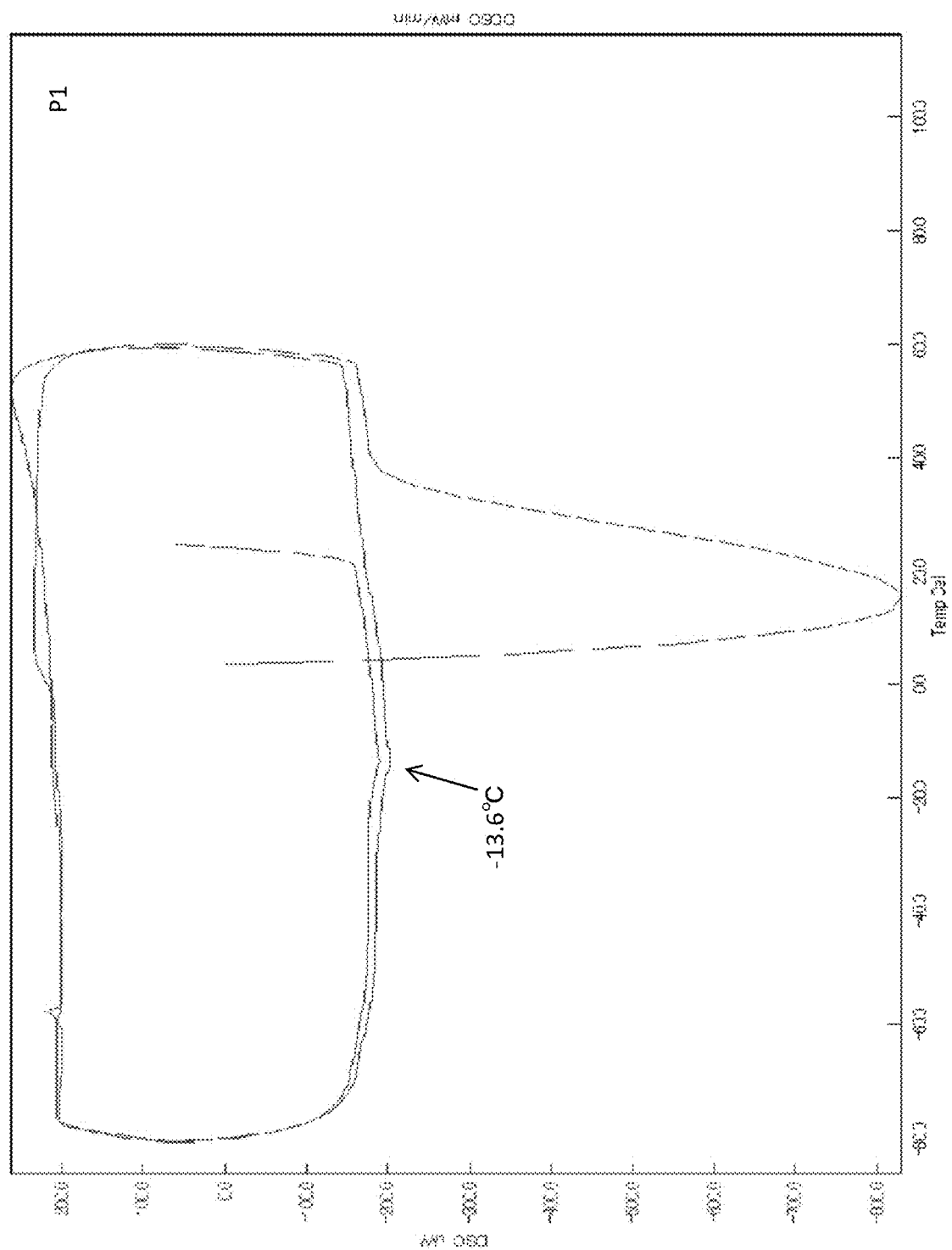
FIG. 40 shows an illustration of the results of the differential scanning calorimetry of P1 according to Example 1.

A differential calorimetric measurement device (SXSTAR DSC6220, manufactured by Seiko Instruments Inc.) was used to measure the melting point of P1. While scanning from 20° C. to −80° C., then from −80° C. to 60° C., then from 60° C. to 0° C. again, the change in the calorie of P1 was measured. The measurement results are shown in FIG. 40 and described below. The glass transition temperature obtained from the measurement results was shown in Table 2.

Figure 46:
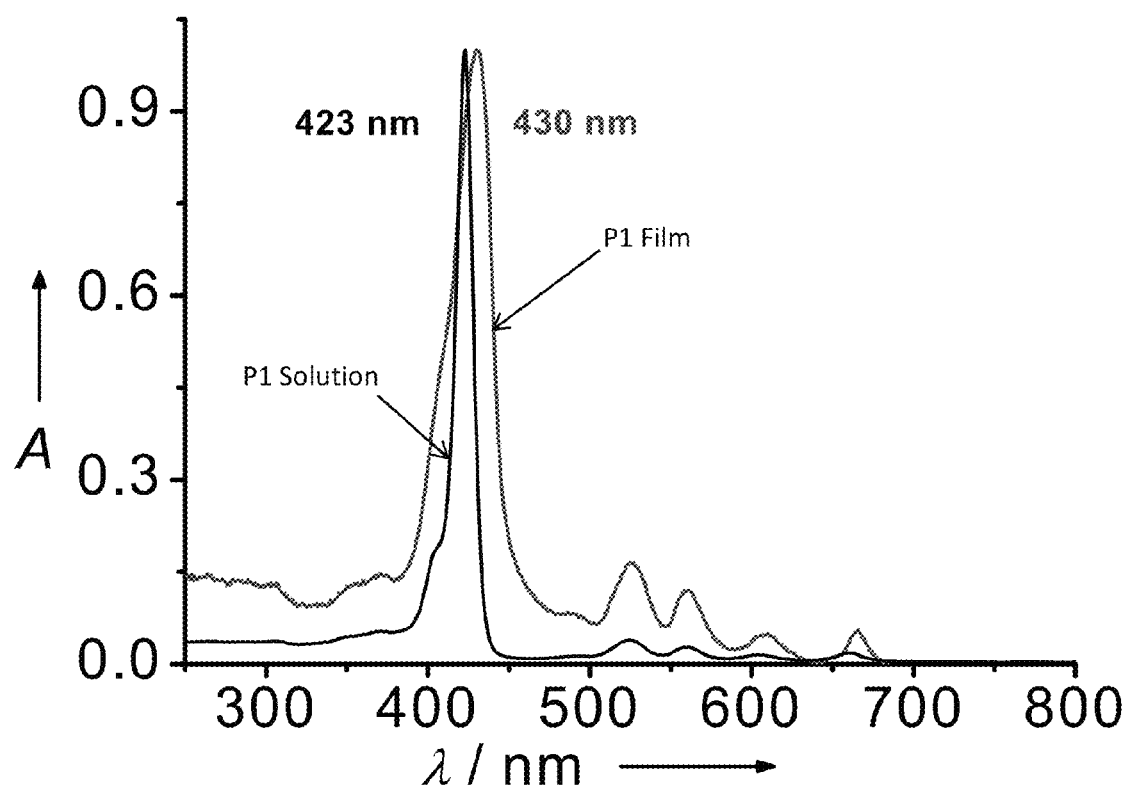
FIG. 46 shows an absorption spectrum of P1 according to Example 1.

Using the UV visible spectrophotometer, the absorption spectrum of P1 was measured. The samples for the measurement were a solution of P1 dissolved in dichloromethane (1×10$^{-5}$M) (referred to as P1 Solution) (cell length l=1 cm) and a film formed by spin coating of P1 Solution on a quartz substrate (referred to as P1 Film, P1 Film is a film consisting of P1 itself formed after the dichloromethane solution was readily evaporated). The results are shown in FIG. 46 and described below.

Figure 47:
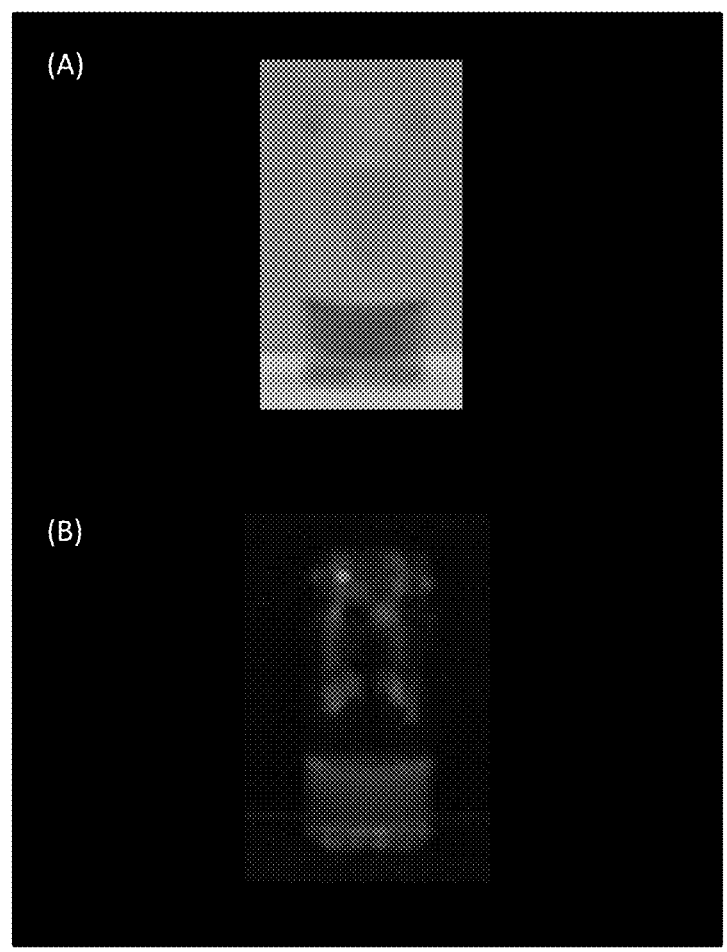
FIG. 47 is an image showing a luminescent state of P1 according to Example 1.

Then, the high resolution digital color camera was used to take a photograph of the luminescent state of P1 upon irradiation of the ultraviolet light (wavelength 365 nm). The sample for the measurement was P1 Solution. The results are shown in FIG. 47 and described below.

Figure 48:
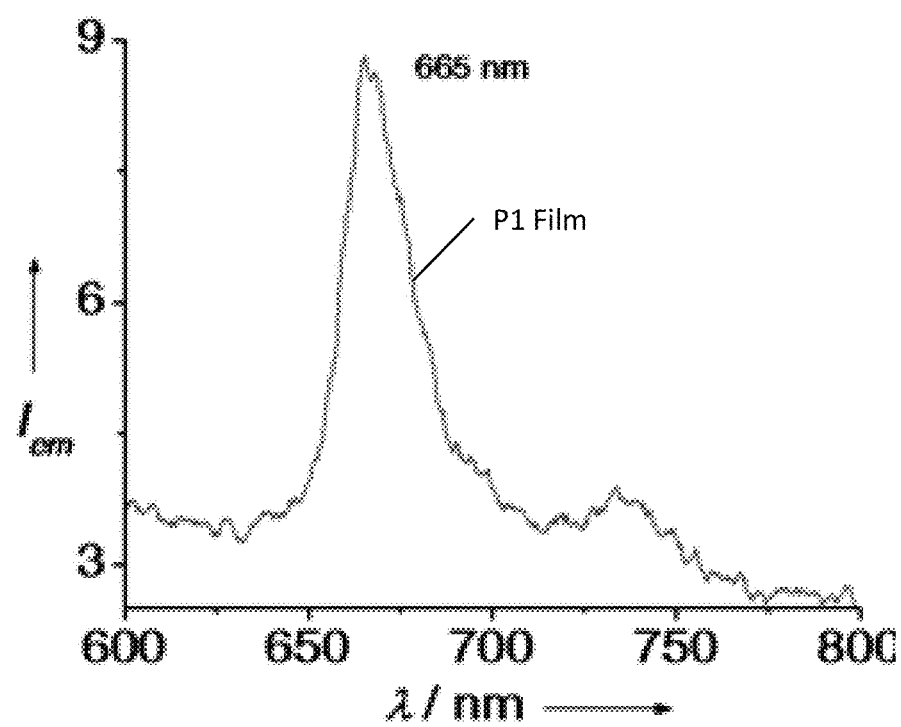
FIG. 48 shows a luminescent spectrum of P1 according to Example 1.

The fluorescent spectrophotometer was used to measure the emission spectrum. The sample for the measurement was P1 Film. The emission spectrum when excited with the excitation wavelength (430 nm) is shown in FIG. 48 and described below.

Using a time-resolved microwave conductivity measurement device, the conductivity (photoconductivity) of P1 was measured. The measurement employed a light source having a wavelength of 355 nm and an output of 1×10$^{-2}$ W. The measurement results are shown in Table 3 and described below.

In addition, the validity of the photovoltaic device of P1 when used as an electron donor was verified. As an electron acceptor material, $(2,4,6)F180NC_{60}$ was synthesized.

Figure 6:
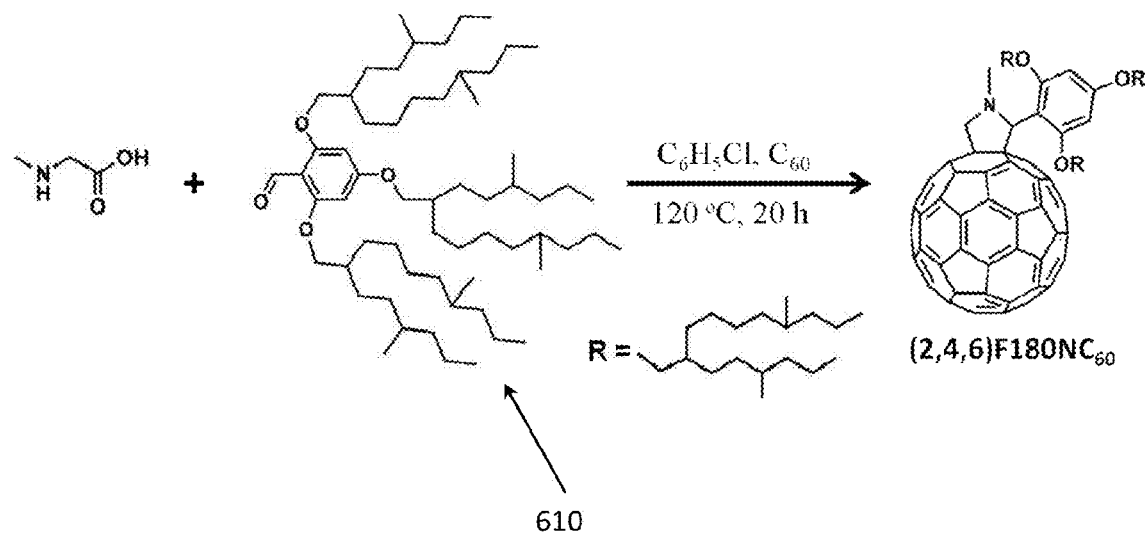
FIG. 6 shows an illustration of the manufacture process for synthesizing $(2,4,6)F180NC_{60}$.

FIG. 6 is an illustration of the manufacture process for synthesizing of $(2,4,6)F180NC_{60}$.

In dried monochlorobenzene (1100 mL), (2,4,6)F180N benzaldehyde 610 (2.0 g, 2.20 mmol), C60 (2.38 g, 3.31 mmol) and N-methylglycine (1.01 g, 11.35 mmol) were dissolved, and refluxed for 20 hours. Then, the reaction mixture was cooled to 20° C. and the solvent was removed, and thereafter, a crude product was filtered through a silica gel plug twice (toluene and $CHCl_3$). Removal of the solvent under reduced pressure and a gel permeation chromatography GPC (Bio-beads S-X3, toluene) followed by a column chromatography (silica gel, n-hexane/$CHCl_3$, 1:2) yielded a brown liquid (2.67 g, yield: 73.2%).

The brown liquid thus obtained was confirmed to be $(2,4,6)F180NC_{60}$ by $^1$H NMR, MALDI-TOF-MS, and UV/vis.

1H NMR (400 MHz, CDCl$_3$): δ=0.79-0.89 (m, 36H, CH$_3$), 1.00-1.14 (m, 6H, (CH$_3$)CH(CH$_2$)$_2$), 1.16-1.52 (m, 60H, CH$_2$), 1.89 (s, 3H, CH(CH$_2$)$_3$), 2.66 (s, 3H, NCH$_3$), 3.62-3.91 (m, 6H, OCH$_2$), 4.01-4.03 (d, J=7.6 Hz, 1H, CH$_2$NCH$_3$), 4.82-4.84 (d, J=7.6 Hz, 1H, CH$_2$NCH$_3$), 5.60 (s, 1H, CH*), 6.09 ppm (s, 2H, Ar)

MALDI-TOF-MS (matrix: 2-(4'-hydroxybenzeneazo) benzoic acid (HABA)):C$_{123}$H$_{119}$NO: Calculated: 31657.92. Found: 1654.80[M$^+$]

UV-vis (dichloromethane): λ=255 nm (ε=136000M$^{-1}$ cm$^{-1}$), 320 nm (ε=47700M$^{-1}$ cm$^{-1}$), 431 nm (ε=5400M$^{-1}$ cm$^{-1}$), 415 nm (ε=6400M$^{-1}$ cm$^{-1}$)

Figure 37:
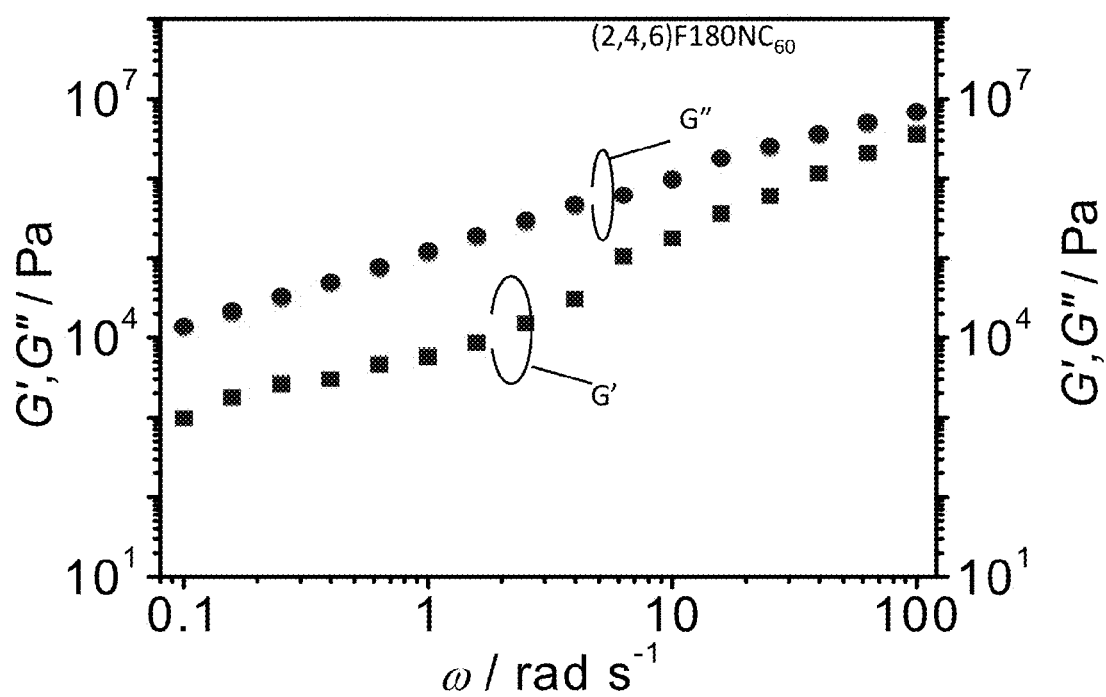
FIG. 37 shows an illustration of the frequency dependency of the storage modulus G' and the loss modulus G" of (2,4,6)F18ONC$_{60}$ at each shear force (γ=0.01, 0.10 and 1.00).
Figure 38:
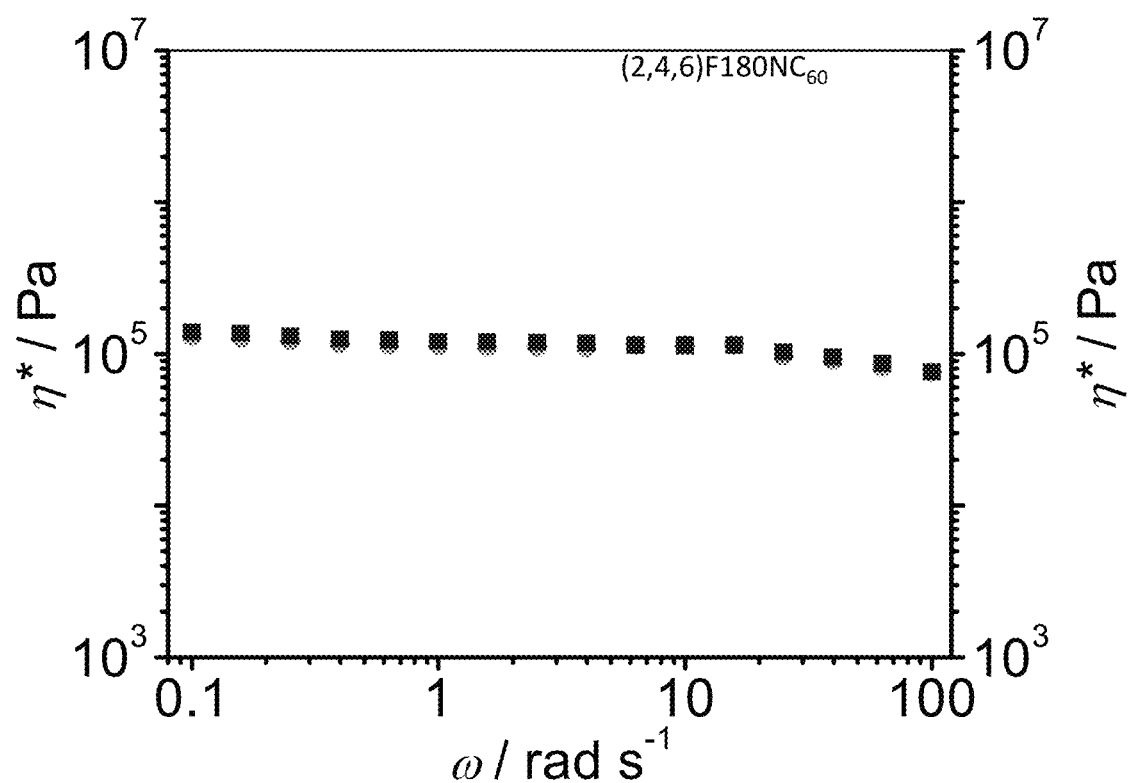
FIG. 38 shows an illustration of the frequency dependency of the complex viscosity η* of (2,4,6)F18ONC$_{60}$ at each shear force (γ=0.01, 0.10 and 1.00).

The rheology of (2,4,6)F180NC$_{60}$ was examined using the rheology measurement device to obtain the frequency dependencies of the storage modulus G' and the loss modulus G" to calculate the complex viscosity η*. The results are shown in FIGS. 37 and 38 and described below.

Figure 69:
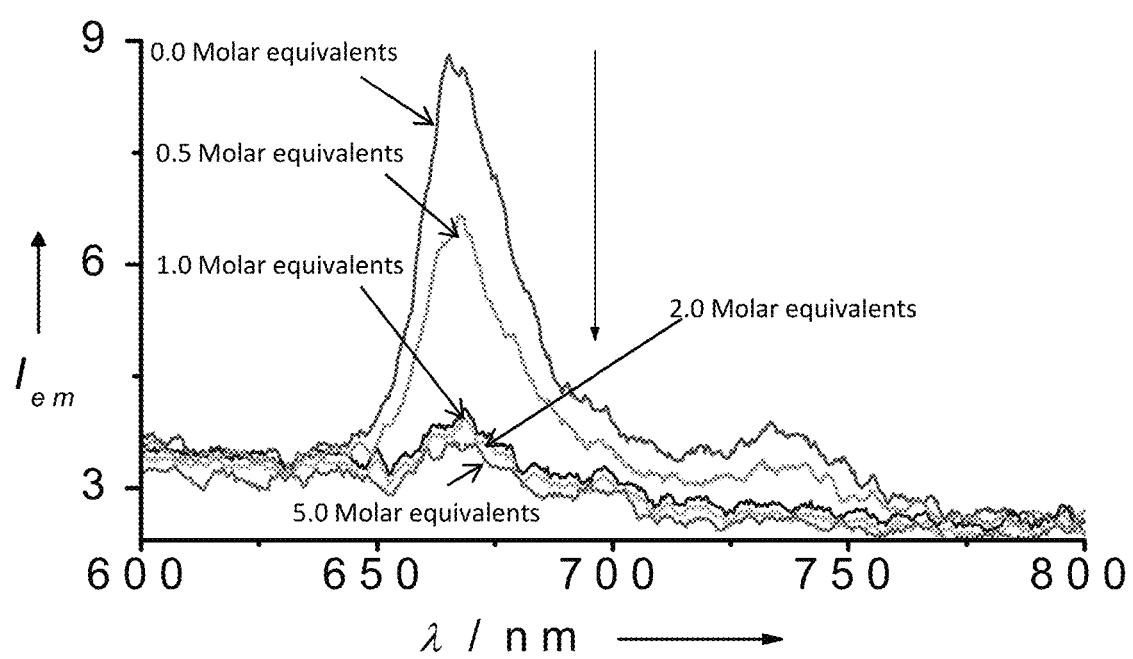
FIG. 69 shows a relationship between an emission peak intensity of P1 according to Example 1 and an amount of (2,4,6)F18ONC$_{60}$ added.

Then, using the fluorescent spectrophotometer, films obtained after coating of P1 Solutions mixed with 0.5 molar equivalents, 1.0 molar equivalents, 2.0 molar equivalents and 5.0 molar equivalents of (2,4,6)F180NC$_{60}$ were examined for the change in the luminescence respectively. The results are shown in FIG. 69 and described below.

Example 2

In Example 2, the P2 was synthesized.

Figure 7:
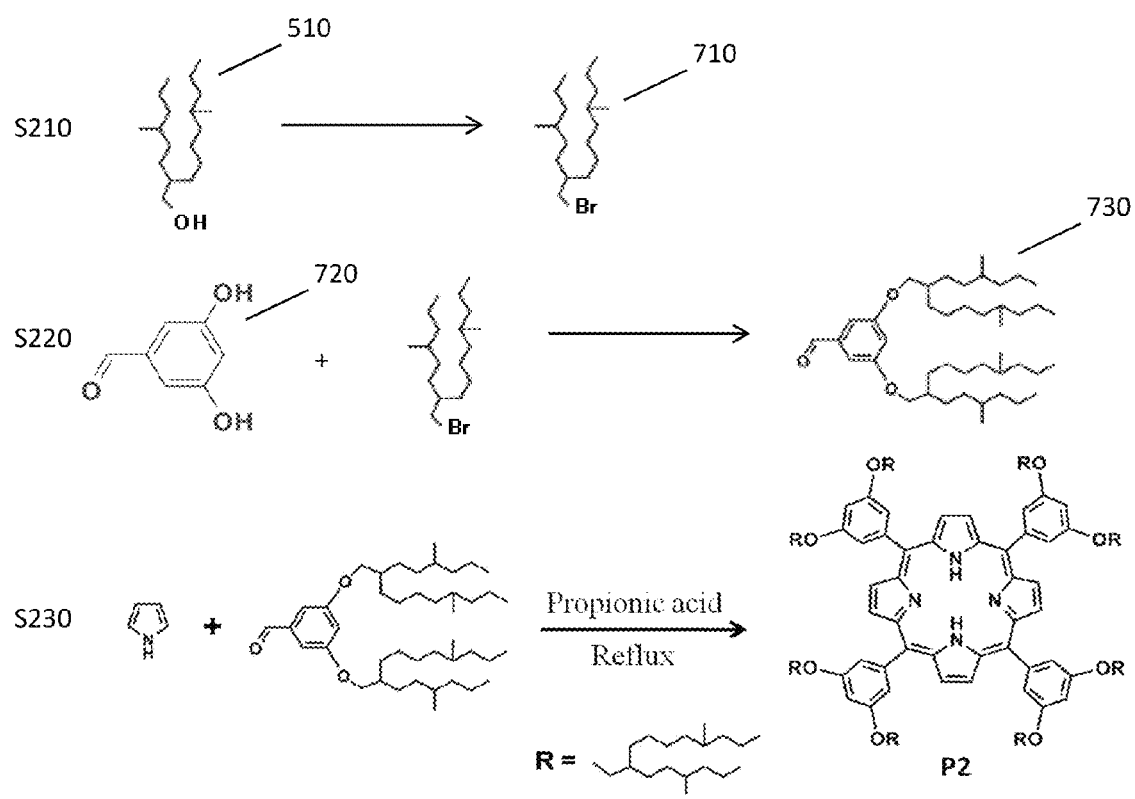
FIG. 7 shows an illustration of the manufacture process for synthesizing P2 of Example 2.

FIG. 7 shows an illustration of the manufacture process for synthesizing P2 of Example 2.

An alcohol 510 was halogenated into a halide 710 (Step S210). Then, the halide 710 and a hydroxyphenyl group 720 were reacted in the presence of K$_2$CO$_3$, KI, N,N-dimethylformamide (DMF) at 120° C. to obtain an ether compound ((3,5)F180N benzaldehyde) 730 of a 3,5-substituted benzaldehyde (Step S220).

Then, distilled pyrrole (0.12 g, 1.8 mmol) as a π-conjugated molecule source and the ether compound of 3,5-substituted benzaldehyde 730 (1.2 g, 1.8 mmol) were added to propionic acid (60 ml), and refluxed for 30 minutes (Step S230). Thereafter, the solution was cooled to room temperature, and filtrated. The filter cake was washed thoroughly with methanol. The residue was dissolved in dichloromethane, filtered through a silica gel short plug, and washed with dichloromethane. The eluent was recovered and dried. A silica gel column chromatography (n-hexane/chloroform, 9.5:0.5) was used to purify the residue, thereby obtaining a purple liquid (0.4 g, yield: 7.8%).

The purple liquid thus obtained was confirmed to be P2 by $^1$H NMR, MALDI-TOF-MS and UV/vis.

$^1$H NMR (400 MHz, CDCl$_3$): δ=−2.82 (s, 2H, NH), 0.70-0.95 (m, 96H, CH$_3$), 1.00-1.12 (m, 16H, (CH$_3$)CH (CH$_2$)$_2$), 1.15-1.42 (m, 160H, CH$_2$), 1.8-2.0 (m, 8H, CH(CH$_2$)$_3$, 3.92-4.20 (m, 16H, OCH$_2$), 6.88 (s, 4H, ArH), 7.34 (s, 8H, ArH), 8.93 (s, 8H, β-pyrrolic H)

MALDI-TOF-MS (matrix:dithranol):C$_{188}$H$_{318}$N$_4$O$_8$: Calculated: 2760.46. Found: 2759.56[M$^+$]

UV-vis (dichloromethane): λ=404 nm (ε=103000M$^{-1}$ cm$^{-1}$), 422 nm (ε=356000M$^{-1}$ cm$^{-1}$), 515 nm (ε=23800M$^{-1}$ cm$^{-1}$), 550 nm (ε=7310M$^{-1}$ cm$^{-1}$), 590 nm (ε=6800M$^{-1}$ cm$^{-1}$), 650 nm (ε=6800M$^{-1}$ cm$^{-1}$)

Similarly to Example 1, P2 was subjected to the absolute fluorescence quantum yield measurement, the measurement of the frequency dependency of the storage modulus G', the loss modulus G" and the complex viscosity η* and the absorption spectrum measurement, the emission spectrum measurement by the ultraviolet light irradiation (excitation wavelength 365 nm). The results are shown in Table 1, FIGS. 23 to 26, 49 and 50 and described below.

Also similarly to Example 1, the high resolution digital color camera was used to take a photograph of the luminescent state by the ultraviolet light excitation (wavelength 365 nm) of P2. The sample was a solution of P2 dissolved in chloroform (1×10$^{-5}$M) (referred to as P2 Solution). The results are shown in FIGS. 70(A) and (D) and described below.

Using Zinc acetate (Zn(OAc)$_2$) and a soluble fullerene (BZC60), the effect of a metal coordination in P2 and the validity of the photovoltaic device of P2 when used as an electron donor were verified. The sample was P2 Solution. Zn(OAc)$_2$ was employed for coordinating Zn in the π-conjugated molecule (porphyrin in this case) of P2. BZC60 is a phenyl group-substituted fullerene C$_{60}$ and known as a representative electron acceptor material. The high resolution digital color camera was used to take a photograph of the luminescent state of P2 Solution mixed with each of (Zn(OAc)$_2$) and BZC60 upon the ultraviolet light (wavelength 365 nm) irradiation. The results are shown in FIGS. 70(B), (C), (E) and (F) and described below.

Example 3

In Example 3, the OPV1 was synthesized.

Figure 8:
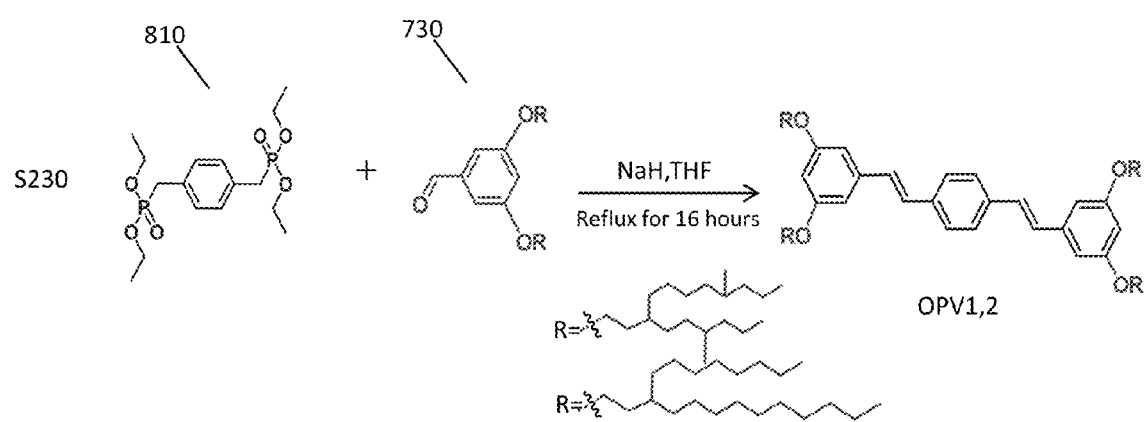
FIG. 8 shows an illustration of the manufacture process for synthesizing OPV1 and OPV2 of Examples 3 and 4.

FIG. 8 shows an illustration of the manufacture process for synthesizing OPV1 and OPV2 of Examples 3 and 4.

Since the process to obtain the ether compound 730 of 3,5-substituted benzaldehyde (Step S210 and S220) is identical to Example 2, it is omitted. To a solution of the ether compound 730 (1.49 g, 2.3 mmol) and tetraethyl-1,4-phenylenebis(methylene)diphosphonate 810 (0.45 g, 1.05 mmol), tetrahydrofuran THF (30 ml) and NaH (0.16 g, 6.9 mmol) were added under an argon atmosphere. As an R for the ether compound 730, a hyperbranch alkyl chain F180N (isostearyl group) was employed. This solution mixture was refluxed for 16 hours and the solvent was removed under reduced pressure (Step S230). The residue was extracted with chloroform, and washed several times with brine and water. The organic layer was evaporated under reduced pressure, and a silica gel column chromatography (n-hexane/chloroform, 3:1) was conducted to obtain a pale yellow liquid (1.6 g, yield: 51%).

The pale yellow liquid thus obtained was confirmed to be OPV1 by $^1$H NMR, MALDI-TOF-MS and UV/vis.

$^1$H NMR (400 MHz, CDCl$_3$): δ=0.82-0.94 (m, 48H, CH$_3$), 1.10-1.18 (m, 8H, (CH$_3$)CH(CH$_2$)$_2$, 1.20-1.46 (m, 80H, CH$_2$), 1.80 (m, 4H, CH(CH$_2$)$_3$), 3.85 (m, 8H, OCH$_2$), 6.39 (s, 2H, ArH), 6.66 (s, 4H, ArH), 7.04-7.06 (d, 4H, vinylic, J=8 Hz), 7.51 (m, 4H, Ar)

MALDI-TOF-MS (matrix:dithranol): C$_{94}$H$_{162}$O$_4$: Calculated: 1355.25. Found: 1353.29[M$^+$]

UV-vis (dichloromethane): λ$_{max}$=362 nm, ε=54480M$^{-1}$ cm$^{-1}$

Figure 17:
FIG. 17 is an image showing the state of OPV1 under a visible light according to Example 3.

Similarly to Example 1, OPV1 was subjected to the observation of the appearance under the visible light, the absolute fluorescence quantum yield measurement, the measurement of the frequency dependency of the storage modulus G', the loss modulus G" and the complex viscosity η*, the differential scanning calorimetry, the glass transition temperature measurement, the absorption spectrum measurement, the observation of the luminescence upon the ultraviolet light irradiation (excitation wavelength 365 nm), the emission spectrum measurement, the photoconductivity measurement as well as an electron donor utility verification. The results are shown in FIG. 17, Table 1, FIGS. 27, 28, 31, 32, 41, Table 2, FIGS. 51 to 53, Table 3 and FIG. 71 and described below. In addition, Anton Paar's Abbemat was used to measure the refractive index of OPV1. The measurement results are shown also in Table 3.

Example 4

In Example 4, the OPV2 was synthesized.

Since Example 3 was repeated except for using a swallowtail alkyl chain $C_8H_{12}$ as an R in the ether compound 730 in the synthesis of OPV1 of Example 3 described with referring to FIG. 8, the description is omitted. As a result, a pale yellow liquid was obtained.

Similarly to Example 3, the resultant pale yellow liquid was confirmed to be OPV2 by $^1$H NMR, MALDI-TOF-MS and UV/vis. Also, OPV2 was subjected, similarly to Example 3, to the absolute fluorescence quantum yield measurement, the measurement of the frequency dependency of the storage modulus G', the loss modulus G'' and the complex viscosity η*, the differential scanning calorimetry, the glass transition temperature measurement, the absorption spectrum measurement, the emission spectrum measurement by the ultraviolet light irradiation (excitation wavelength 365 nm), the photoconductivity measurement and the refractive index measurement. The results are shown in Table 1, FIGS. 31, 32, 42, Table 2, FIGS. 54, 55 and Table 3 and described below.

Figure 72:
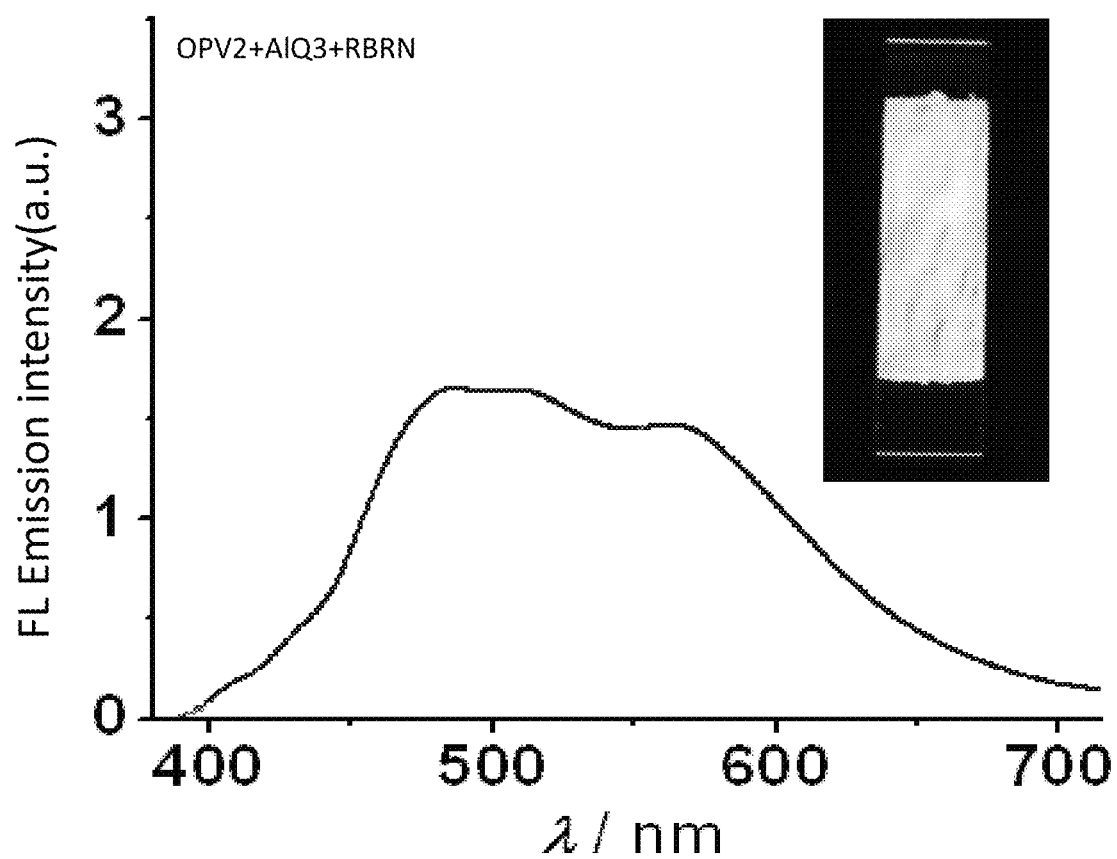
FIG. 72 shows the luminescent spectrum of a white light luminescence using OPV2 according to Example 4 and the luminescent state.

In addition, application of OPV2 to a white lighting apparatus was investigated. A blue luminescent OPV2, a green luminescent tris(8-oxoquinoline)aluminum (III) (AlQ$_3$) and a red luminescent 5,6,11,12-tetraphenyltetracene (rubrene) were mixed at 1:1.65:0.25 (molar ratio). This mixture was coated on a quartz substrate to form a film, which was subjected to the ultraviolet light irradiation (excitation wavelength 365 nm), and its luminescent state and the emission spectrum were measured. The results are shown in FIG. 72.

Example 5

In Example 5, the OPV3 was synthesized.

Figure 9:
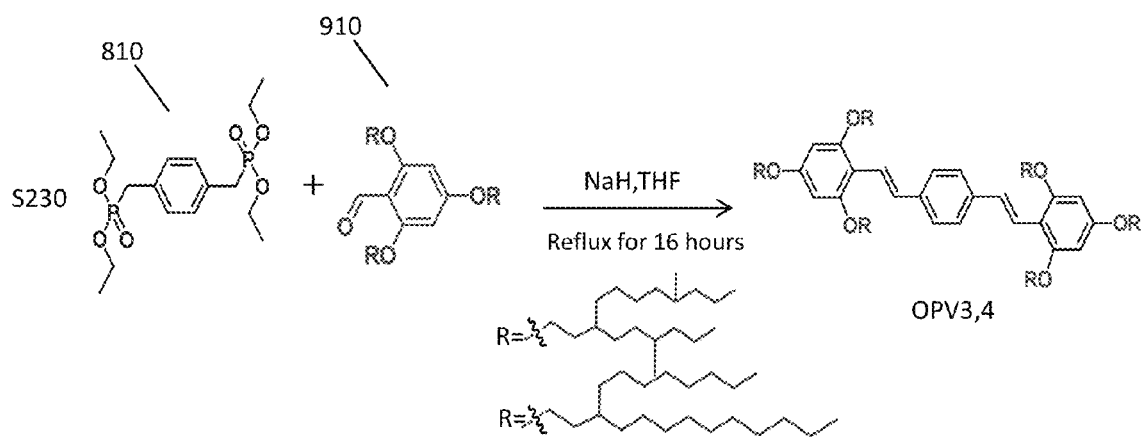
FIG. 9 shows an illustration of the manufacture process for synthesizing OPV3 and OPV4 of Examples 5 and 6.

FIG. 9 shows an illustration of the manufacture process for synthesizing OPV3 and OPV4 of Examples 5 and 6.

Except for replacing the ether compound 730 of 3,5-substituted benzaldehyde with the ether compound 910 of 2,4,6-substituted benzaldehyde ((2,4,6)F180N benzaldehyde), Examples 3 and 4 were followed. To a solution of the ether compound 910 of 2,4,6-substituted benzaldehyde (1.59 g, 1.74 mmol) and tetraethyl-1,4-phenylenebis(methylene)diphosphonate 810 (0.3 g, 0.79 mmol), THF (30 ml) and potassium t-butoxide (0.58 g, 5.22 mmol) were added under an argon atmosphere. As an R of the ether compound 910, a hyperbranch alkyl chain F180N (isostearyl group) was employed. This solution mixture was refluxed for 16 hours and the solvent was removed under reduced pressure (Step S230). The residue was extracted with chloroform, and washed several times with brine and water. The organic layer was evaporated under reduced pressure, and a silica gel column chromatography (n-hexane/chloroform, 3:1) was conducted to obtain a pale yellow liquid (1.5 g, yield: 51%).

The resultant pale yellow liquid thus obtained was confirmed to be OPV3 by $^1$H NMR, MALDI-TOF-MS and UV/vis.

$^1$H NMR (400 MHz, CDCl$_3$): δ=0.82-0.96 (m, 72H, CH$_3$), 1.04-1.18 (m, 12H, (CH$_3$)CH(CH$_2$)$_2$), 1.19-1.42 (m, 120H, CH$_2$), 1.82 (m, 6H, CH(CH$_2$)$_3$), 3.89 (m, 12H, OCH$_2$), 6.12 (S, 4H, ArH), 7.38 (m, 4H, vinylic), 7.50 (m, 4H, Ar)

MALDI-TOF-MS (matrix:dithranol):$C_{130}H_{232}O_6$: Calculated: 1891.80. Found: 1891.01[M$^+$]

UV-vis (dichloromethane): $\lambda_{max}$=386 nm, $\epsilon$=57432M$^{-1}$ cm$^{-1}$ Similarly to Example 3, OPV3 was subjected to the absolute fluorescence quantum yield measurement, the measurement of the frequency dependency of the storage modulus G', the loss modulus G'' and the complex viscosity η*, the differential scanning calorimetry, the glass transition temperature measurement, the absorption spectrum measurement, the emission spectrum measurement by the ultraviolet light irradiation (excitation wavelength 365 nm), the photoconductivity measurement and the refractive index measurement. The results are shown in Table 1, FIGS. 29 to 32, 43, Table 2, FIGS. 56, 57 and Table 3 and described below.

Example 6

In Example 6, the OPV4 was synthesized.

Since Example 5 was repeated except for using a swallowtail alkyl chain $C_8H_{12}$ as an R in the ether compound 910 in the synthesis of OPV3 of Example 5 described with referring to FIG. 9, the description is omitted.

Similarly to Example 4, OPV4 was subjected to the absolute fluorescence quantum yield measurement, the measurement of the frequency dependency of the storage modulus G', the loss modulus G'' and the complex viscosity η*, the differential scanning calorimetry, the glass transition temperature measurement, the absorption spectrum measurement, the observation of luminescence upon the ultraviolet light irradiation (excitation wavelength 365 nm), the emission spectrum measurement, the photoconductivity measurement, the refractive index measurement, and an investigation for application to a white lighting apparatus. The results are shown in Table 1, FIGS. 31, 32, 44, Table 2, FIGS. 58, 59, Table 3 and FIG. 73 and described below. For the application to the white lighting apparatus, a mixture of OPV4 and AlQ$_3$ and rubrene at 1:1.65:0.24 (molar ratio)) was employed.

Figure 74:
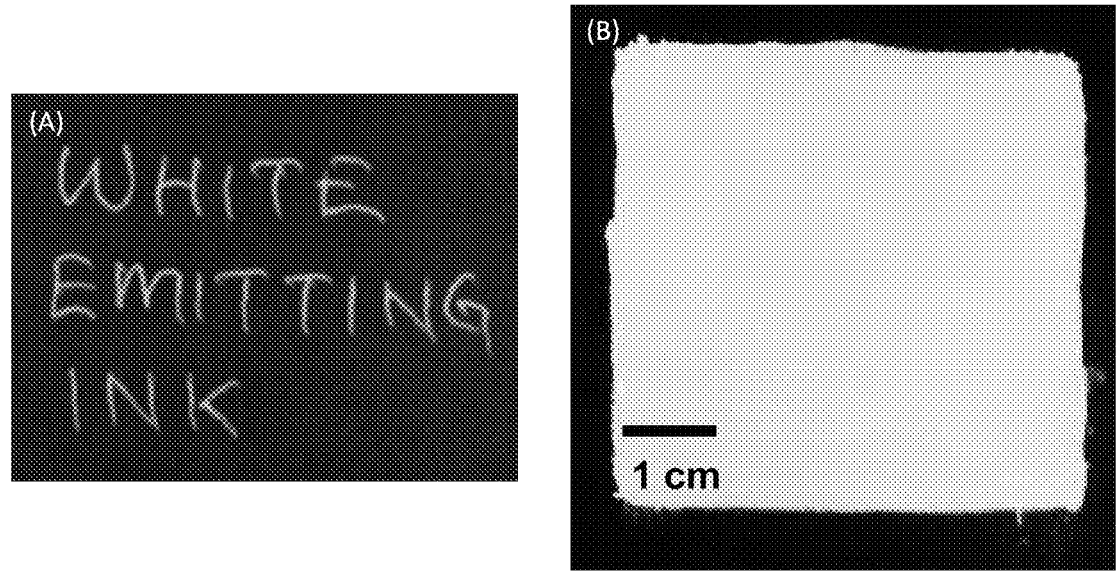
FIG. 74 shows the luminescent state of the white luminescent ink using OPV4 according to Example 6.

The application of OPV4 also to a novel ink material (white luminescent ink) was investigated. A mixture of OPV4 and AlQ$_3$ and rubrene (1:1.65:0.24 (molar ratio)) obtained as described above was filled as an ball-point pen ink material, and letters were written. These letters were subjected to the ultraviolet light irradiation (excitation wavelength 365 nm), and their luminescent state were observed. A brush (a writing brush) was employed to paint a 5 cm-square area with the mixture. The paint was subjected to the ultraviolet light irradiation (excitation wavelength 365 nm) and its luminescent state was observed. The results are shown in FIG. 74.

Example 7

In Example 7, the ACN1 was synthesized.

Figure 10:
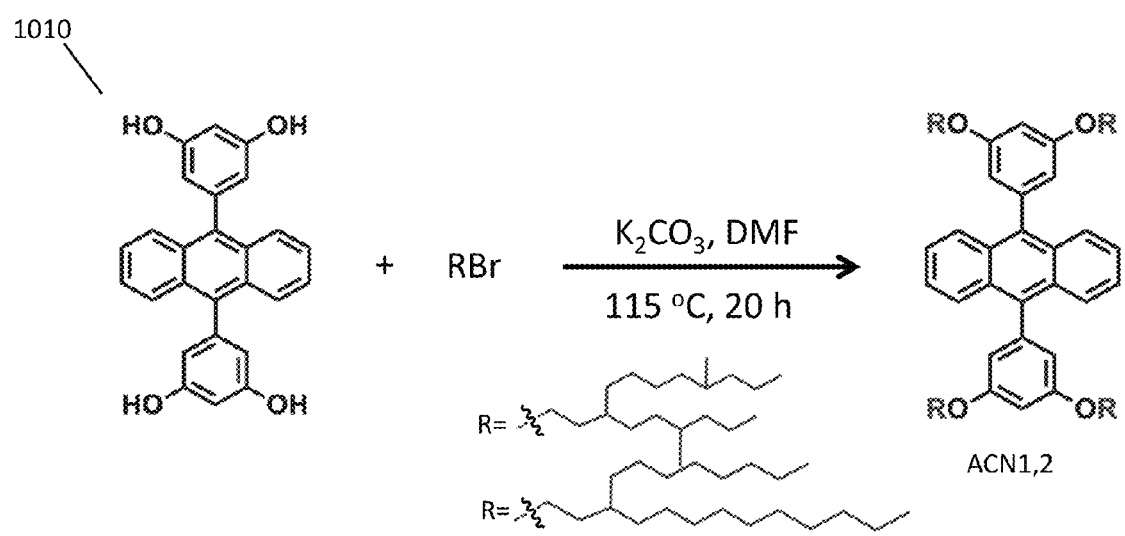
FIG. 10 shows an illustration of the manufacture process for synthesizing ACN1 and ACN2 of Examples 7 and 8.

FIG. 10 shows an illustration of the manufacture process for synthesizing ACN1 and ACN2 of Example 7 and 8.

To a solution of 9,10-bis(3,5-dihydroxyphenyl)anthracene 1010 (1.0 g, 2.5 mmol) and a brominated branched alkyl RBr (4.2 g, 12.6 mmol), N,N-dimethylformamide (DMF) (20 ml) and potassium carbonate (2.8 g, 20 mmol), potassium iodide (160 mg, catalytic amount) were added. As a brominated branched alkyl RBr, F180N (isostearyl group)

having an R which was a hyperbranch alkyl chain was employed. This solution mixture was reacted at 115° C. for 20 hours, and the solvent was removed. The residue was extracted with chloroform, and washed several times with brine and water. The organic layer was evaporated under reduced pressure, and a silica gel column chromatography (n-hexane/chloroform, 3:1) was conducted to obtain an yellow liquid (2.5 g, yield: 71%).

Similarly to Example 3, ACN1 was subjected to the absolute fluorescence quantum yield measurement, appearance observation, the measurement of the frequency dependency of the storage modulus G', the loss modulus G" and the complex viscosity η*, the absorption spectrum measurement, the emission spectrum measurement by the ultraviolet light irradiation (excitation wavelength 365 nm), the photoconductivity measurement and the refractive index measurement. The results are shown in Table 1, FIGS. 18, 33, 34, 60, 61 and Table 3 and described below.

Example 8

In Example 8, the ACN2 was synthesized.

Since Example 7 was repeated except for using $C_8H_{12}$ having an R which is a swallowtail alkyl chain as a brominated branched alkyl RBr in the synthesis of ACN1 of Example 7 described with referring to FIG. 10, the description is omitted.

Similarly to Example 7, ACN2 was subjected to the absolute fluorescence quantum yield measurement, the measurement of the frequency dependency of the storage modulus G', the loss modulus G" and the complex viscosity η*, the absorption spectrum measurement, the emission spectrum measurement by the ultraviolet light irradiation (excitation wavelength 365 nm), the photoconductivity measurement and the refractive index measurement. The results are shown in Table 1, FIGS. 33, 34, 62, 63 and Table 3 and described below.

Example 9

In Example 9, the FL1 was synthesized.

Figure 11:
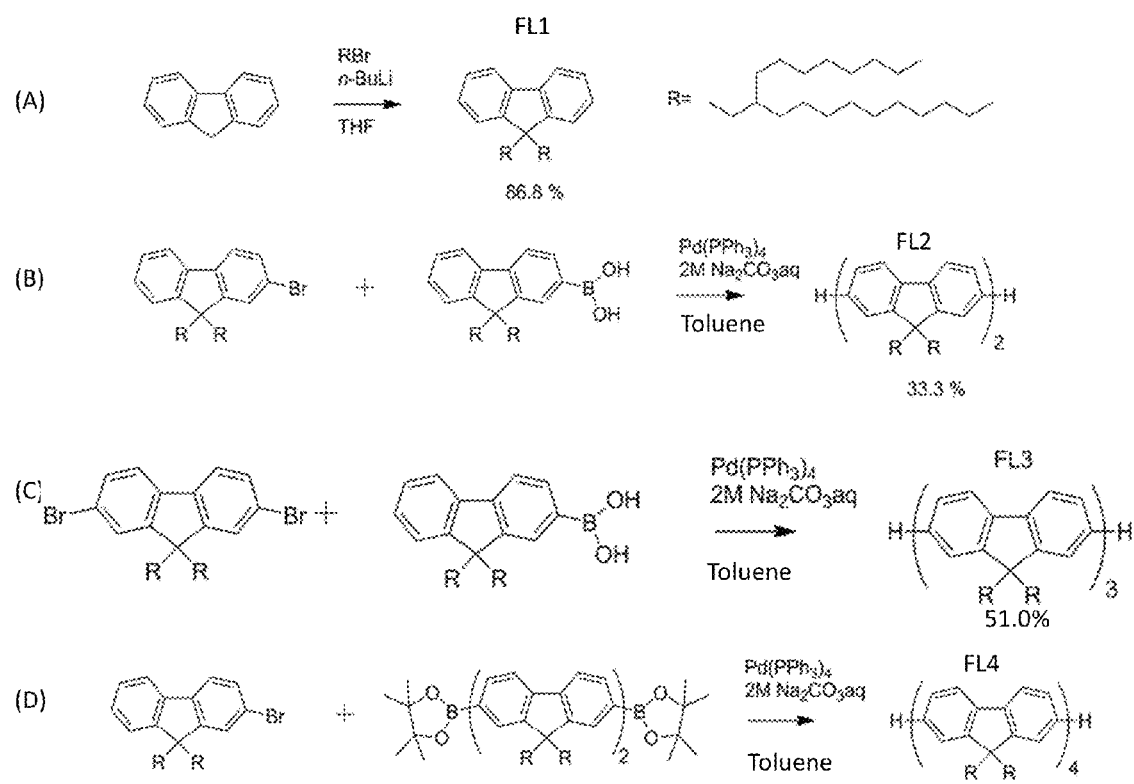
FIG. 11 shows an illustration of the manufacture processes for synthesizing FL1 to FL4 of Examples 9 to 12.

FIG. 11 shows an illustration of the manufacture process for synthesizing FL1 to FL4 of Examples 9 to 12.

According to FIG. 11(A), a solution of fluorene (0.25 g, 1.51 mmol) in 6 ml of tetrahydrofuran (THF) was cooled to −78° C., combined with n-butyllitium (2 ml, 2.5 mol), and then, after 1 hour, reacted with a brominated branched alkyl RBr (1.36 g, 3.97 mmol). As a brominated branched alkyl RBr, $C_{12}C_8$ whose R was a swallowtail alkyl chain was employed. This solution mixture was warmed gradually from −78° C. to room temperature and reacted for 12 hours. Dichloromethane and water were employed for partitioning, the organic phase was extracted, the solution was dried over sodium sulfate and thereafter the solvent was removed under reduced pressure. A silica gel column chromatography (n-hexane) was conducted to obtain a colorless transparent liquid (1.01 g, yield: 86.8%).

The colorless transparent liquid thus obtained was subjected to $^1$H NMR spectroscopy and MALDI-TOF-MS. Based on MALDI TOF MS, the measured value of the molecular weight (726.5) was revealed to be in a satisfactory agreement with the value calculated from FL1 nominal formula $C_{53}H_{90}$ (726.7).

Figure 12:
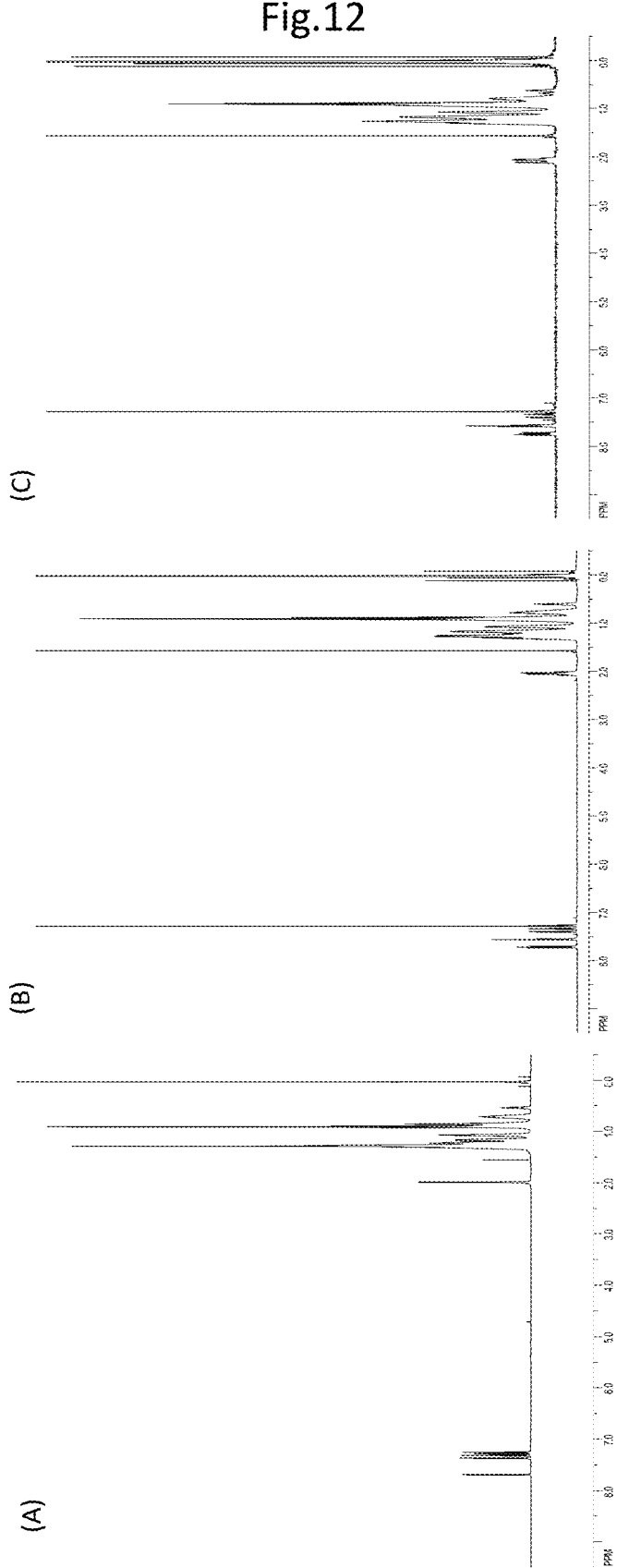
FIG. 12 shows the NMR spectra of FL1 to FL3 of Examples 9 to 11.

FIG. 12 shows the NMR spectrum of FL1 to FL3 of Examples 9 to 11.

FIG. 12(A) shows the NMR spectrum of FL1. Based on the NMR spectrum, the colorless transparent liquid obtained was confirmed to be FL1.

Similarly to Example 3, FL1 was subjected to the absolute fluorescence quantum yield measurement, the differential scanning calorimetry, the glass transition temperature measurement, the absorption spectrum measurement, the photoconductivity measurement and the refractive index measurement. The results are shown in Table 1, FIG. 45, Table 2, FIG. 64 and Table 3, respectively, and described below.

Example 10

In Example 10, the FL2 was synthesized.

Again, FIG. 11 is referred to. According to FIG. 11(B), a brominated FL1 (2.09 g, 2.6 mmol) and a fluorene substituted with boronic acid at its one end (2.0 g, 2.6 mmol) was reacted for 48 hours at 85° C. in a solvent mixture of 10 mL of $Na_2CO_3$ aqueous solution (2M) and 15 ml of toluene in the presence of tetrakis(triphenylphosphine)palladium (Pd (PPh$_3$)$_4$) (50 mg, 0.043 mmol). Dichloromethane and water were employed for partitioning, and the organic phase was extracted from the reaction mixture and then dried over sodium sulfate and thereafter the solvent was evaporated under reduced pressure. A silica gel column chromatography (n-hexane) was conducted followed by purification by HPLC (chloroform) to yield a pale yellow transparent liquid (1.26 g, yield: 33.3%).

The pale yellow transparent liquid thus obtained was confirmed to be FL2 by $^1$H NMR spectroscopy (FIG. 12(B)) and MALDI-TOF-MS. Based on MALDI TOF MS, the measured value of the molecular weight (1452.0) was revealed to be in a satisfactory agreement with the value calculated from FL2 nominal formula $C_{106}H_{178}$ (1451.39).

Similarly to Example 9, FL2 was subjected to the absolute fluorescence quantum yield measurement, the differential scanning calorimetry, the glass transition temperature measurement, the absorption spectrum measurement, the photoconductivity measurement and the refractive index measurement. The results are shown in Table 1, FIG. 45, Table 2, FIG. 65 and Table 3 and described below.

Example 11

In Example 11, the FL3 was synthesized.

Again, FIG. 11 is referred to. According to FIG. 11(C), dibromofluorene (0.5 g, 0.57 mmol) and a fluorene substituted with boronic acid at its one end (1.0 g, 1.3 mmol) were reacted for 96 hours (4 days) at 85° C. in the solvent mixture of 6 ml of $Na_2CO_3$ aqueous solution (2M) and 10 ml of toluene in the presence of tetrakis(triphenylphosphine)palladium (Pd(PPh$_3$)$_4$) (50 mg, 0.043 mmol). Dichloromethane and water were employed for partitioning, and the organic phase was extracted from the reaction mixture and then dried over sodium sulfate and thereafter the solvent was evaporated under reduced pressure. A silica gel column chromatography (n-hexane) was conducted followed by purification by HPLC (chloroform) to yield a pale yellow transparent liquid (630 mg, yield: 51.0%).

The pale yellow transparent liquid thus obtained was confirmed to be FL3 by $^1$H NMR spectroscopy (FIG. 12(C)) and MALDI-TOF-MS. Based on MALDI TOF MS, the measured value of the molecular weight (2176.5) was revealed to be in a satisfactory agreement with the value calculated from FL32 nominal formula $C_{159}H_{266}$ (2176.08).

Similarly to Example 9, FL3 was subjected to the absolute fluorescence quantum yield measurement, the differential scanning calorimetry, the glass transition temperature measurement, the absorption spectrum measurement, the photoconductivity measurement and the refractive index measurement. The results are shown in Table 1, FIG. 45, Table 2, FIG. 66 and Table 3 and described below.

Example 12

Figure 45:
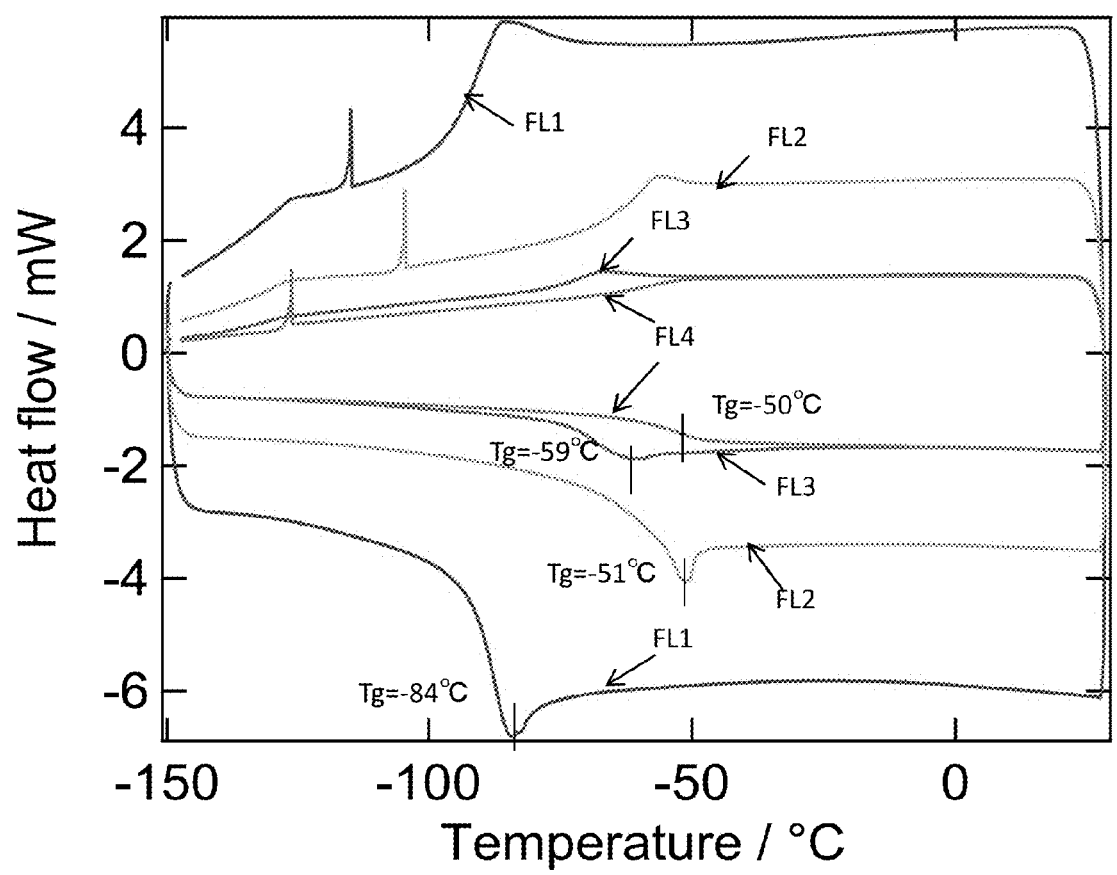
FIG. 45 shows an illustration of the results of the differential scanning calorimetry of FL1 to 4 according to Examples 9 to 12.

In Example 12, the FL4 was synthesized.
Again, FIG. 11 is referred to. According to FIG. 11(D), a brominated FL1 (2.0 g, 2.48 mmol) and a fluorene dimer substituted with boronic acid at its both ends (1.0 g, 0.587 mmol) were reacted for 72 hours (3 days) at 85° C. in a solution mixture of 12 ml of $Na_2CO_3$ aqueous solution (2M) and 20 ml of toluene in the presence of tetrakis(triphenylphosphine)palladium ($Pd(PPh_3)_4$) (100 mg, 0.087 mmol). Dichloromethane and water were employed for partitioning, the organic phase was extracted from the reaction mixture, dried over sodium sulfate and thereafter the solvent was evaporated under reduced pressure. A silica gel column chromatography (n-hexane) was conducted followed by purification by HPLC (chloroform) to yield a pale yellow transparent liquid (130 mg, yield: 7.6%).
The pale yellow transparent liquid thus obtained was confirmed to be FL4 by $^1H$ NMR spectroscopy and MALDI-TOF-MS. Also, FL4 was subjected to the differential scanning calorimetry and the glass transition temperature measurement. The results are shown in FIG. 45 and Table 2 and described below.

Example 13

Figure 13:
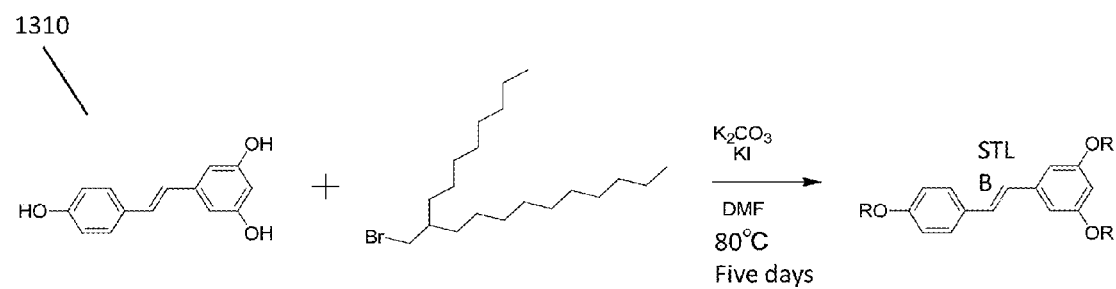
FIG. 13 shows an illustration of the manufacture process for synthesizing STLB of Example 13.
Figure 14:
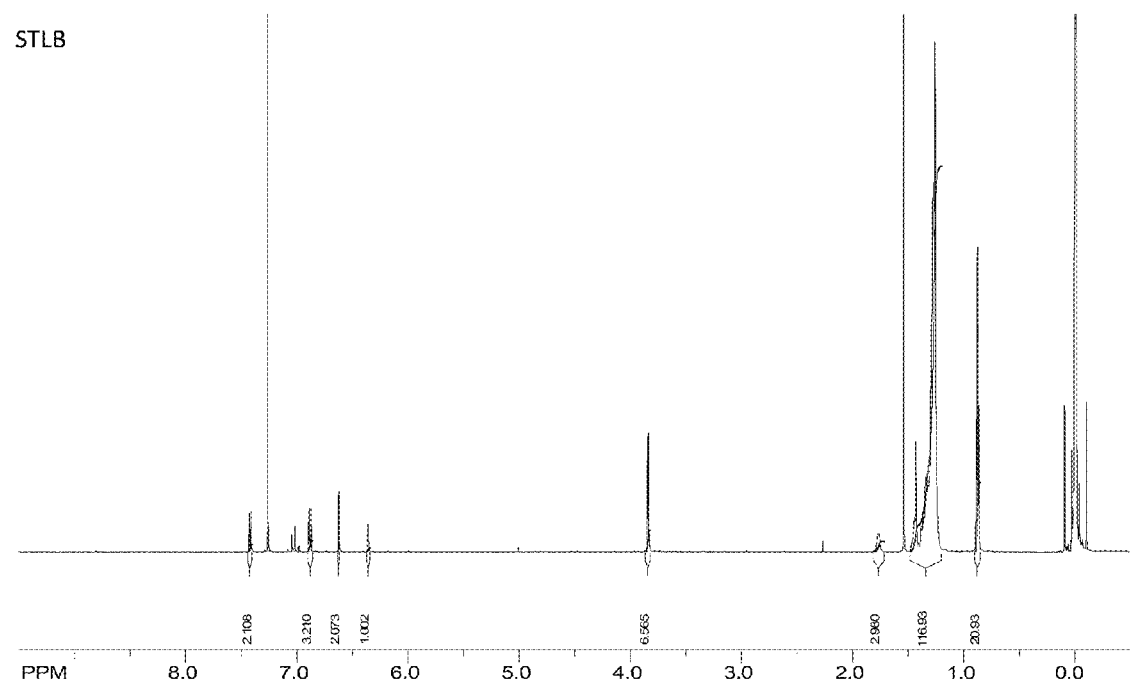
FIG. 14 shows the NMR spectrum of STLB of Example 13.

In Example 13, the STLB was synthesized.
FIG. 13 shows an illustration of the manufacture process for synthesizing STLB of Example 13.
Resveratrol 1310 (350 mg, 1.53 mmol) and a brominated branched alkyl RBr (4.0 g, 11.1 mmol) were reacted for 120 hours (5 days) at 85° C. in DMF (10 ml) in the presence of potassium carbonate (5.0 g, 36.2 mmol) and potassium iodide (0.5 g, 3.01 mmol). Chloroform and water were employed for partitioning, the organic phase was extracted from the reaction mixture, dried over sodium sulfate and thereafter the solvent was evaporated under reduced pressure. A silica gel column chromatography (n-hexane followed by n-hexane/chloroform, 2:1) was employed for purification, and a colorless transparent liquid was obtained (1.26 g, yield: 77.1%).
FIG. 14 shows the NMR spectrum of STLB of Example 13.
The colorless transparent liquid thus obtained was confirmed to be STLB by $^1H$ NMR spectroscopy.
Similarly to Example 3, STLB was subjected to the appearance observation, the measurement of the frequency dependency of the storage modulus G', the loss modulus G" and the complex viscosity $\eta^*$, and the measurement of the absorption spectrum measurement and the refractive index. The results are shown in FIGS. 19, 35, 36, 67 and Table 3 and described below.

Example 14

Figure 15:
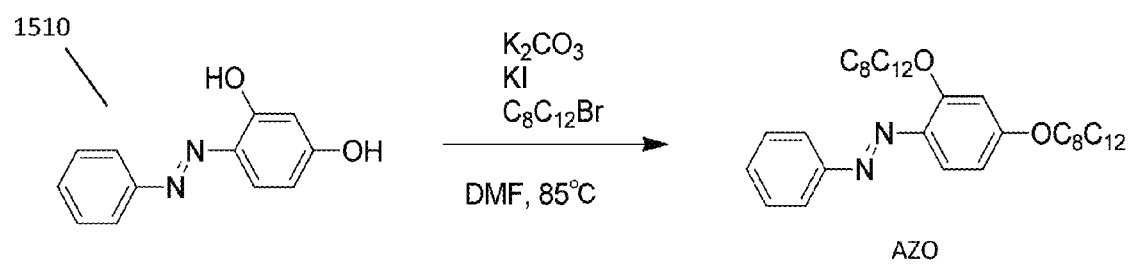
FIG. 15 shows an illustration of the manufacture process for synthesizing of AZO of Example 14.
Figure 20:
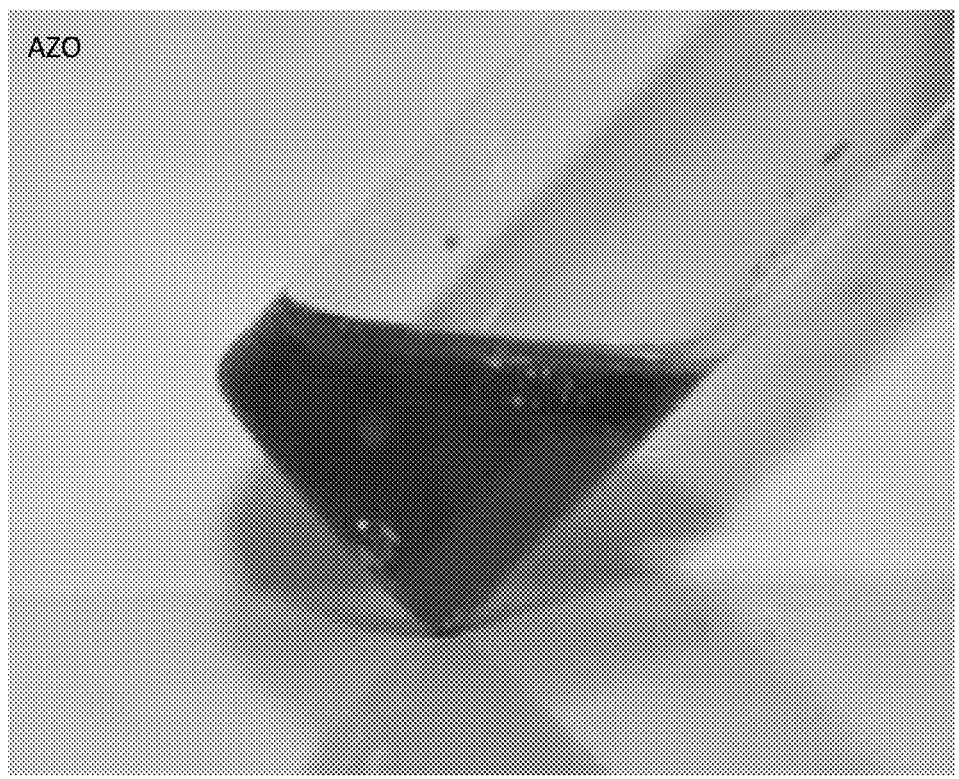
FIG. 20 is an image showing the state of AZO under a visible light according to Example 14.
Figure 68:
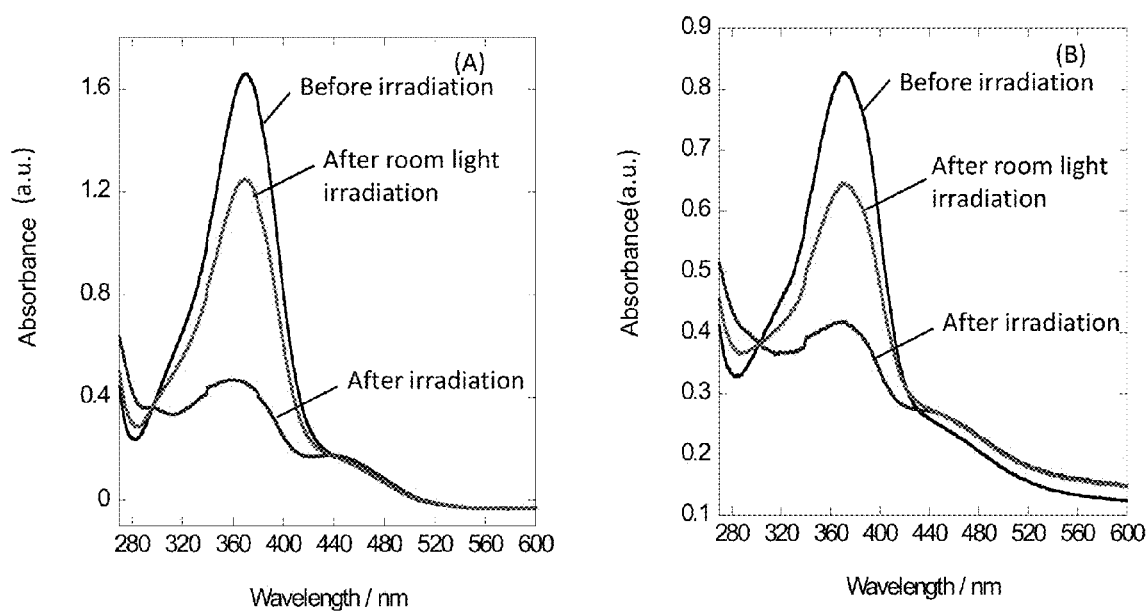
FIG. 68 shows an absorption spectrum of AZO according to Example 14.

In Example 14, the AZO was synthesized.
FIG. 15 shows an illustration of the manufacture process for synthesizing of AZO of Example 14.
2,4-dihydroxyazobenzene 1510 (0.5 g, 2.33 mmol) was reacted for 24 hours at 85° C. in DMF (5 ml) in the presence of a brominated branched alkyl RBr (2.0 g, 5.54 mmol) and calcium carbonate (2.0 g, 14.5 mmol) and potassium iodide (0.2 g, 1.2 mmol). As a brominated branched alkyl RBr, $C_8C_{12}$ whose R was a swallowtail alkyl chain was employed. Chloroform and water were employed for partitioning, the organic phase was extracted from the reaction mixture, then dried over sodium sulfate and thereafter the solvent was evaporated under reduced pressure. A silica gel column chromatography (n-hexane) was employed for purification, and a red tan liquid was obtained (1.26 g, yield: 70.6%). The red tan liquid thus obtained was confirmed to be AZO by $^1H$ NMR spectroscopy.
Similarly to Example 3, AZO was subjected to the appearance observation, the measurement of the absorption spectrum and the refractive index. The results are shown in FIGS. 20, 68 and Table 3 and described below.
The results of the observation and the measurement of Examples 1 to 14 described above are detailed below. For convenience, the experiment conditions and the absolute yield ($\phi$) of Examples 1 to 14 are shown in Table 1.

TABLE 1

Experimental condition of Examples 1 to 14 and Absolute fluorescence quantum yield ($\phi$)

| Example | Sample name | π-conjugated molecule | Side chain | Substituent S | Absolute fluorescence quantum yield ($\phi$) |
|---|---|---|---|---|---|
| 1 | P1 | Porphyrin | Isostearyl group (F180N) | — | 0.016 |
| 2 | P2 | Porphyrin | Isostearyl group (F180N) | Ether | 0.031 |
| 3 | OPV1 | Oligo(p-)phenylene vinylene | Isostearyl group (F180N) | Ether | 0.45 |
| 4 | OPV2 | Oligo(p-)phenylene vinylene | $C_{12}C_8$ | Ether | 0.46 |
| 5 | OPV3 | Oligo(p-)phenylene vinylene | Isostearyl group (F180N) | Ether | 0.47 |
| 6 | OPV4 | Oligo(p-)phenylene vinylene | $C_{12}C_8$ | Ether | 0.48 |
| 7 | ACN1 | Anthracene | Isostearyl group (F180N) | Ether | 0.61 |
| 8 | ACN2 | Anthracene | $C_{12}C_8$ | Ether | 0.65 |
| 9 | FL1 | Fluorene (n = 1) | $C_{12}C_8$ | — | 0.21 |
| 10 | FL2 | Fluorene (n = 2) | $C_{12}C_8$ | — | 0.71 |

TABLE 1-continued

Experimental condition of Examples 1 to 14 and Absolute fluorescence quantum yield ($\phi$)

| Example | Sample name | π-conjugated molecule | Side chain | Substituent S | Absolute fluorescence quantum yield ($\phi$) |
|---|---|---|---|---|---|
| 11 | FL3 | Fluorene (n = 3) | $C_{12}C_8$ | — | 0.73 |
| 12 | FL4 | Fluorene (n = 4) | $C_{12}C_8$ | — | — |
| 13 | STLB | Stilbene | $C_{12}C_8$ | Ether | — |
| 14 | AZO | Azobenzene | $C_{12}C_8$ | Ether | — |

FIG. 16 is an image showing the state of P1 under a visible light according to Example 1.

FIG. 16 shows that P1 is a liquid having a purple color under the visible light at room temperature. In addition, although the figure is not shown, P2 of Example 2 was confirmed similarly to be a liquid having a purple color under the visible light.

In addition, the density of porphyrin as a π-conjugated molecule of P1 and P2 was calculated. The density of P1 and P2 were 24.5 and 11.2, respectively. The value especially of P1 was greater, for example, than the density of a liquid form porphyrin derivative of Example 1 of Patent Literature 1 (5,10,15,20-tetrakis[3,4,5-tris(heptyloxy)phenyl]porphyrin) (20.3). Accordingly, it was confirmed that the higher density of the π-conjugated molecule in the liquid-form organic material of the invention can be achieved by using a certain side chain.

FIG. 17 is an image showing the state of OPV1 under a visible light according to Example 3.

FIG. 17 shows that OPV1 is a liquid having a pale yellow color under the visible light at room temperature. In addition, although the figure is not shown, OPV2 to 4 of Examples 4 to 6 were confirmed similarly to be liquids having a pale yellow color under the visible light.

Figure 18:
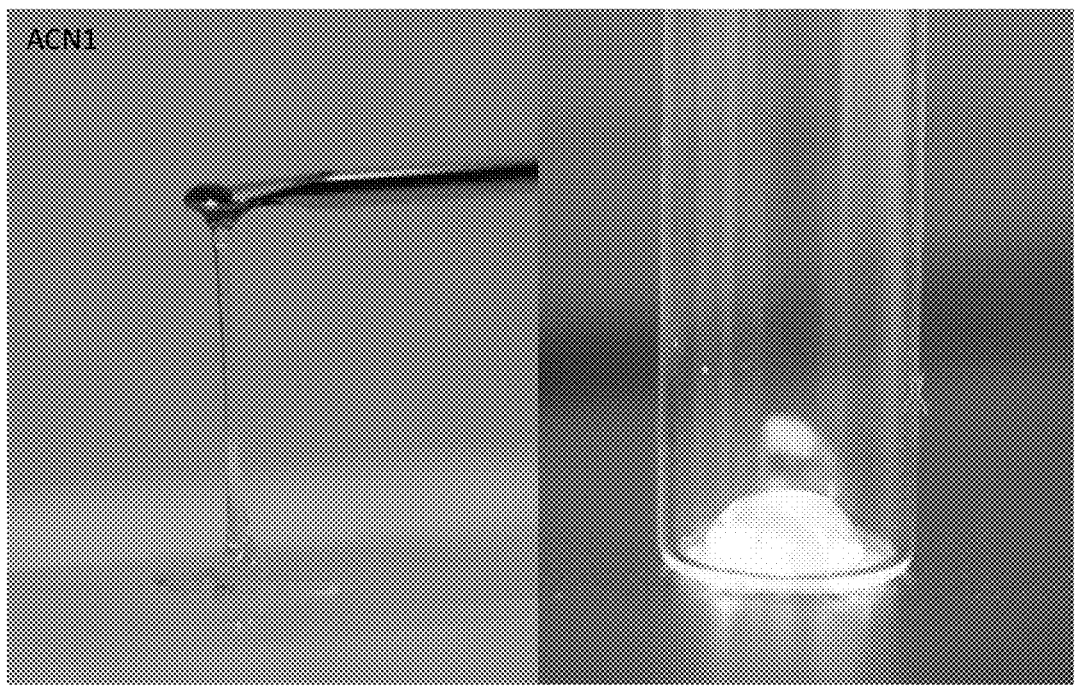
FIG. 18 is an image showing the state of ACN1 under a visible light and under a UV light according to Example 7.

FIG. 18 is an image showing the state of ACN1 under a visible light according to Example 7.

According to FIG. 18, ACN1 is found to be a liquid having a yellow color under the visible light at room temperature. In addition, although the figure is not shown, ACN2 of Example 8 was confirmed similarly to be a liquid having a pale yellow color under the visible light.

Figure 19:
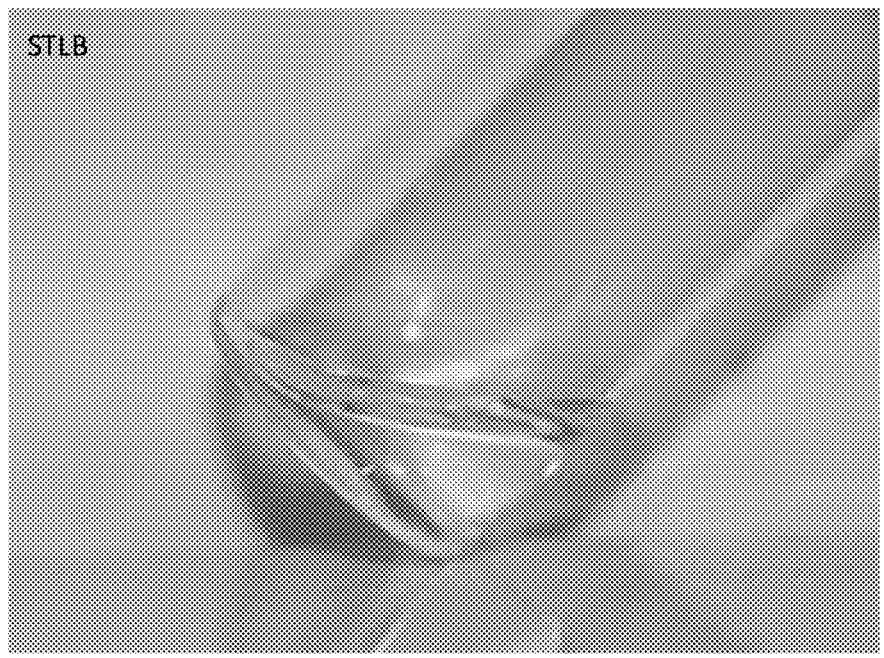
FIG. 19 is an image showing the state of STLB under a visible light according to Example 13.

FIG. 19 is an image showing the state of STLB under a visible light according to Example 13.

According to FIG. 19, STLB is found to be a colorless transparent liquid at room temperature.

FIG. 20 is an image showing the state of AZO under a visible light according to Example 14.

According to FIG. 20, AZO is found to be a liquid having a red tan color at room temperature.

According to FIG. 16 to FIG. 20, the ambient temperature liquid-form organic material of the present invention is found to be in a liquid form at ambient temperature. It was also confirmed that depending on the selected π-conjugated molecule a different pigment (color development) is achieved, thereby being possible to become an ink material.

Table 1 is referred to. Table 1 shows the absolute fluorescence quantum yield of each sample in Examples 1 to 11. Based on the values in Table 1, the ambient temperature liquid-form organic material of the present invention is found to be a luminescent material. For example, the fluorescence quantum yields of OPV1 to 4 are comparable to that of an existing material known as luminescent material. These results show that the ambient temperature liquid-form organic material according to the present invention is in a state where the π-conjugated molecule attributable to the color development is in an effectively dispersed state, indicating no potent interaction between the π-conjugated molecules.

In addition, Table 1 shows that the fluorescence quantum yield of P2 is greater than that of P1. Similarly, the fluorescence quantum yields of FL2 and FL3 are greater than that of FL1. This means that the degree of the steric inhibition of the π-π interaction in the π-conjugated molecule can be adjusted depending on the selection of the number or type of the side chain to be introduced in the conjugated molecule, thereby keeping the excitation state for a prolonged period.

Figure 21:
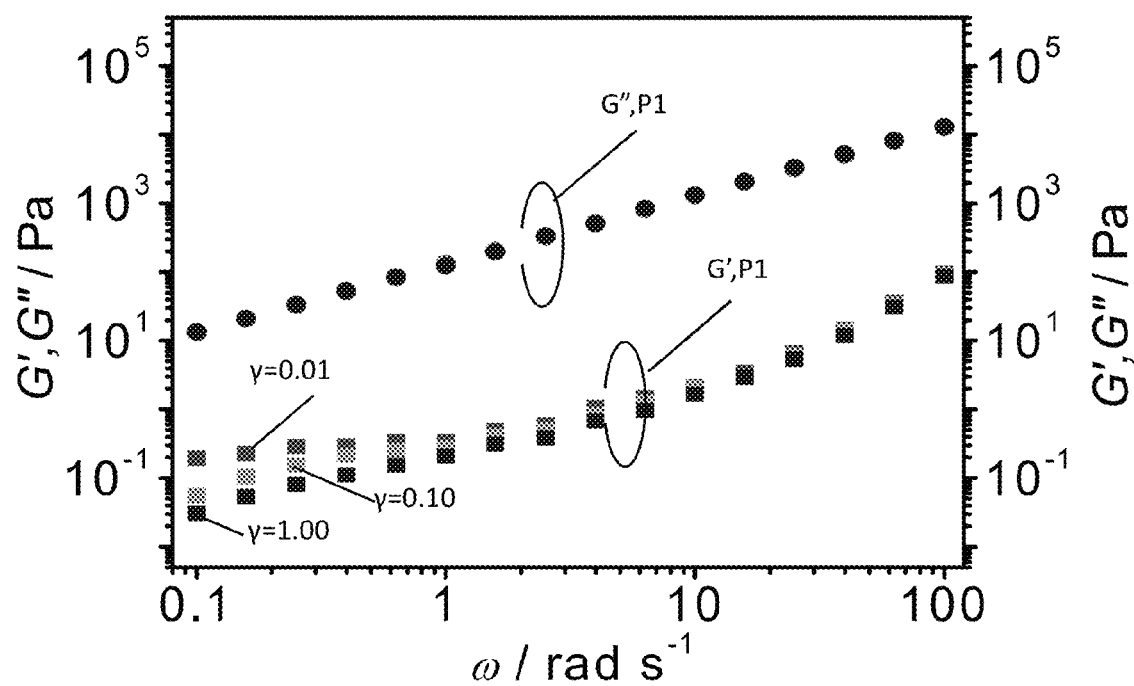
FIG. 21 shows an illustration of the frequency dependency of the storage elastic modulus G' and the loss elastic modulus G" of P1 according to Example 1 at each shear force ($\gamma=0.01$, 0.10 and 1.00).

FIG. 21 shows an illustration of the frequency dependency of the storage modulus G' and the loss modulus G" of P1 according to Example 1 at each shear force (γ=0.01, 0.10 and 1.00).

Figure 22:
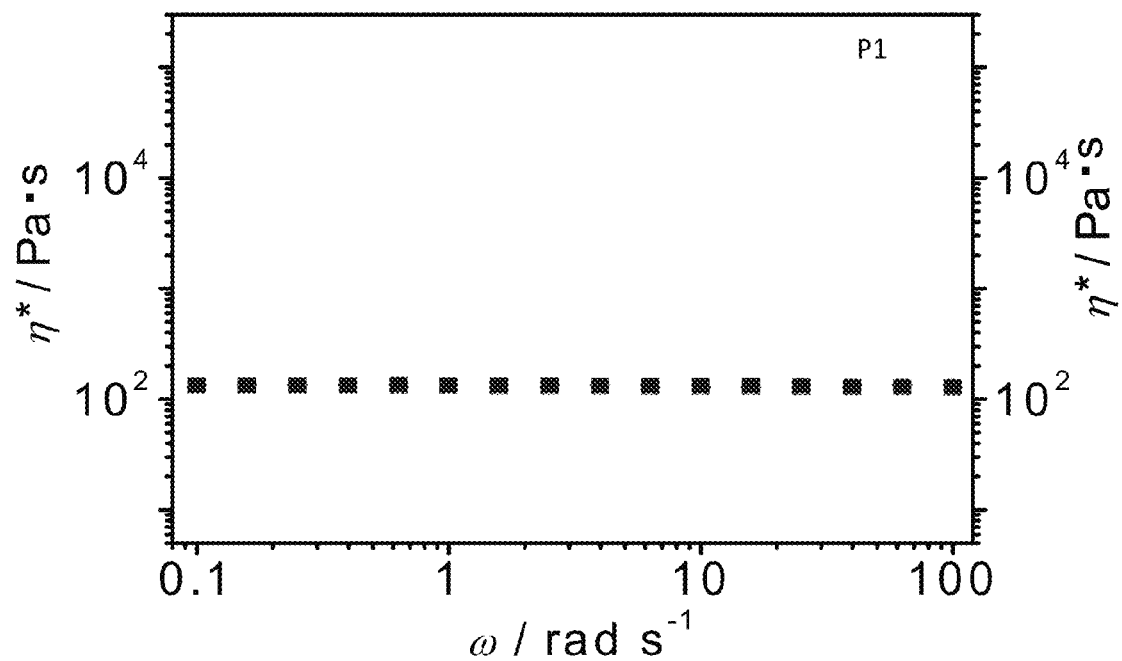
FIG. 22 shows an illustration of the frequency dependency of the complex viscosity $\eta^*$ of P1 according to Example 1 at each shear force ($\gamma=0.01$, 0.10 and 1.00).

FIG. 22 shows an illustration of the frequency dependency of the complex viscosity η* of P1 according to Example 1 at each shear force (γ=0.01, 0.10 and 1.00).

Figure 23:
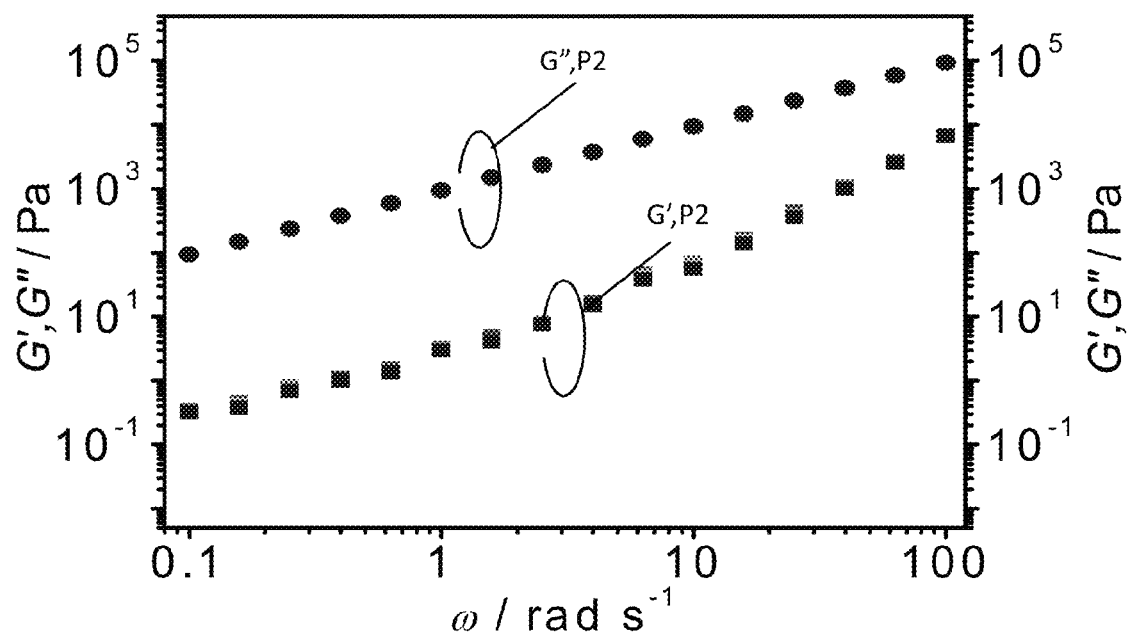
FIG. 23 shows an illustration of the frequency dependency of the storage modulus G' and the loss modulus G" of P2 according to Example 2 at each shear force ($\gamma=0.01$, 0.10 and 1.00).

FIG. 23 shows an illustration of the frequency dependency of the storage modulus G' and the loss modulus G" of P2 according to Example 2 at each shear force (γ=0.01, 0.10 and 1.00).

Figure 24:
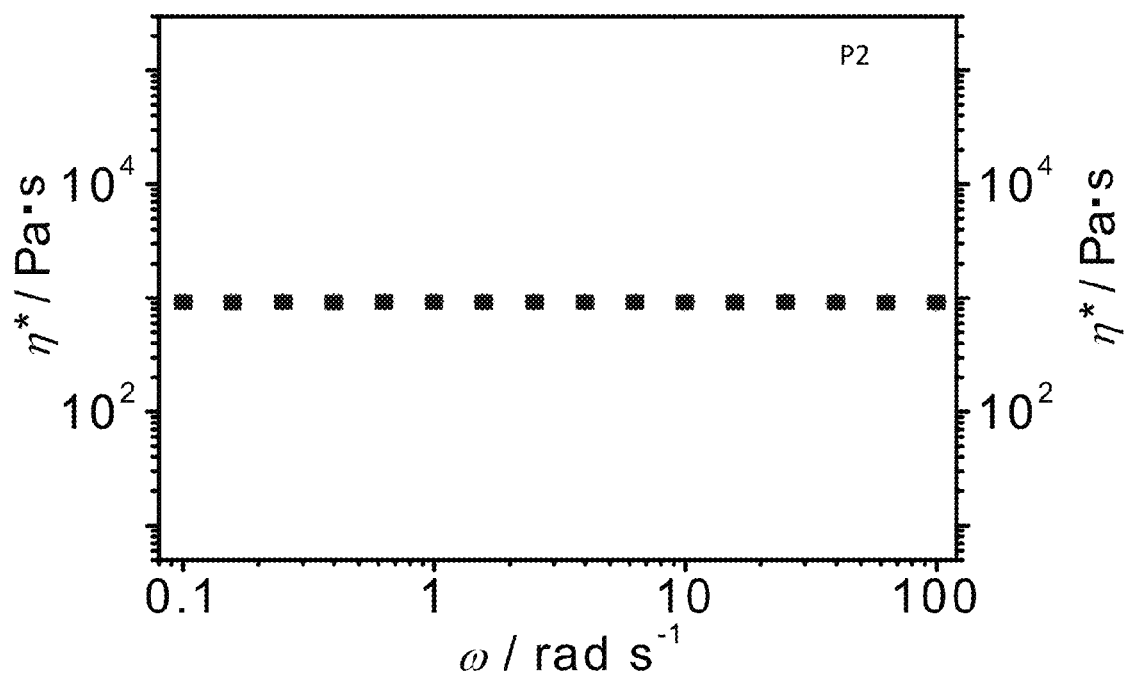
FIG. 24 shows an illustration of the frequency dependency of the complex viscosity $\eta^*$ of P2 according to Example 2 at each shear force ($\gamma=0.01$, 0.10 and 1.00).

FIG. 24 shows an illustration of the frequency dependency of the complex viscosity η* of P2 according to Example 2 at each shear force (γ=0.01, 0.10 and 1.00).

Figure 25:
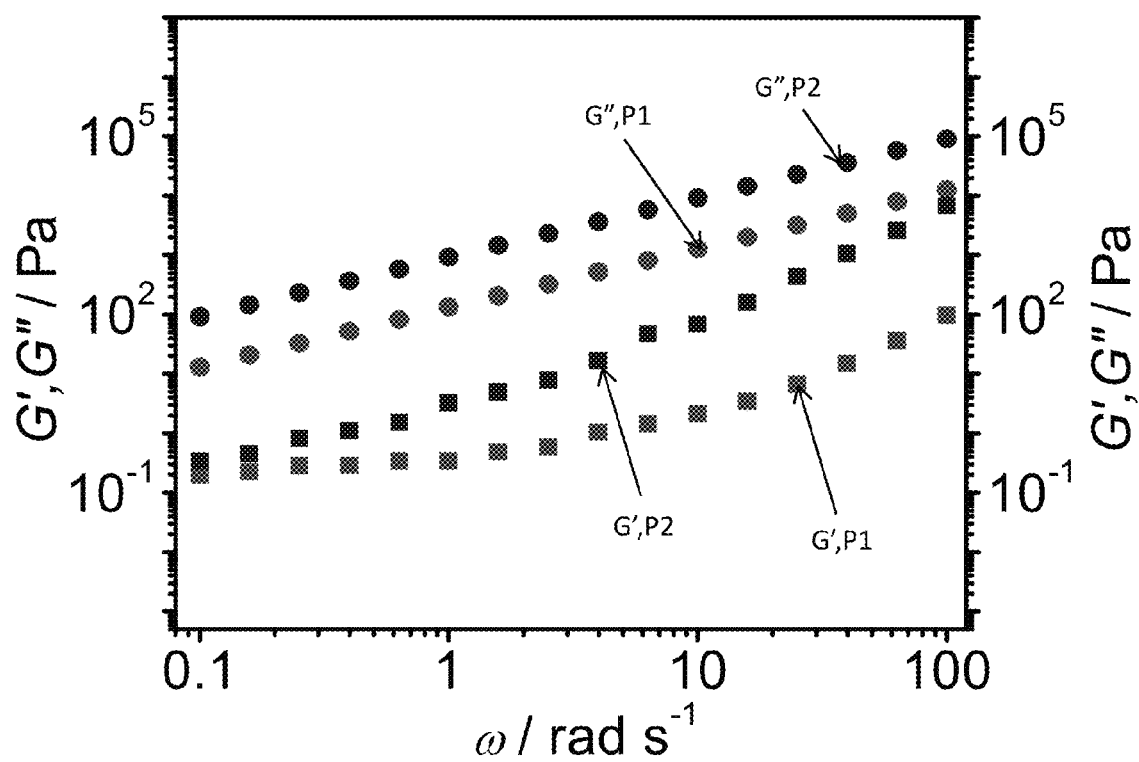
FIG. 25 shows an illustration of the comparison of the frequency dependency of the storage modulus G' and the loss modulus G" of P1 and P2 according to Example 1 and Example 2.

FIG. 25 shows an illustration of the comparison of the frequency dependency of the storage modulus G' and the loss modulus G" of P1 and P2 according to Example 1 and Example 2.

Figure 26:
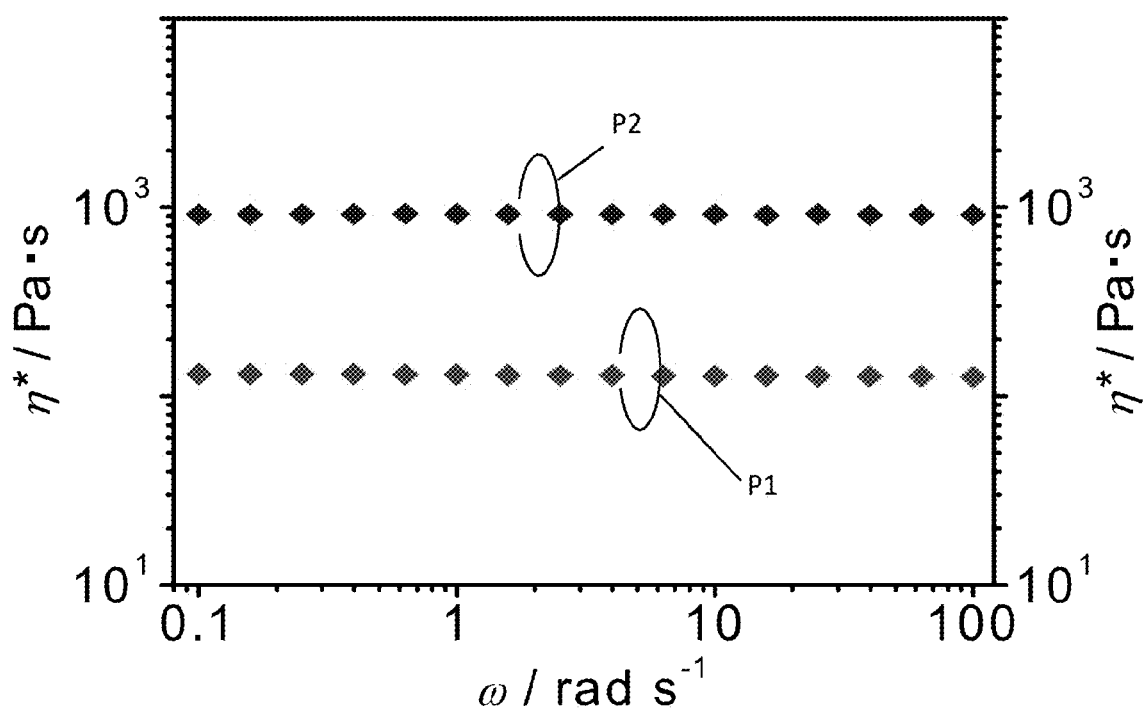
FIG. 26 shows an illustration of the comparison of the frequency dependency of the complex viscosity $\eta^*$ of P1 and P2 according to Example 1 and Example 2.

FIG. 26 shows an illustration of the comparison of the frequency dependency of the complex viscosity η* of P1 and P2 according to Example 1 and Example 2.

P1's loss modulus G" (FIG. 21) exhibited no shear force dependency. P1's storage modulus G' (FIG. 12) exhibited a slight shear force dependency in a lower frequency region, but showed similar state under any shear force. On the other hand, P2's loss modulus G" and storage modulus G' (FIG. 23) never exhibited any shear force dependency. Based on FIG. 21 and FIG. 23, under each shear force, all fulfilled the relationship G">G', indicating that P1 and P2 were in liquid forms.

P1's complex viscosity η* (FIG. 22) and P2's complex viscosity η* (FIG. 24) never exhibited the shear force dependency and the frequency dependency of the complex viscosity η*.

According to FIG. 25 and FIG. 26, P2's complex viscosity η* (920 Pa·s) was found to be higher than that of P1 (130 Pa·s). In the case where the π-conjugated molecule is porphyrin, when the side chain possessed by the π-conjugated molecule (branched alkyl chain in Examples 1 and 2)

is increased, it can be possible, to some extent, to suppress the lamination (referred to also as stacking or J-association) of the π-conjugated molecule and to keep the dispersion. Nevertheless, in the case where the π-conjugated molecule is porphyrin, it is suggested that a larger number of the side chains leads to a higher molecular density which leads to a higher viscosity (complex viscosity) and a smaller number of the side chains leads to a lower viscosity.

Figure 27:
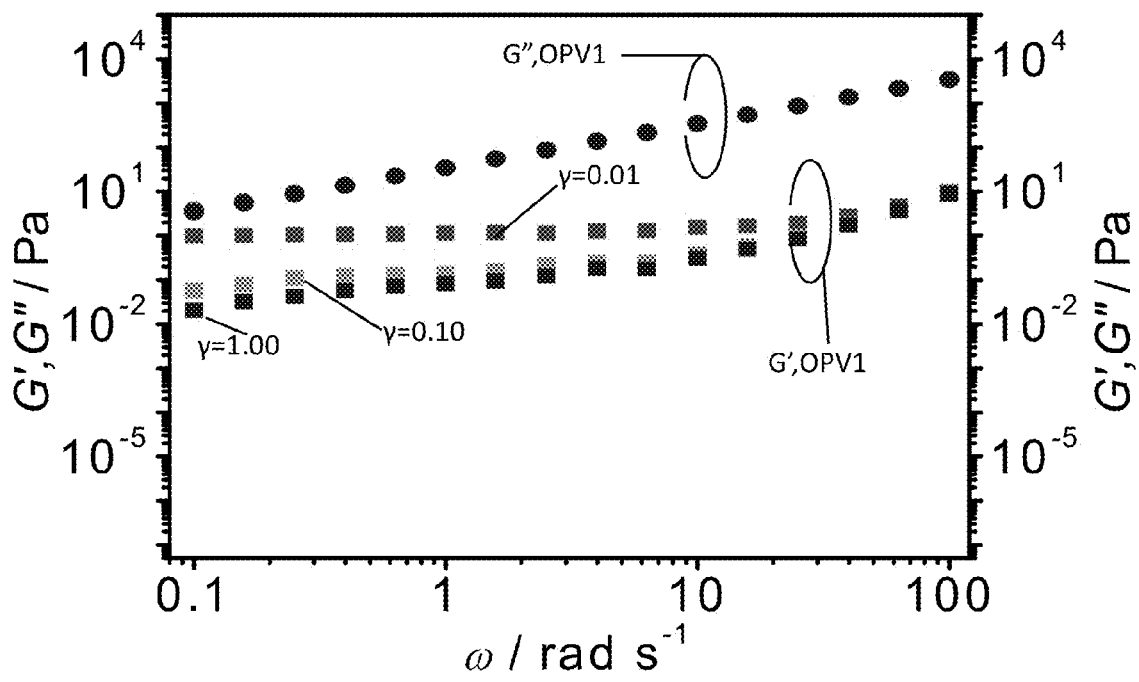
FIG. 27 shows an illustration of the frequency dependency of the storage modulus G' and the loss modulus G" of OPV1 according to Example 3 at each shear force ($\gamma=0.01$, 0.10 and 1.00).

FIG. 27 shows an illustration of the frequency dependency of the storage modulus G' and the loss modulus G" of OPV1 according to Example 3 at each shear force ($\gamma$=0.01, 0.10 and 1.00).

Figure 28:
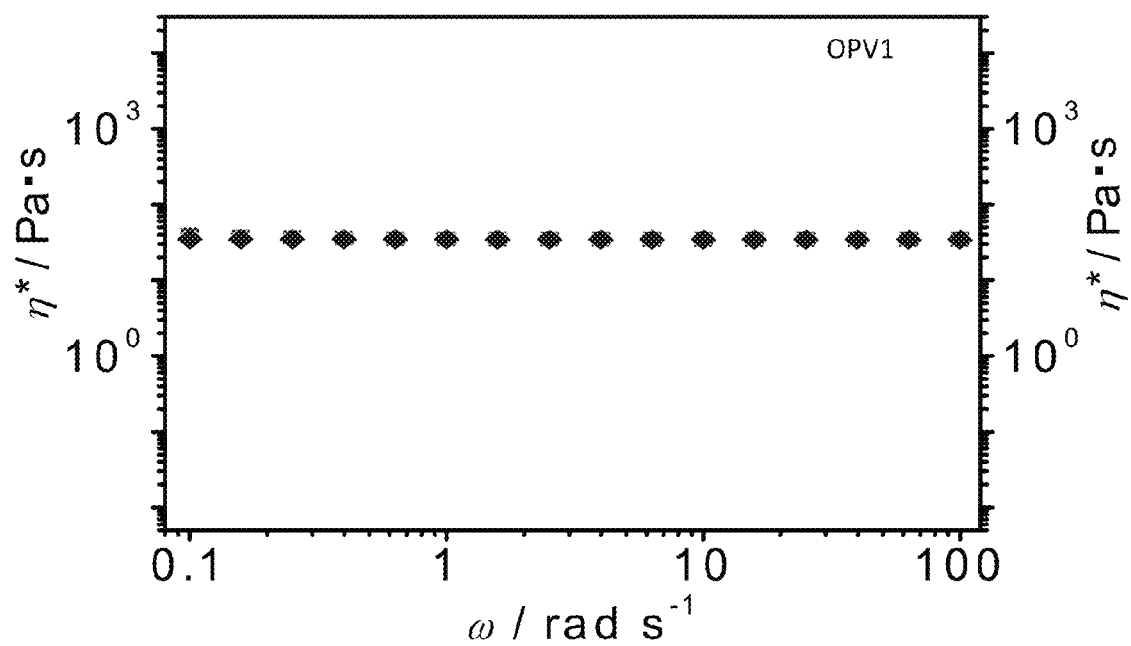
FIG. 28 shows an illustration of the frequency dependency of the complex viscosity $\eta^*$ of OPV1 according to Example 3 at each shear force ($\gamma=0.01$, 0.10 and 1.00).

FIG. 28 shows an illustration of the frequency dependency of the complex viscosity $\eta^*$ of OPV1 according to Example 3 at each shear force ($\gamma$=0.01, 0.10 and 1.00).

Figure 29:
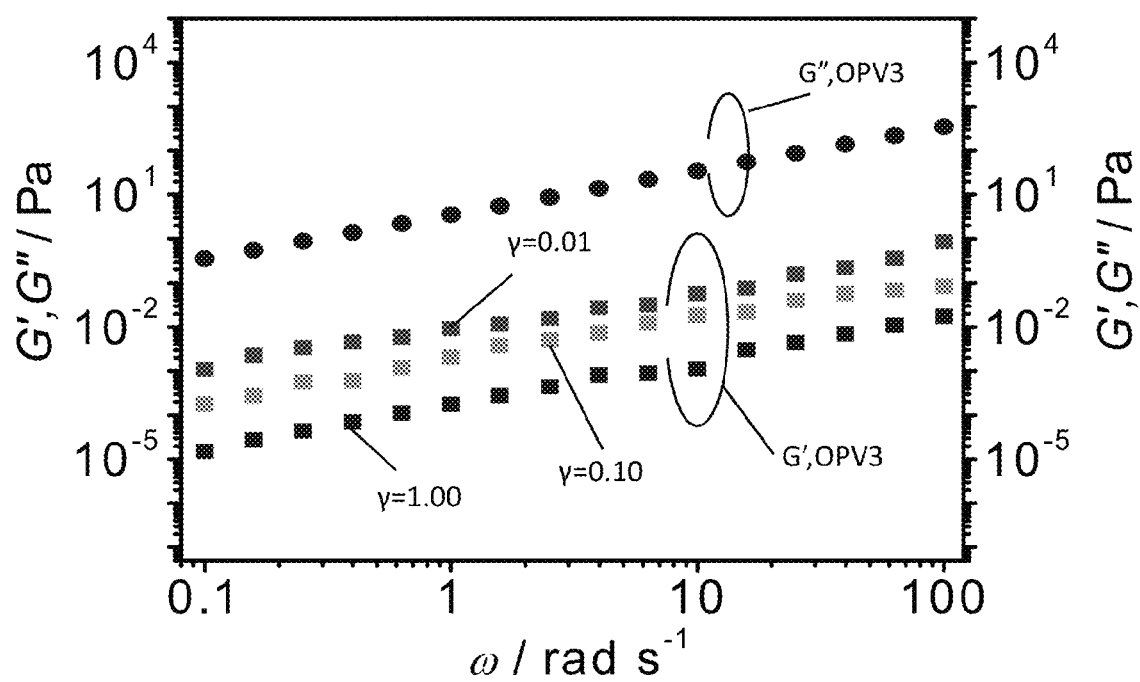
FIG. 29 shows an illustration of the frequency dependency of the storage modulus G' and the loss modulus G" of OPV3 according to Example 5 at each shear force ($\gamma=0.01$, 0.10 and 1.00).

FIG. 29 shows an illustration of the frequency dependency of the storage modulus G' and the loss modulus G" of OPV3 according to Example 5 at each shear force ($\gamma$=0.01, 0.10 and 1.00).

Figure 30:
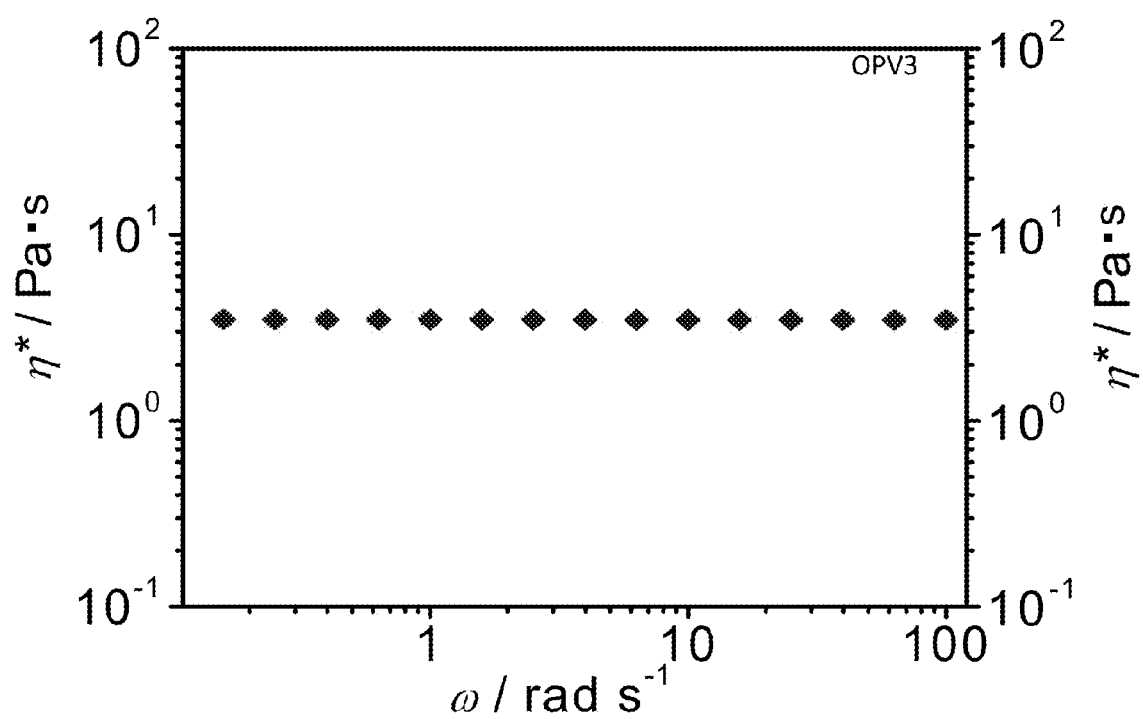
FIG. 30 shows an illustration of the frequency dependency of the complex viscosity $\eta^*$ of OPV3 according to Example 5 at each shear force ($\gamma=0.01$, 0.10 and 1.00).

FIG. 30 shows an illustration of the frequency dependency of the complex viscosity $\eta^*$ of OPV3 according to Example 5 at each shear force ($\gamma$=0.01, 0.10 and 1.00).

Figure 31:
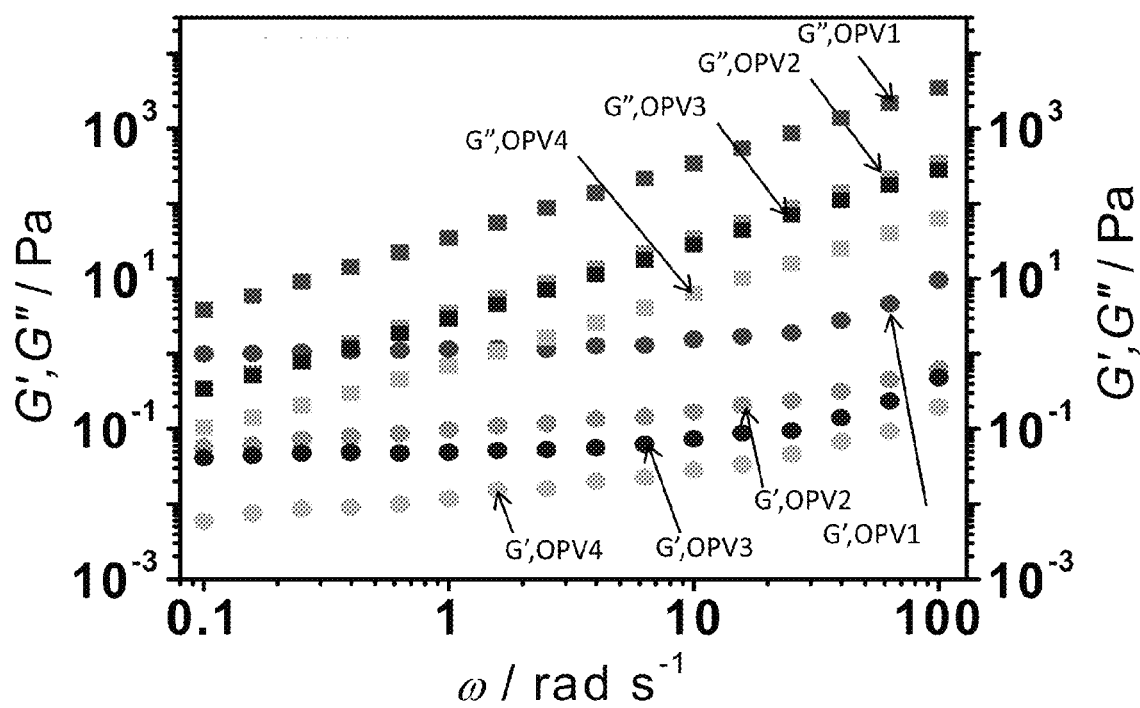
FIG. 31 shows an illustration of the comparison of the frequency dependency of the storage modulus G' and the loss modulus G" of OPV1 to 4 according to Examples 3 to 6.

FIG. 31 shows an illustration of the comparison of the frequency dependency of the storage modulus G' and the loss modulus G" of OPV1 to 4 according to Examples 3 to 6.

Figure 32:
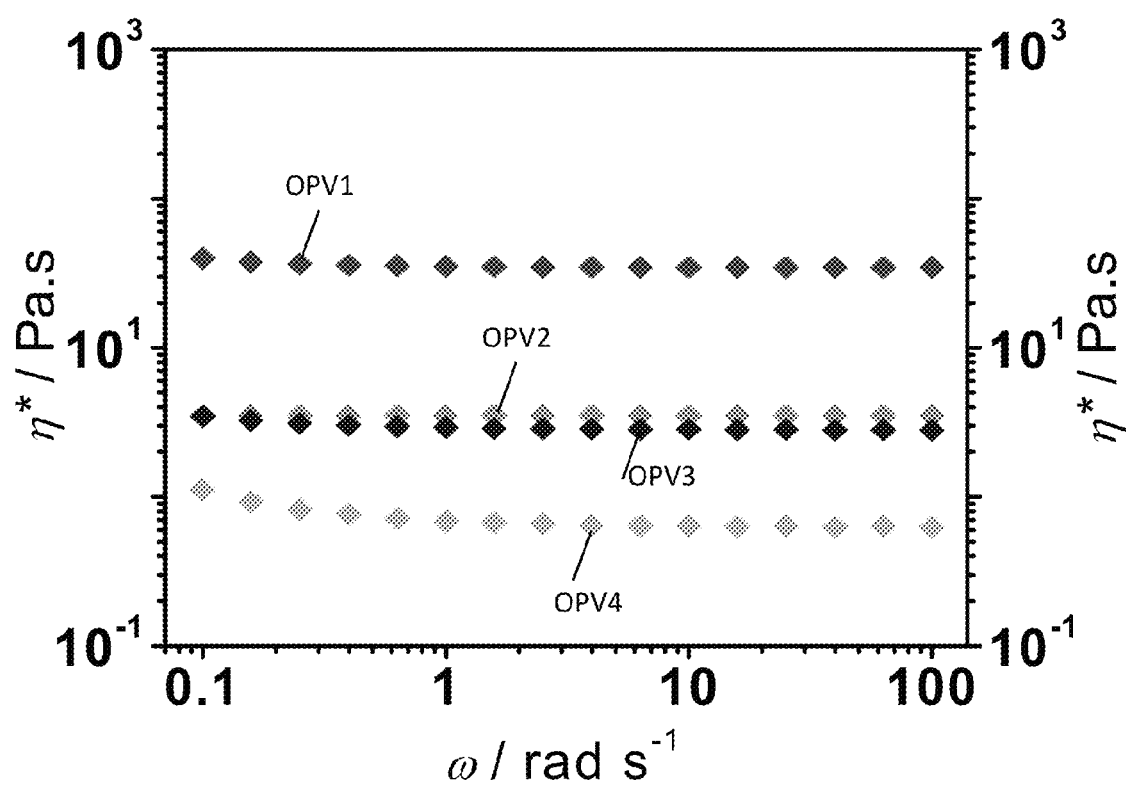
FIG. 32 shows an illustration of the comparison of the frequency dependency of the complex viscosity $\eta^*$ of OPV1 to 4 according to Examples 3 to 6.

FIG. 32 shows an illustration of the comparison of the frequency dependency of the complex viscosity $\eta^*$ of OPV1 to 4 according to Examples 3 to 6.

OPV1's loss modulus G" (FIG. 27) exhibited no shear force dependency. While OPV1's storage modulus G' (FIG. 27) exhibited a shear force dependency in a low frequency region, showed similar state under any shear force. On the other hand, OPV3's loss modulus G" (FIG. 29) exhibited no shear force dependency. While OPV3's storage modulus G' (FIG. 29) tended to be increased under a reduced shear force, it showed similar state under any shear force.

Also similarly to P1 and P2, based on FIG. 27 and FIG. 29, under each shear force, all fulfilled the relationship G">G', indicating that OPV1 and OPV2 were in liquid forms.

OPV1's complex viscosity $\eta^*$ (FIG. 28) and OPV3's complex viscosity $\eta^*$ (FIG. 30) never exhibited the shear force dependency and the frequency dependency of the complex viscosity $\eta^*$.

FIG. 31 and FIG. 32 shows that OPV1, OPV2, OPV3 and then OPV4 exhibited a reduction in the complex viscosity $\eta^*$ in this order. For example, the complex viscosity $\eta^*$ of OPV1 was 35 Pa·s and that of OPV3 was 3.5 Pa·s. This is an opposite tendency to those of P1 and P2 described with referring to FIG. 25 and FIG. 26. It was found that when the π-conjugated molecule is OPV, a larger number of the side chains possessed by the π-conjugated molecule promotes the dispersion of the π-conjugated molecule. Accordingly, it was suggested that when the π-conjugated molecule is OPV, a larger number of the side chains leads to a lower viscosity, and a smaller number of the side chains leads to a higher viscosity.

The difference in the tendency between P1 or P2 and OPV1 to OPV4 is attributable to the difference in the area of the contact between the π-conjugated molecule porphyrin and OPV and in the π-conjugated molecule stacking (lamination). In the case of porphyrin, a larger number of the side chains possessed leads to a higher van der Waals interaction, resulting in a higher viscosity. On the other hand, in the case of OPV, a larger number of the side chains possessed by OPV leads to an effective inhibition of the π-π lamination, resulting in a lower viscosity.

Figure 33:
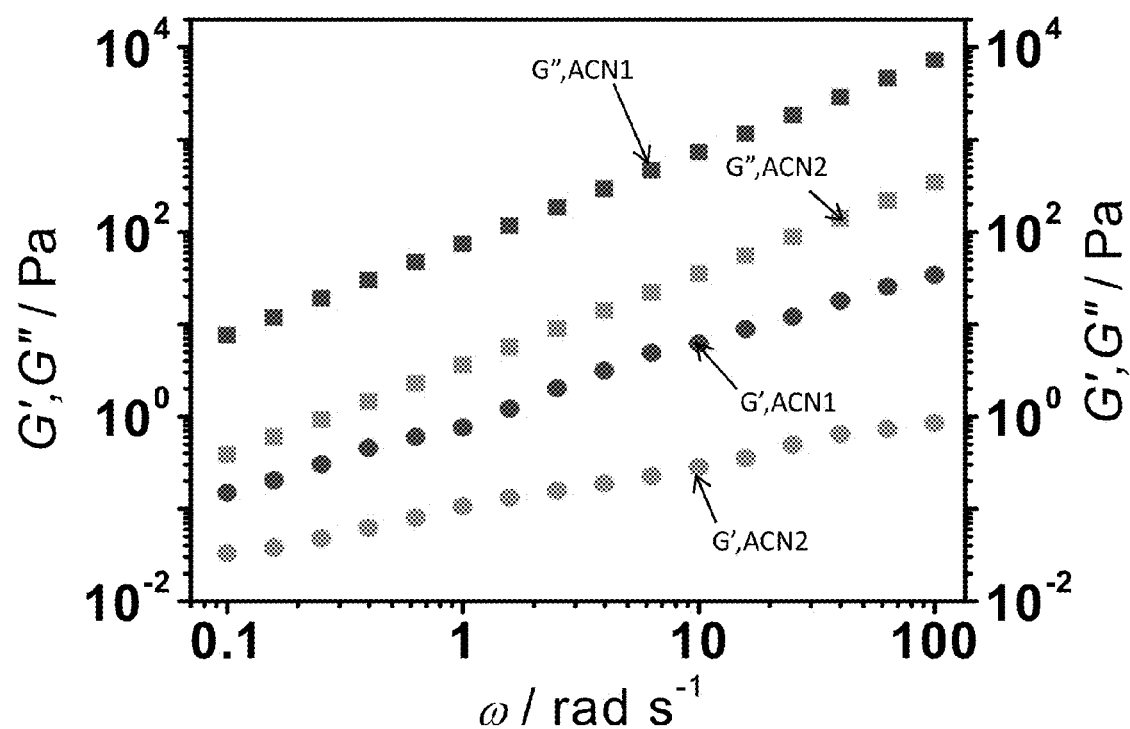
FIG. 33 shows an illustration of the comparison of the frequency dependency of the storage modulus G' and the loss modulus G" of ACN1 and ACN2 according to Examples 7 and 8.

FIG. 33 shows an illustration of the comparison of the frequency dependency of the storage modulus G' and the loss modulus G" of ACN1 and ACN2 according to Example 7 and Example 8.

Figure 34:
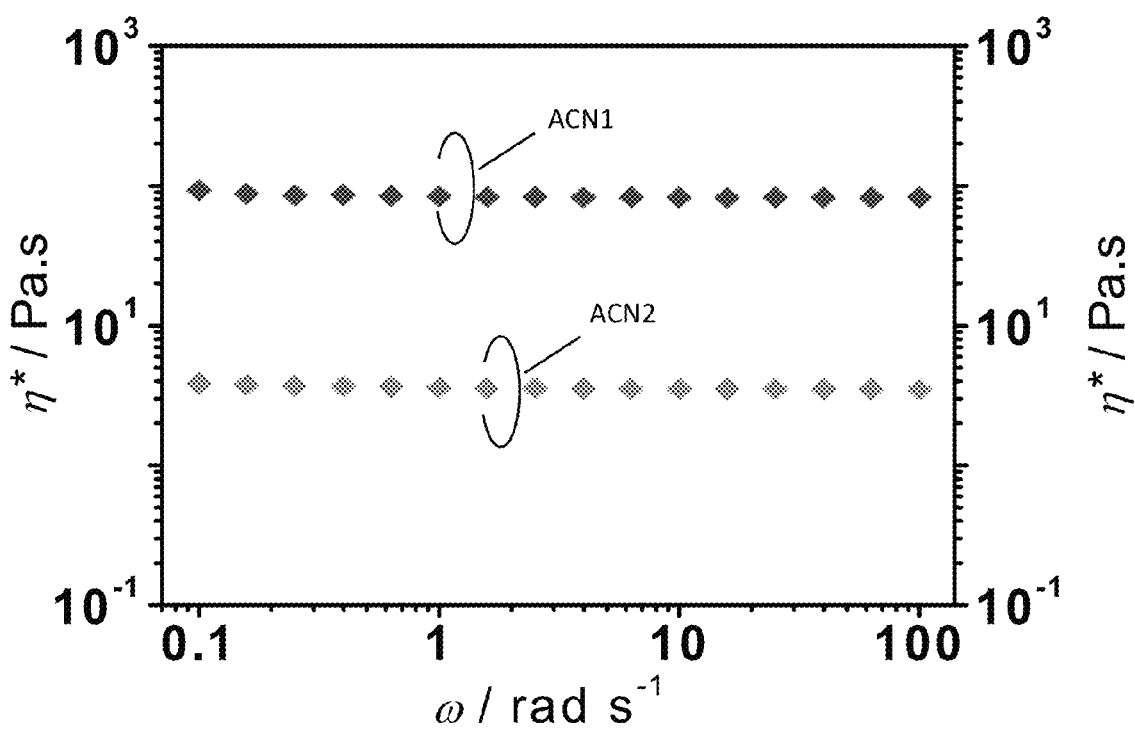
FIG. 34 shows an illustration of the comparison of the frequency dependency of the complex viscosity $\eta^*$ of ACN1 and ACN2 according to Examples 7 and 8.

FIG. 34 shows an illustration of the comparison of the frequency dependency of the complex viscosity $\eta^*$ of ACN1 and ACN2 according to Example 7 and Example 8.

According to FIG. 33, similarly to Example 1 to 6, all fulfilled the relationship G">G', indicating that ACN1 and ACN2 are in liquid forms. Also, the complex viscosity $\eta^*$ of any of ACN1 and ACN2 was confirmed to exhibit no frequency dependency.

According to FIG. 34, ACN1's complex viscosity $\eta^*$ was found to be higher than that of ACN2. In the case where the π-conjugated molecule is anthracene, when a bulky soft side chain is introduced into the π-conjugated molecule, it can be possible, to some extent, to suppress the lamination (referred to also as stacking or J-association) of the π-conjugated molecule and to keep the dispersion. Accordingly, it is suggested that when the π-conjugated molecule is anthracene a bulkier and softer side chain leads to a lower viscosity (complex viscosity).

Although the figure is not shown, FL1 to 4 of Example 9 to 12 similarly fulfilled the relationship G">G', thereby confirming that FL1 to 4 are all in liquid forms. In addition, FL4, FL3, FL2 and then FL1 exhibited a reduction in the complex viscosity $\eta^*$ in this order, indicating that when the π-conjugated molecule is fluorene, a longer π-conjugation leads to a higher viscosity. This means that the contribution by the molecular size effect is large, and a larger molecule leads to a lower molecular mobility and a higher viscosity.

Figure 35:
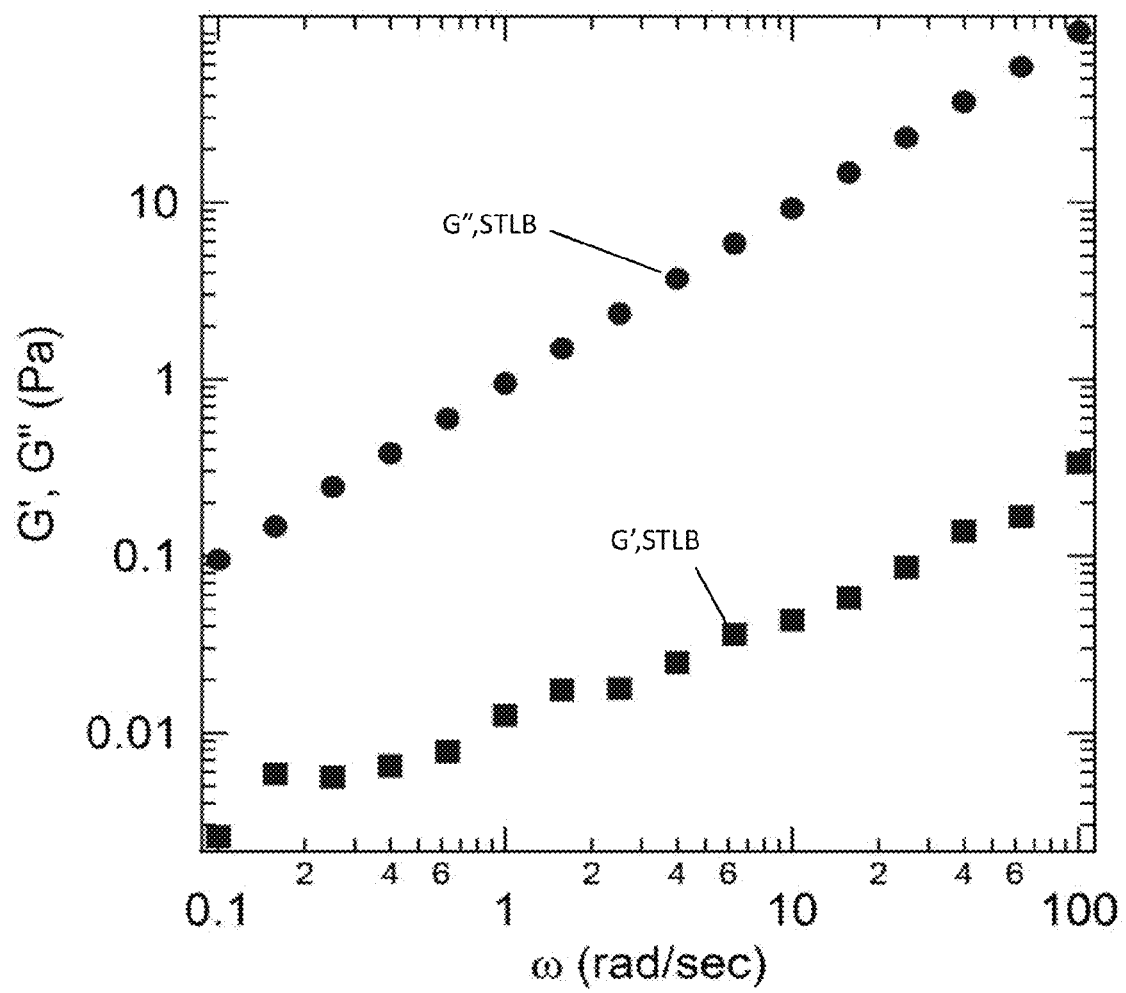
FIG. 35 shows an illustration of the comparison of the frequency dependency of the storage modulus G' and the loss modulus G" of STLB according to Example 13.

FIG. 35 shows an illustration of the comparison of the frequency dependency of the storage modulus G' and the loss modulus G" of STLB according to Example 13.

Figure 36:
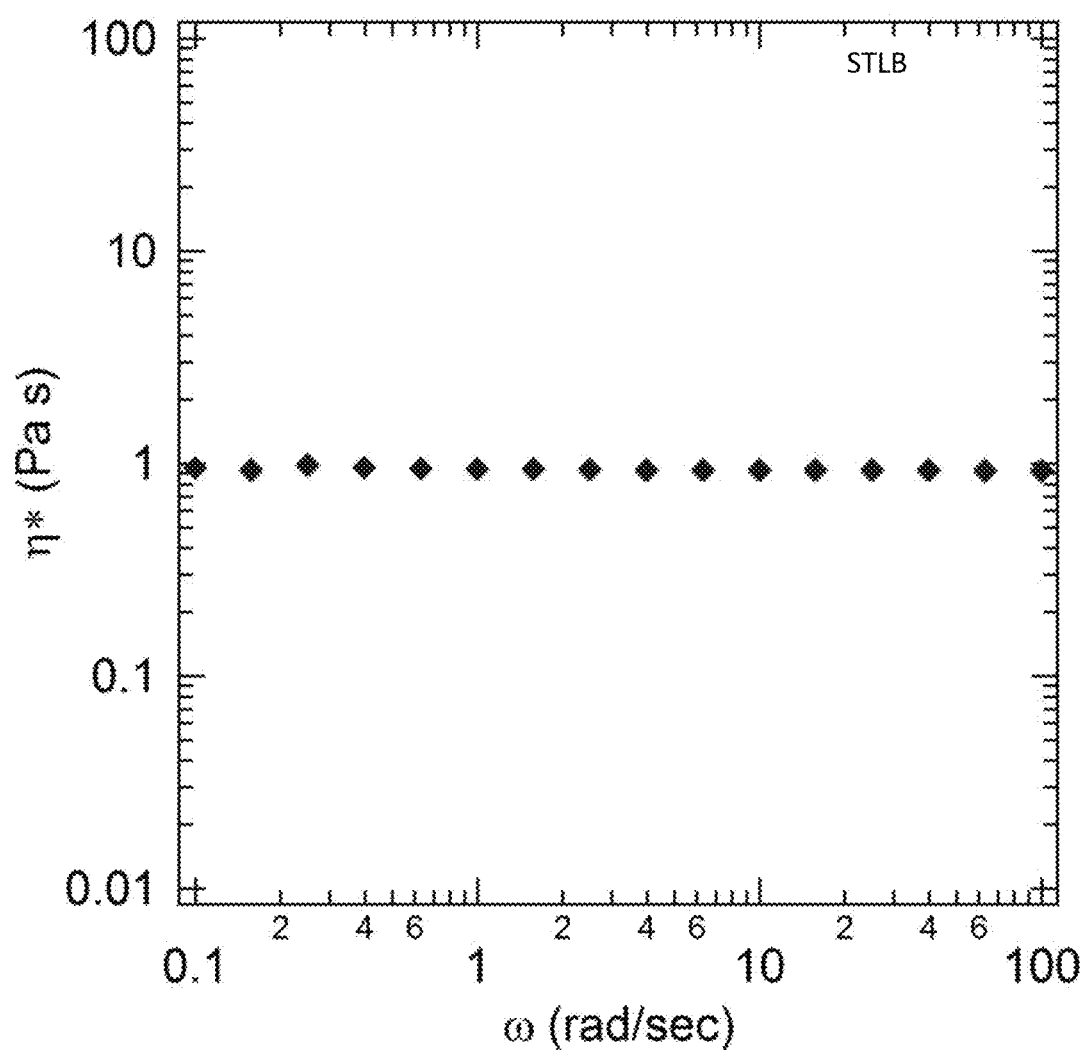
FIG. 36 shows an illustration of the comparison of the frequency dependency of the complex viscosity η* of STLB according to Example 13.

FIG. 36 shows an illustration of the comparison of the frequency dependency of the complex viscosity $\eta^*$ of STLB according to Example 13.

According to FIG. 35, similarly to Example 1 to 8, all fulfilled the relationship G">G', indicating STLB is in a liquid form. Also, STLB's complex viscosity $\eta^*$ was confirmed to exhibit no frequency dependency.

FIG. 37 shows an illustration of the frequency dependency of the storage modulus G' and the loss modulus G" of $(2,4,6)F180NC_{60}$ at each shear force ($\gamma$=0.01, 0.10 and 1.00).

FIG. 38 shows an illustration of the frequency dependency of the complex viscosity $\eta^*$ of $(2,4,6)F180NC_{60}$ at each shear force ($\gamma$=0.01, 0.10 and 1.00).

According to FIG. 37 and FIG. 38, the storage modulus G', the loss modulus G" and the complex viscosity $\eta^*$ of $(2,4,6)F180NC_{60}$ never exhibited the dependency under each shear force. Also, the relationship G">G' was fulfilled, thereby confirming that $(2,4,6)F180NC_{60}$ is in a liquid form. The complex viscosity $\eta^*$ exhibited no frequency dependency. When focusing on the complex viscosity $\eta^*$, the complex viscosity $\eta^*$ of each of P1, P2, OPV1 to OPV4, ACN2, ACN2, FL1 to FL4, STLB is smaller than that of $(2,4,6)F180NC_{60}$. Accordingly, it is suggested that the ambient temperature liquid organic material of the invention has a low viscosity and can preferably be used as a solvent.

As discussed above, it was confirmed, according to FIG. 21 to FIG. 36, that the ambient temperature liquid-form organic material according to the present invention is in a liquid form at ambient temperature. It is also suggested that, the viscosity of the ambient temperature liquid-form organic material can be controlled via the selection of the π-conjugated molecule and/or the selection and the number of the side chains possessed by the π-conjugated molecule.

FIG. 39 shows an illustration of the results of thermogravimetric analysis of P1 according to Example 1.

The thermogravimetric curve (TG curve) started to exhibit the weight loss at 358° C. Thus, P1 had a degradation temperature of 358° C. Accordingly, it was indicated that the ambient temperature liquid-form organic material of the present invention is stable thermally even in a high temperature environment. Although the figures are not indicated, it was confirmed that P2, OPV1 to 4 also had degradation temperatures of 350° C. or higher and thermally stable.

FIG. 40 shows an illustration of the results of the differential scanning calorimetry of P1 according to Example 1.

The differential calorimetric curve (DSC curve) exhibited an exothermic peak at −13.6° C. during cooling. This −13.6° C. exothermic peak was confirmed to correspond to the glass transition temperature. Although no figure is shown, the glass transition temperature of P2 was also −10° C. or below.

According to FIG. 39 and FIG. 40, it was confirmed that P1 is in a liquid form from −13.6° C. to 350° C., and that the ambient temperature liquid-form organic material of the present invention is in a liquid form at least from room temperature to 350° C. and can be used even in a high temperature environment.

Figure 41:
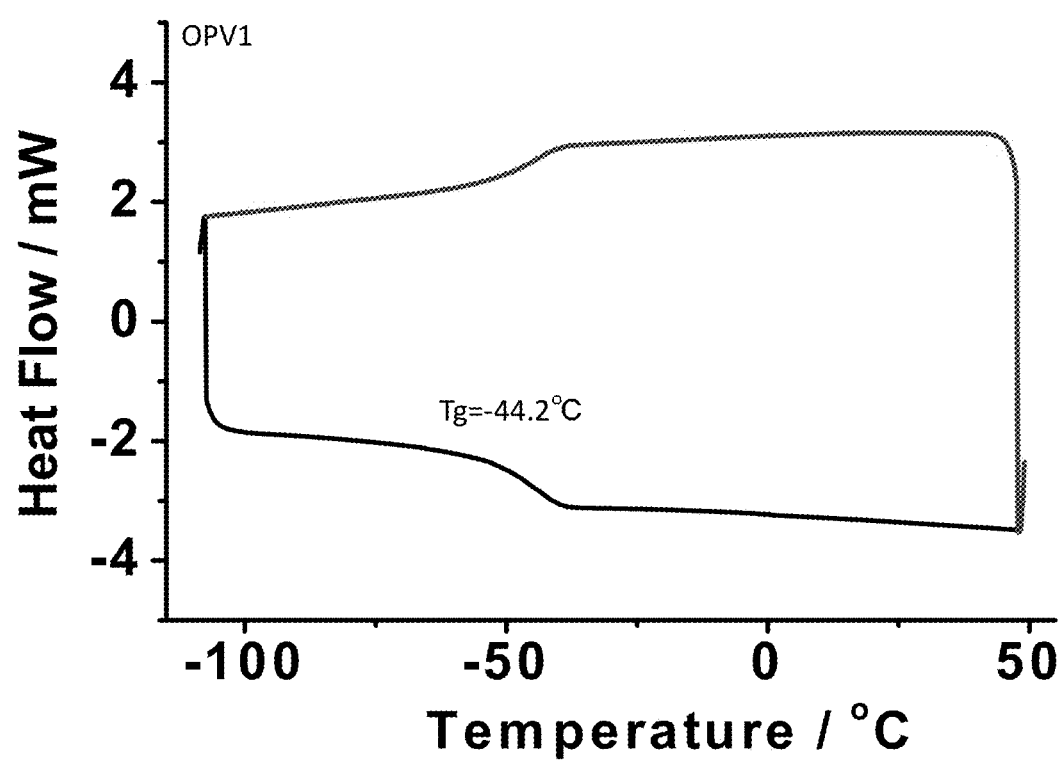
FIG. 41 shows an illustration of the results of the differential scanning calorimetry of OPV1 according to Example 3.

FIG. 41 shows an illustration of the results of the differential scanning calorimetry of OPV1 according to Example 3.

Figure 42:
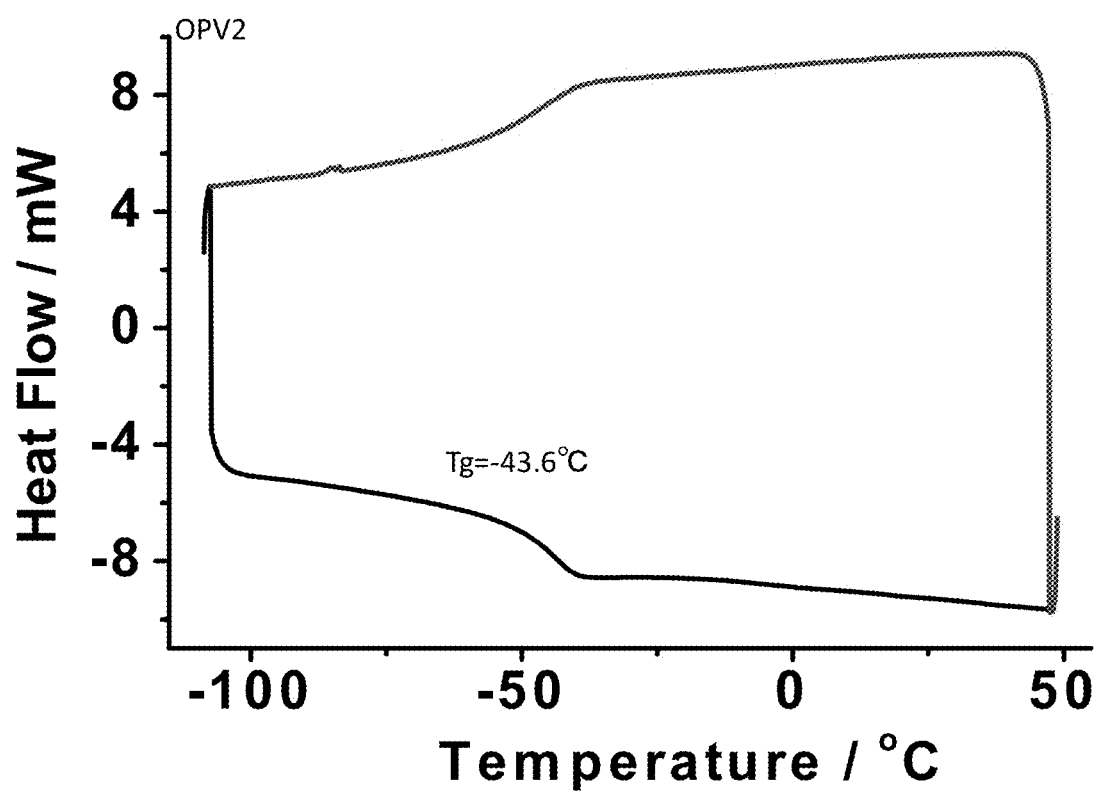
FIG. 42 shows an illustration of the results of the differential scanning calorimetry of OPV2 according to Example 4.

FIG. 42 shows an illustration of the results of the differential scanning calorimetry of OPV2 according to Example 4.

Figure 43:
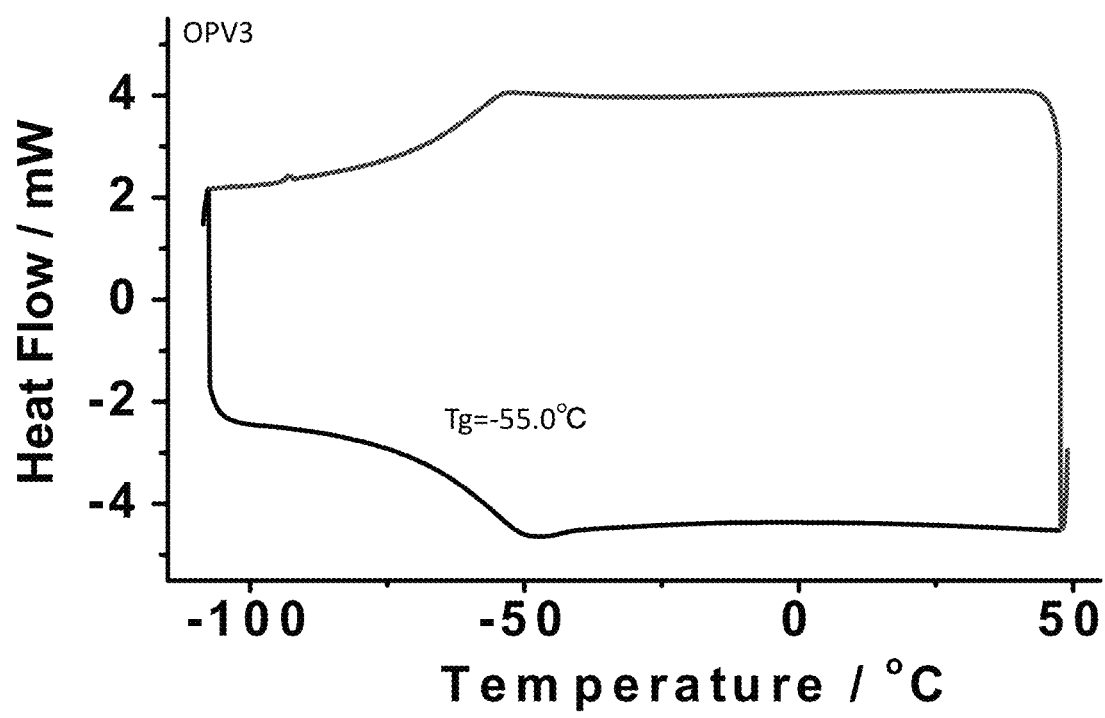
FIG. 43 shows an illustration of the results of the differential scanning calorimetry of OPV3 according to Example 5.

FIG. 43 shows an illustration of the results of the differential scanning calorimetry of OPV3 according to Example 5.

Figure 44:
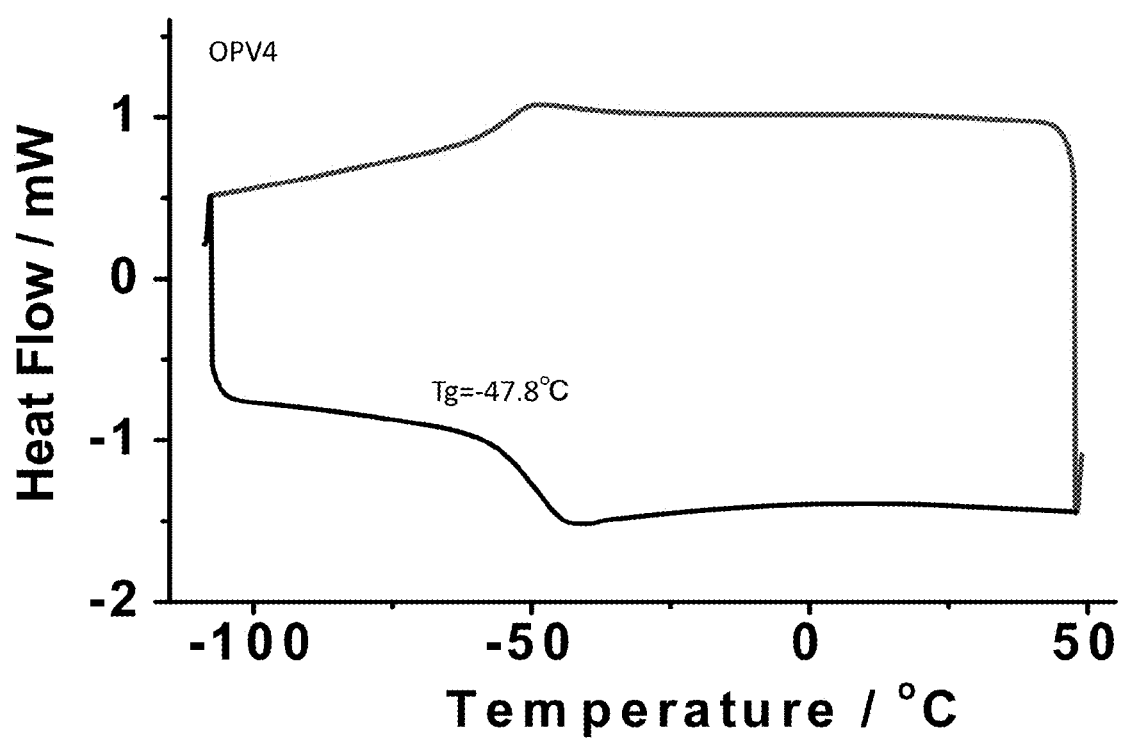
FIG. 44 shows an illustration of the results of the differential scanning calorimetry of OPV4 according to Example 6.

FIG. 44 shows an illustration of the results of the differential scanning calorimetry of OPV4 according to Example 6.

FIG. 41 to FIG. 44 show that OPV1 to 4 exhibited the respective differential calorimetric curves (DSC curves) having the exothermic peaks at −44.2° C., −43.6° C., −55.0° C. and −47.8° C. during cooling. These exothermic peaks were confirmed to correspond to the glass transition temperatures. Accordingly, it was confirmed that OPV1 to OPV4 are in liquid forms from about −40° C. to −50° C. through 350° C. and that the ambient temperature liquid-form organic material of the present invention is in a liquid form at least from room temperature to 350° C.

FIG. 45 shows an illustration of the results of the differential scanning calorimetry of FL1 to 4 according to Examples 9 to 12.

FIG. 45 shows that FL1 to FL4 exhibited the respective differential calorimetric curves (DSC curves) having the exothermic peaks at −84° C., −51° C., −59° C. and −50° C. during cooling. These exothermic peaks were confirmed to correspond to the glass transition temperatures. Accordingly, it was confirmed that FL1 to FL4 are in liquid forms from about −50° C. (about −80° C. for FL1) and that the ambient temperature liquid-form organic material of the present invention is in a liquid form at least at room temperature.

It should be noted that the glass transition temperature generally tends to increase as n is increased but that the value of the glass transition temperature becomes reversed depending on whether n is an even number or an odd number. Thus, FL1 (n=1), FL3 (n=3), FL2 (n=2) then FL4 (n=4) exhibited the glass transition temperature which was increased in this order. This suggests that there is a dependency on the position of the fluorene side chain which depends on whether n is an even number or an odd number.

For convenience, the glass transition temperatures are shown altogether in Table 2.

TABLE 2

Glass transition temperature Tg(°C.) of Examples 1, 3 to 6 and 9 to 12

| Example | Sample name | Glass transition temperature (° C.) |
|---|---|---|
| 1 | P1 | −13.6 |
| 3 | OPV1 | −44.2 |
| 4 | OPV2 | −43.6 |
| 5 | OPV3 | −55.0 |
| 6 | OPV4 | −47.8 |
| 9 | FL1 | −84.0 |
| 10 | FL2 | −51.0 |
| 11 | FL3 | −59.0 |
| 12 | FL4 | −50.0 |

FIG. 46 shows an absorption spectrum of P1 according to Example 1.

P1 Solution absorption spectrum and P1 Film absorption spectrum both exhibited a similar state. P1 Solution and P1 Film absorption spectra exhibited maximum absorption wavelengths ($\lambda_{max}$) respectively of 423 nm and 430 nm. P1 Film exhibited a maximum absorption wavelength which underwent a slight red-shift (7 nm) when compared with that of P1 Solution. This is because that the molecule in P1 Film forms a J-association body more readily when compared with the molecule in P1 Solution. Nevertheless, this J-association level can be neglected because it is not problematic upon application.

FIG. 47 is an image showing a luminescent state of P1 according to Example 1.

FIG. 47(A) shows a state where P1 is not irradiated with the ultraviolet light, while FIG. 47(B) shows a state where P1 is irradiated with the ultraviolet light. According to FIG. 47, P1 was found to exhibit a red luminescence upon an ultraviolet light (365 nm) irradiation.

FIG. 48 shows a luminescent spectrum of P1 according to Example 1.

P1 (sample is P1 Film) was found to be a red luminescent material which is excited at an excitation wavelength (430 nm) to exhibit an emission peak at a wavelength of 665 nm. Although the figure is not shown, P1 Solution had an emission spectrum which has, similarly to P1 Film, an emission peak wavelength of 665 nm, whose emission intensity and the peak shape were higher and sharper than those of P1 Film. This may be because that the molecule in P1 Film has a stronger intermolecular interaction when compared with the molecule in P1 Solution.

Figure 49:
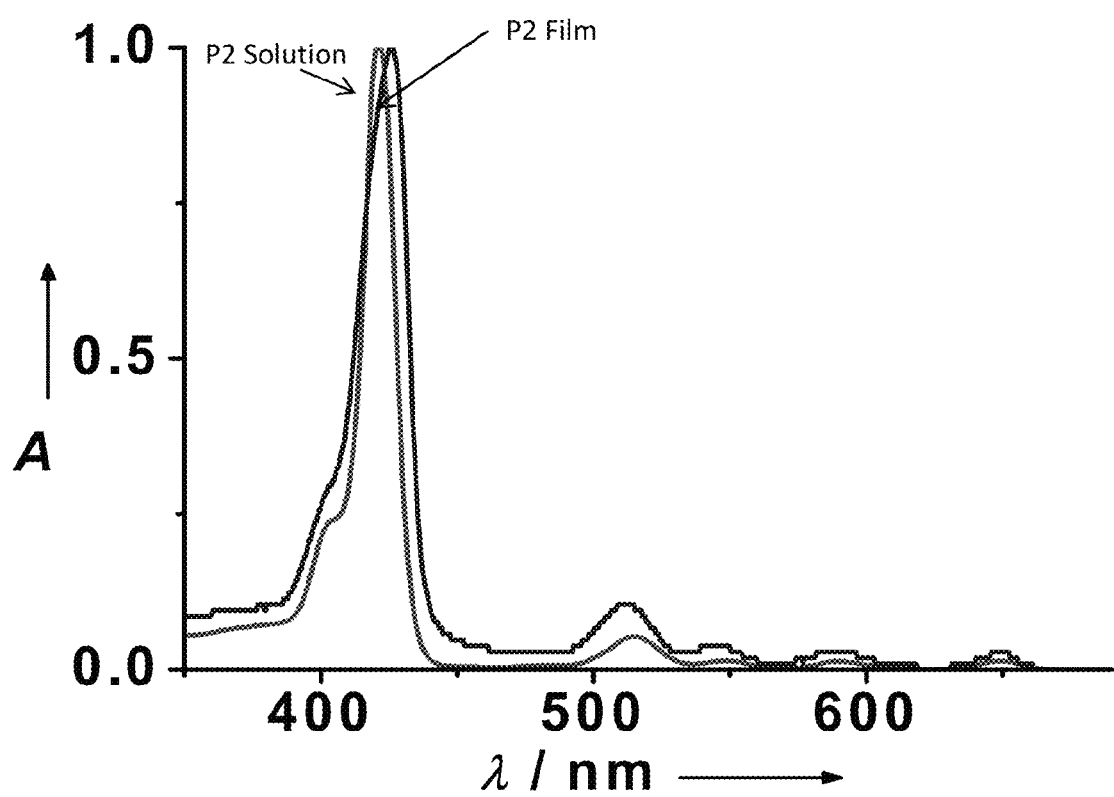
FIG. 49 shows an absorption spectrum of P2 according to Example 2.

FIG. 49 shows an absorption spectrum of P2 according to Example 2.

P2 Solution absorption spectrum and P2 Film absorption spectrum both exhibited a similar state. P2 Solution and P2 Film absorption spectra exhibited maximum absorption wavelengths ($\lambda_{max}$) respectively of 421 nm and 424 nm. P2 Film exhibited a maximum absorption wavelength which underwent a slight red-shift (3 nm) when compared with that of P2 Solution. This is because that the molecule in P2 Film forms a J-association body more readily when compared with the molecule in P2 Solution, similarly to P1 of Example 1. Nevertheless, this J-association level can be neglected because it is not problematic upon application.

Figure 50:
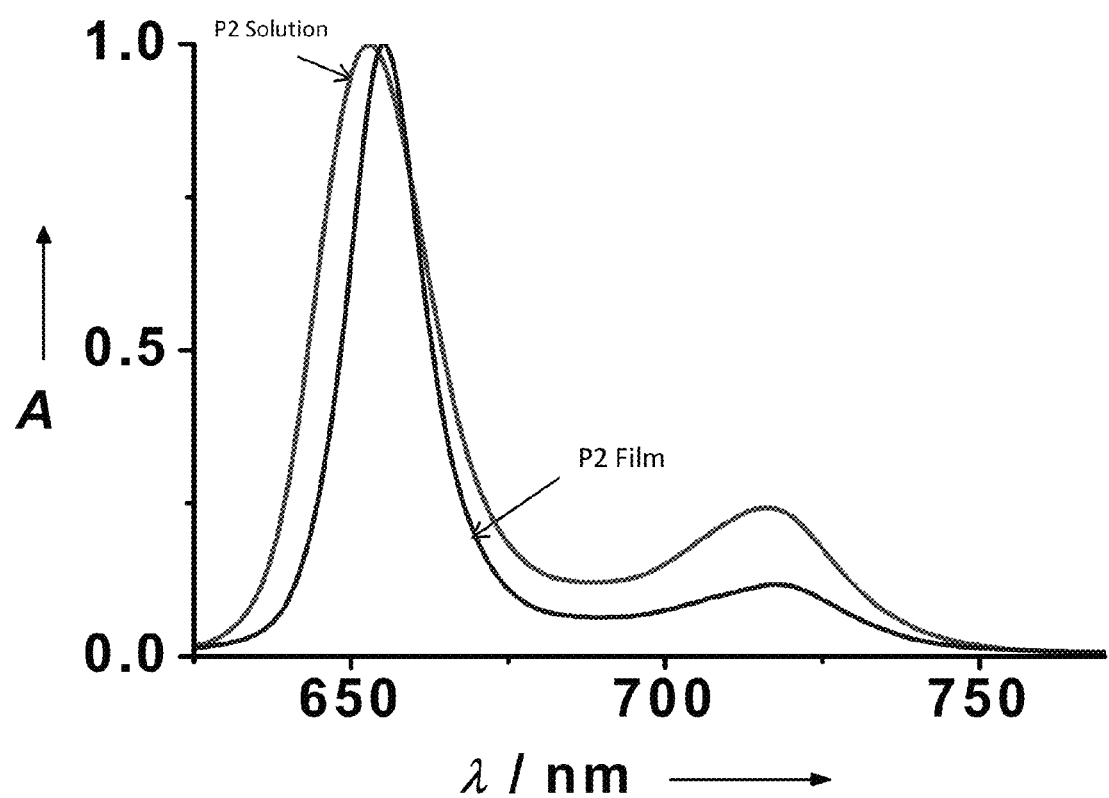
FIG. 50 shows a luminescent spectrum of P2 according to Example 2.

FIG. 50 shows a luminescent spectrum of P2 according to Example 2.

P2 Solution and P2 Film were found to be red luminescent bodies which were excited at an excitation wavelength (430 nm) to exhibit emission peak wavelengths of 652 nm and 655 nm, respectively.

Figure 51:
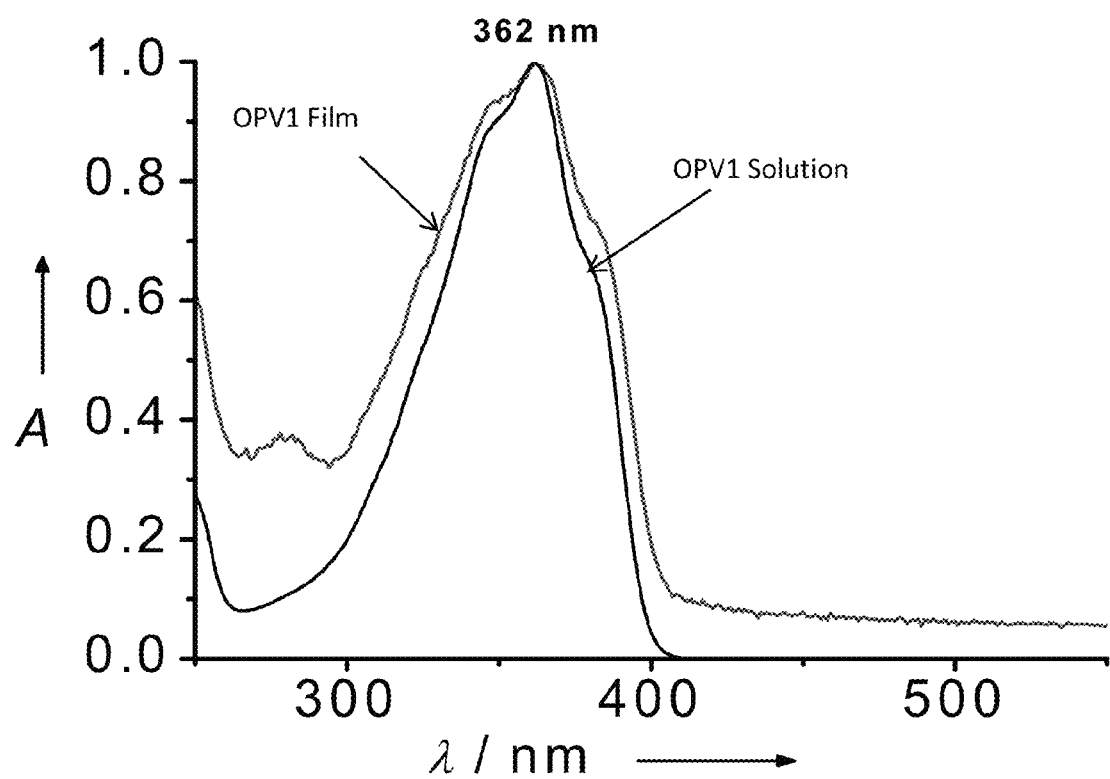
FIG. 51 shows an absorption spectrum of OPV1 according to Example 3.

FIG. 51 shows an absorption spectrum of OPV1 according to Example 3.

OPV1 Solution (OPV1 dissolved in dichloromethane ($1 \times 10^{-5}$M) to form a solution, hereinafter referred to as OPV1 Solution) absorption spectrum and OPV1 spin coat film (OPV1 Solution spin-coated onto a quartz substrate to form a film, hereinafter referred to as OPV1 Film) absorption spectrum both exhibited a similar state. OPV1 Solution and OPV1 Film absorption spectra exhibited maximum absorption wavelengths ($\lambda_{max}$) which were both 362 nm. Unlike to P1, the maximum absorption wavelength of OPV1 Solution and that of OPV1 Film had no shift between them. This is because that the molecule of OPV1 Film and the molecule of the OPV1 Solution are both present in a single molecule dispersion state.

Figure 52:
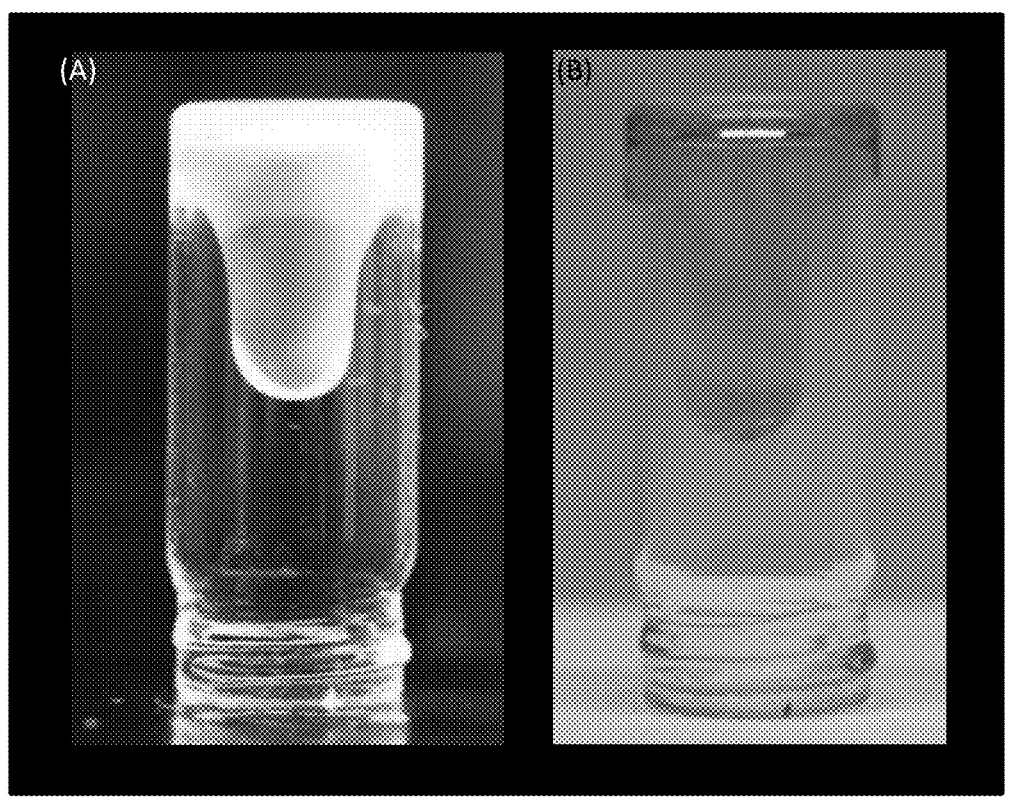
FIG. 52 is an image showing a luminescent state of OPV1 according to Example 3.

FIG. 52 is an image showing a luminescent state of OPV1 according to Example 3.

FIG. 52(B) shows a state of OPV1 under ambient visible light, while FIG. 52(A) shows a state where OPV1 was irradiated with the ultraviolet light. FIG. 52 shows that OPV1 exhibits a blue luminescence upon the ultraviolet light irradiation.

Figure 53:
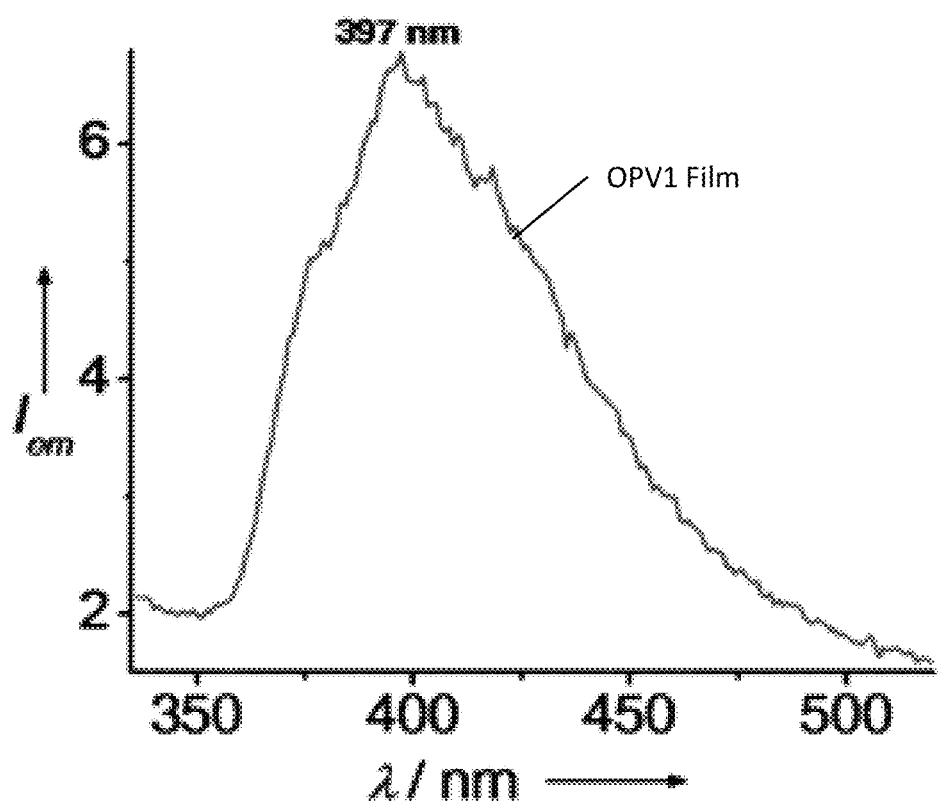
FIG. 53 shows a luminescent spectrum of OPV1 according to Example 3.

FIG. 53 shows a luminescent spectrum of OPV1 according to Example 3.

OPV1 (sample is OPV1 Film) was found to be a blue luminescent material which is excited at an excitation wavelength (360 nm) to exhibit an emission peak at a wavelength of 397 nm. Although the figure is not shown, OPV1 Solution exhibited an emission spectrum whose emission peak wavelength, emission intensity and peak shape were similar to those of OPV1 Film. This may be because that the molecule in OPV1 Film and the molecule in OPV1 Solution have no intermolecular interaction.

Figure 54:
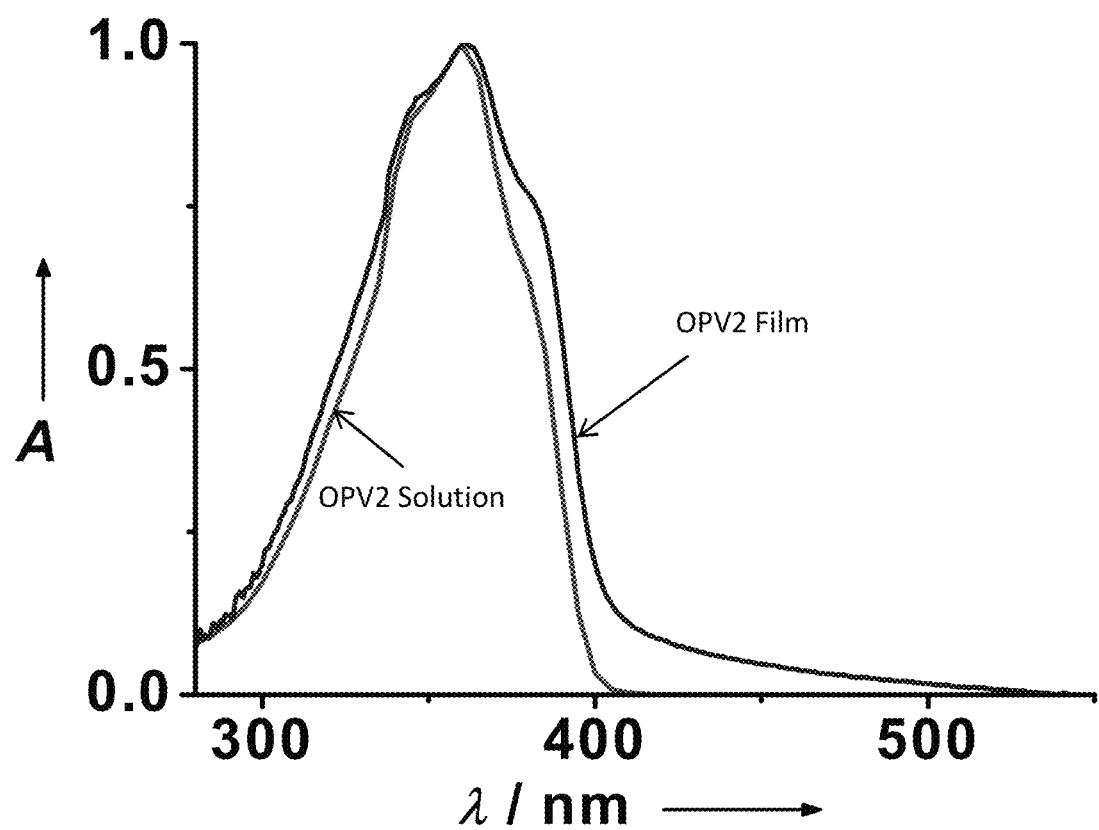
FIG. 54 shows an absorption spectrum of OPV2 according to Example 4.

FIG. 54 shows an absorption spectrum of OPV2 according to Example 4.

OPV2 Solution (OPV2 dissolved in dichloromethane ($5 \times 10^{-5}$M) to form a solution, hereinafter referred to as OPV2 Solution) absorption spectrum and OPV2 spin coat film (OPV2 Solution spin-coated onto a quartz substrate to form a film, hereinafter referred to as OPV2 Film) absorption spectrum both exhibited a similar state. The OPV2 Solution and the OPV2 Film absorption spectra exhibited maximum absorption wavelengths ($\lambda_{max}$) respectively of 360 nm and 361 nm. Similarly to OPV1, the maximum absorption wavelength of OPV2 Solution and that of OPV2 Film had no substantial shift between them. Here again, the molecule in OPV2 Film and the molecule in OPV2 Solution were both present in a single molecule dispersion state.

Figure 55:
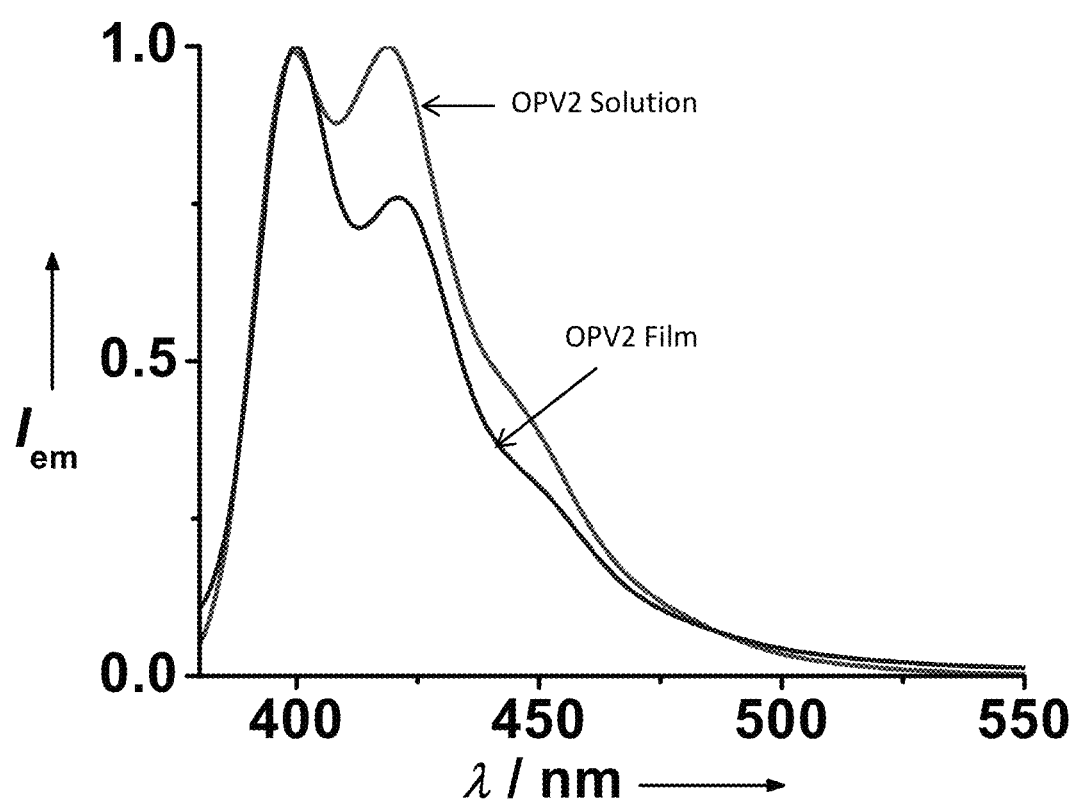
FIG. 55 shows a luminescent spectrum of OPV2 according to Example 4.

FIG. 55 shows a luminescent spectrum of OPV2 according to Example 4.

OPV2 Solution and the OPV2 Film were found to be blue luminescent bodies which are excited at an excitation wavelength (360 nm) to exhibit maximum emission peak wavelengths of 399 nm and 400 nm, respectively. While the maximum emission peak wavelength and the emission intensity exhibited no substantial difference between OPV2 Solution and OPV2 Film, the emission intensity of the second emission peak indicated that OPV2 Film had an emission intensity which was reduced when compared with that of OPV2 Solution. This may be due to the difference in the environment where the OPV Core is placed. This second emission peak is assigned to the transition from 0-1 vibronic transition S1 to S2 excitation state.

Figure 56:
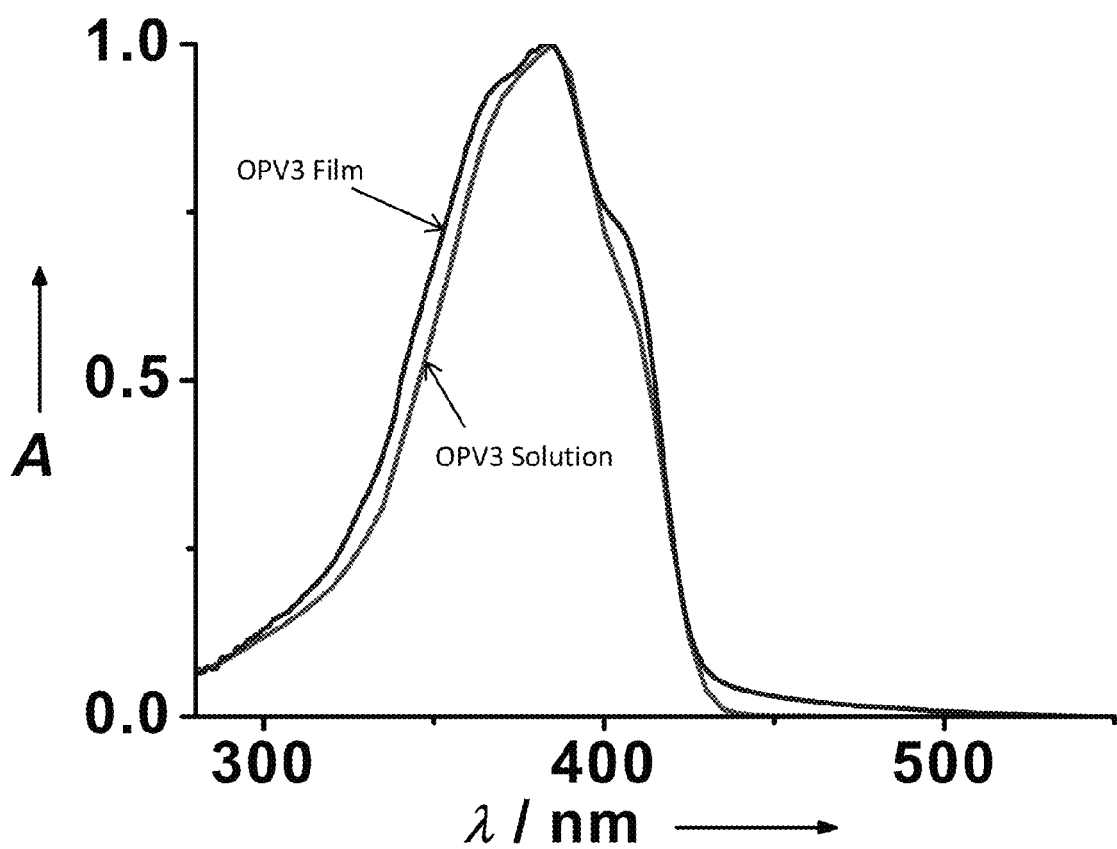
FIG. 56 shows an absorption spectrum of OPV3 according to Example 5.

FIG. 56 shows an absorption spectrum of OPV3 according to Example 5.

OPV3 Solution (OPV3 dissolved in dichloromethane ($5 \times 10^{-5}$M) to form a solution, hereinafter referred to as OPV3 Solution) absorption spectrum and OPV3 spin coat film (OPV3 Solution spin-coated onto a quartz substrate to form a film, hereinafter referred to as OPV3 Film) absorption spectrum both exhibited a similar state. The OPV3 Solution and the OPV3 Film absorption spectra exhibited maximum absorption wavelengths ($\lambda_{max}$) which were both 355 nm. Similarly to OPV1 to 2, the maximum absorption wavelength of OPV3 Solution and that of OPV3 Film had no shift between them. Here again, it is indicated that the molecule in OPV3 Film and the molecule in OPV3 Solution were both present in a single molecule dispersion state.

Figure 57:
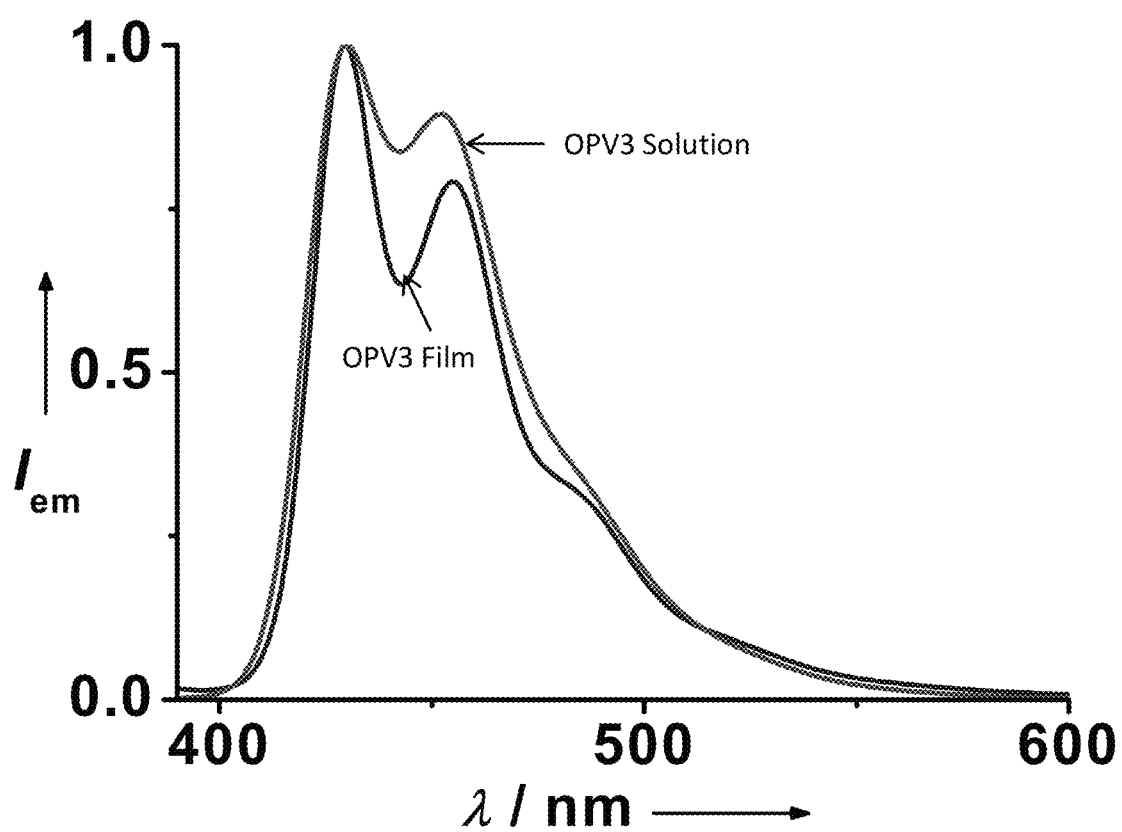
FIG. 57 shows a luminescent spectrum of OPV3 according to Example 5.

FIG. 57 shows a luminescent spectrum of OPV3 according to Example 5.

OPV3 Solution and the OPV3 Film were found to be a blue luminescent bodies which are excited at an excitation wavelength (365 nm) to exhibit maximum emission peak wavelengths of 430 nm and 429 nm, respectively. Similarly to OPV2, the maximum emission peak wavelength and the emission intensity exhibited no substantial difference between OPV3 Solution and OPV3 Film, but the emission intensity of the second emission peak indicated that OPV3 Film had an emission intensity which was reduced when compared with that of OPV3 Solution. Similarly to OPV2, this may be due to the difference in the environment where the OPV Core is placed.

Figure 58:
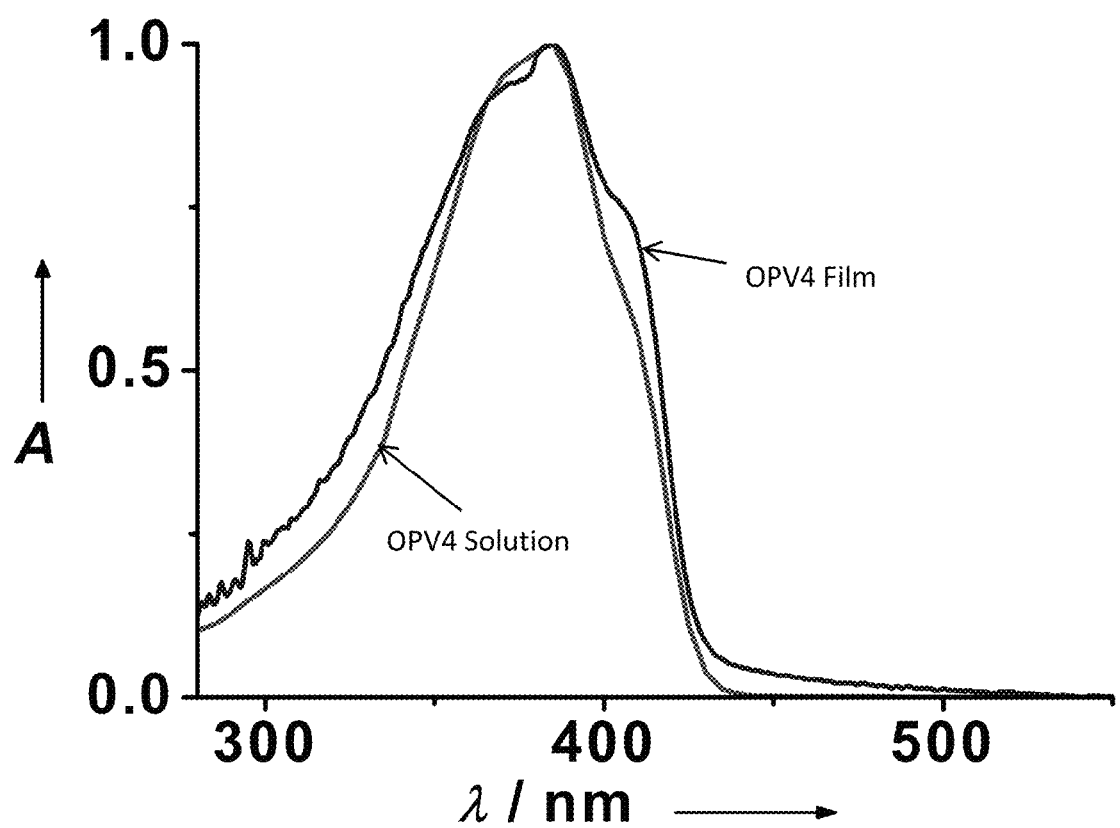
FIG. 58 shows an absorption spectrum of OPV4 according to Example 6.

FIG. 58 shows an absorption spectrum of OPV4 according to Example 6.

OPV4 Solution (OPV4 dissolved in dichloromethane ($5 \times 10^{-5}$M) to form a solution, hereinafter referred to as OPV4 Solution) absorption spectrum and OPV4 spin coat film (OPV4 Solution spin-coated onto a quartz substrate to form a film, hereinafter referred to as OPV4 Film) absorption spectrum both exhibited a similar state. The OPV4 Solution and the OPV4 Film absorption spectra exhibited maximum absorption wavelengths ($\lambda_{max}$) which were both 385 nm. Similarly to OPV1 to 3, the maximum absorption wavelength of OPV4 Solution and that of OPV4 Film had no shift between them. Here again, it is indicated that the molecule in OPV4 Film and the molecule in OPV4 Solution were both present in a single molecule dispersion state.

Figure 59:
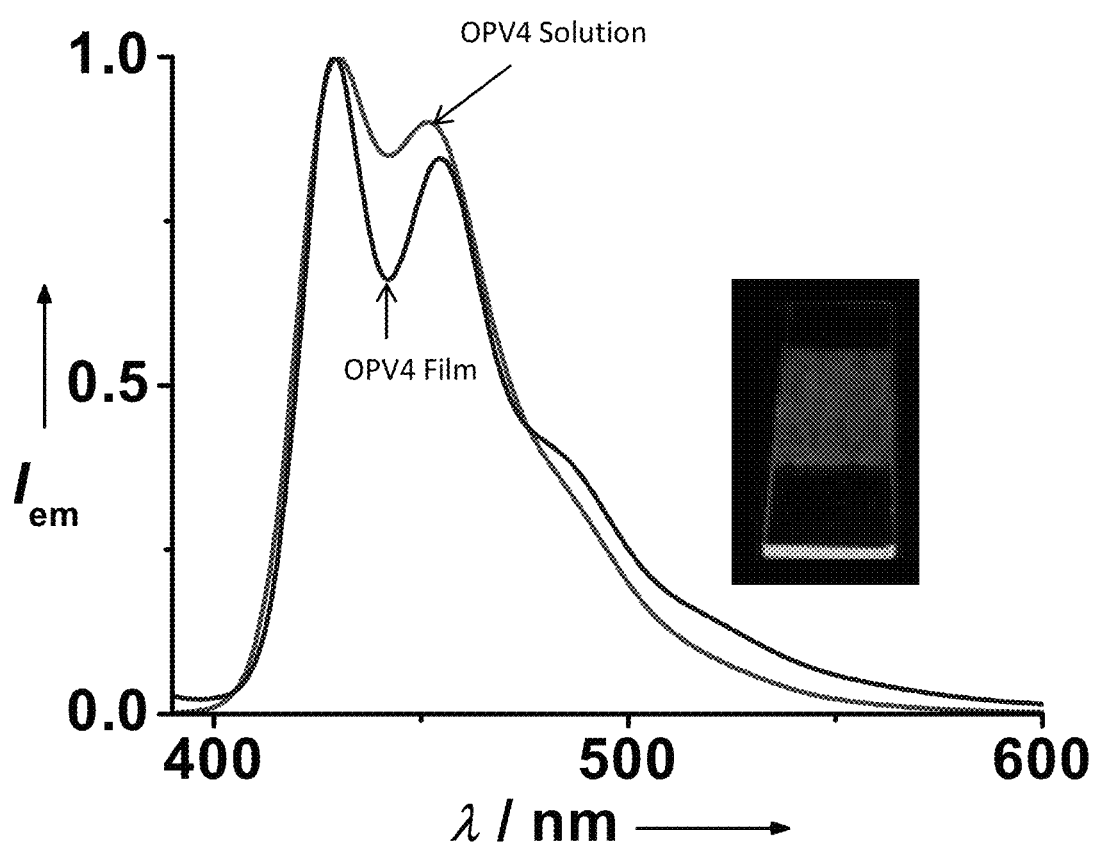
FIG. 59 shows the luminescent state and a luminescent spectrum of OPV4 according to Example 6.

FIG. 59 shows the luminescent state and a luminescent spectrum of OPV4 according to Example 6.

OPV4 Solution and the OPV4 Film were found to be a blue luminescent bodies which are excited at an excitation wavelength (365 nm) to exhibit maximum emission peak wavelengths of 430 nm and 429 nm, respectively. The inserted figure shows the luminescent state of OPV4 Film, and a blue luminescence was confirmed. Similarly to OPV2 to 3, the maximum emission peak wavelength and the emission intensity exhibited no substantial difference between OPV4 Solution and OPV4 Film, but the emission intensity of the second emission peak indicated that OPV4 Film had an emission intensity which was reduced when compared with that of OPV4 Solution. Similarly to OPV2 to 3, this may be due to the difference in the environment where the OPV Core is placed.

Figure 60:
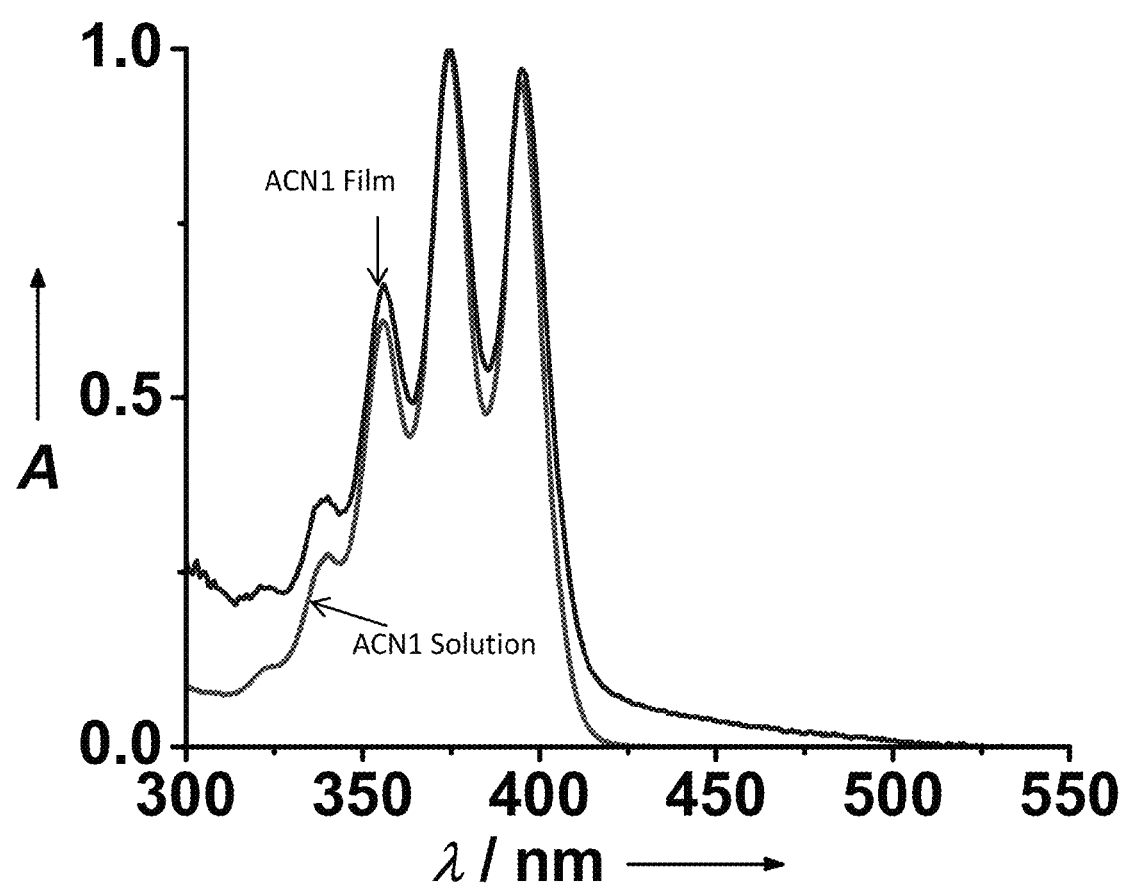
FIG. 60 shows an absorption spectrum of ACN1 according to Example 7.

FIG. 60 shows an absorption spectrum of ACN1 according to Example 7.

ACN1 Solution (ACN1 dissolved in dichloromethane ($5 \times 10^{-5}$M) to form a solution, hereinafter referred to as ACN1 Solution) absorption spectrum and ACN1 spin coat film (ACN1 Solution spin-coated onto a quartz substrate to form a film, hereinafter referred to as ACN1 Film) absorption spectrum both exhibited a similar state. The ACN1 Solution and ACN1 Film absorption spectra exhibited maximum absorption wavelengths ($\lambda_{max}$) which were both 375 nm. The maximum absorption wavelength of ACN1 Solution and that of ACN1 Film had no shift between them. Here again, it is indicated that the molecule in ACN1 Film and the molecule in ACN1 Solution were both present in a single molecule dispersion state.

Figure 61:
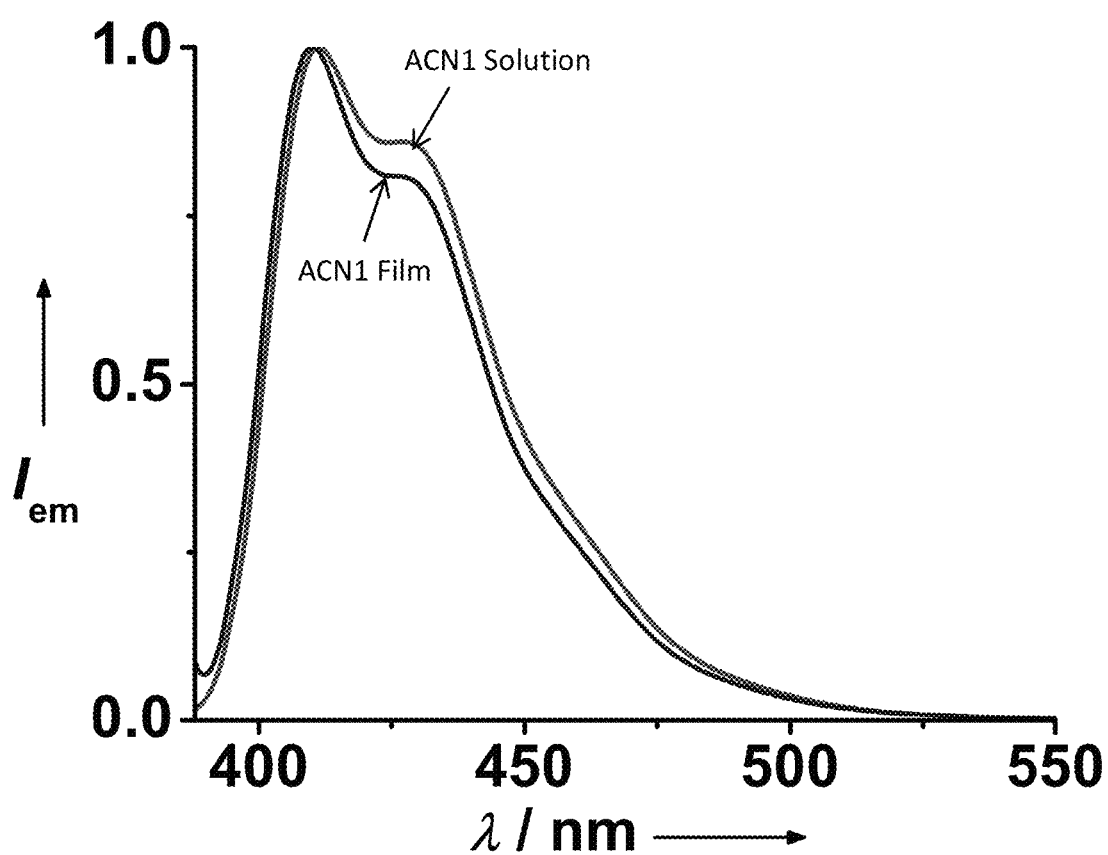
FIG. 61 shows a luminescent spectrum of ACN1 according to Example 7.

FIG. 61 shows a luminescent spectrum of ACN1 according to Example 7.

ACN1 Solution and ACN1 Film were found to be blue luminescent bodies which were excited at an excitation wavelength (375 nm) to exhibit maximum emission peak wavelength 411 nm and 410 nm, respectively.

Figure 62:
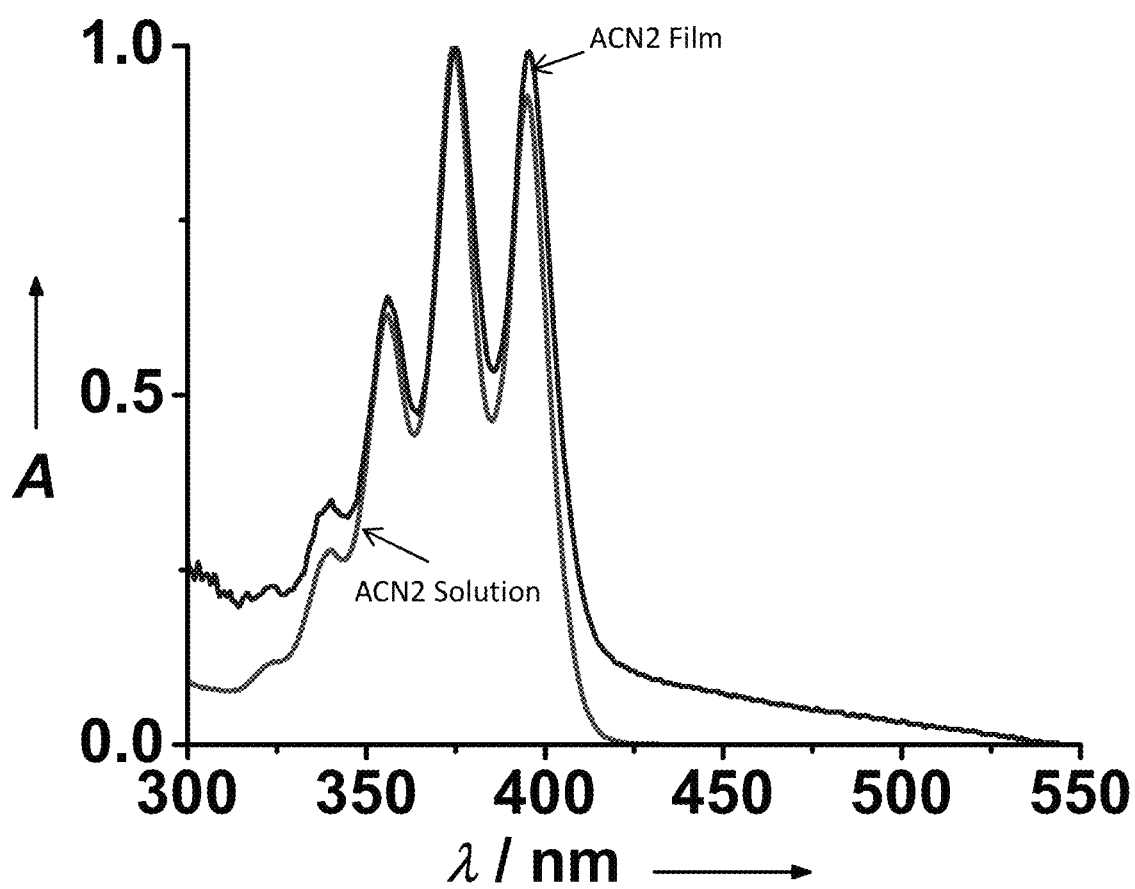
FIG. 62 shows an absorption spectrum of ACN2 according to Example 8.

FIG. 62 shows an absorption spectrum of ACN2 according to Example 8.

ACN2 Solution (ACN2 dissolved in dichloromethane ($5 \times 10^{-5}$M) to form a solution, hereinafter referred to as ACN2 Solution) absorption spectrum and ACN2 spin coat film (ACN2 Solution spin-coated onto a quartz substrate to form a film, hereinafter referred to as ACN2 Film) absorption spectrum both exhibited a similar state. The ACN2 Solution and ACN2 Film absorption spectra exhibited maximum absorption wavelengths ($\lambda_{max}$) which were both 375 nm. The maximum absorption wavelength of ACN2 Solution and that of ACN2 Film had no shift between them. Here again, it is indicated that the molecule in ACN2 Film and the molecule in ACN2 Solution were both present in a single molecule dispersion state.

Figure 63:
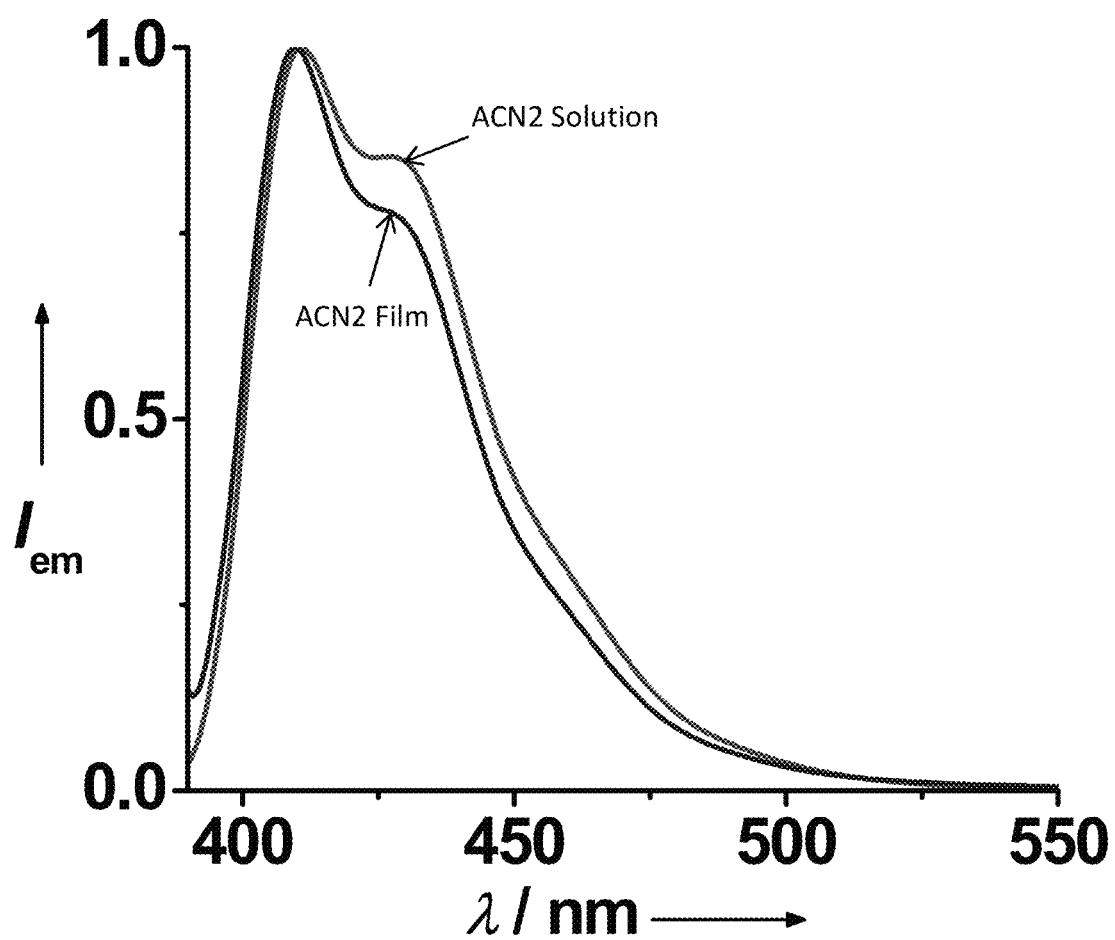
FIG. 63 shows a luminescent spectrum of ACN2 according to Example 8.

FIG. 63 shows a luminescent spectrum of ACN2 according to Example 8.

ACN2 Solution and ACN2 Film were found to be blue luminescent bodies which were excited at an excitation wavelength (375 nm) to exhibit maximum emission peak wavelength 410 nm and 409 nm, respectively.

Figure 64:
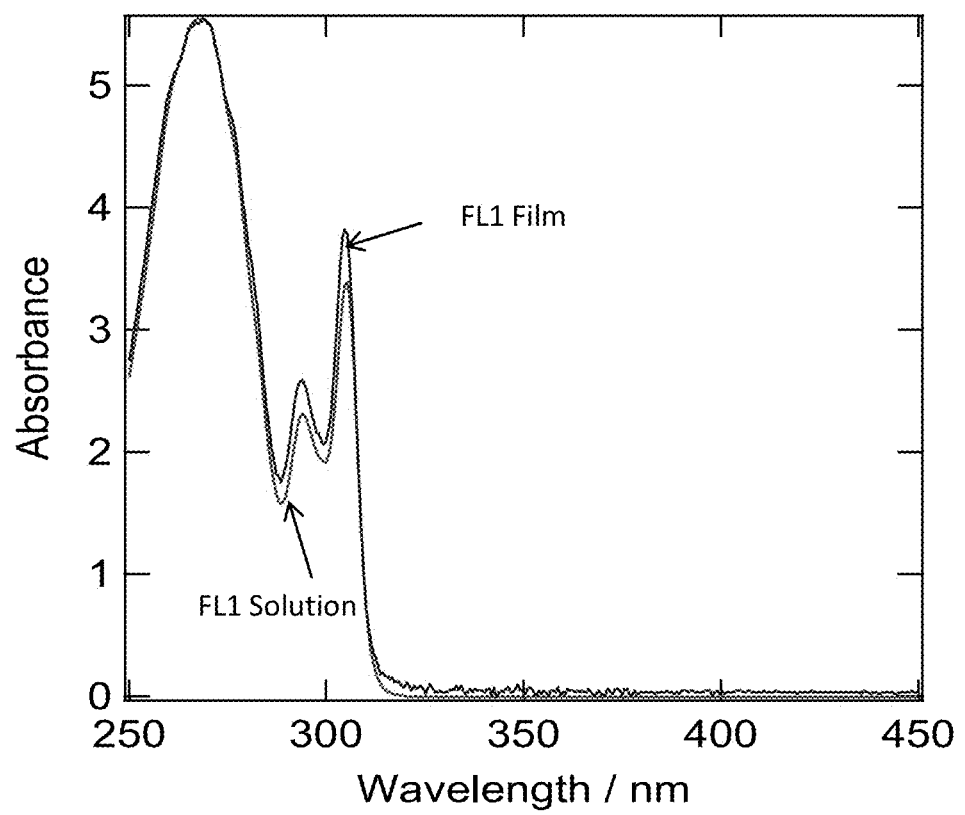
FIG. 64 shows an absorption spectrum of FL1 according to Example 9.

FIG. 64 shows an absorption spectrum of FL1 according to Example 9.

FL1 Solution (FL1 dissolved in dichloromethane ($5 \times 10^{-5}$M) to form a solution, hereinafter referred to as FL1 Solution) absorption spectrum and FL1 spin coat film (FL1 Solution spin-coated onto a quartz substrate to form a film, hereinafter referred to as FL1 Film) absorption spectrum both exhibited similar state and were in a satisfactory agreement. It is indicated that the molecule in the FL1 Film and the molecule in the FL1 Solution were both present in a single molecule dispersion state.

Figure 65:
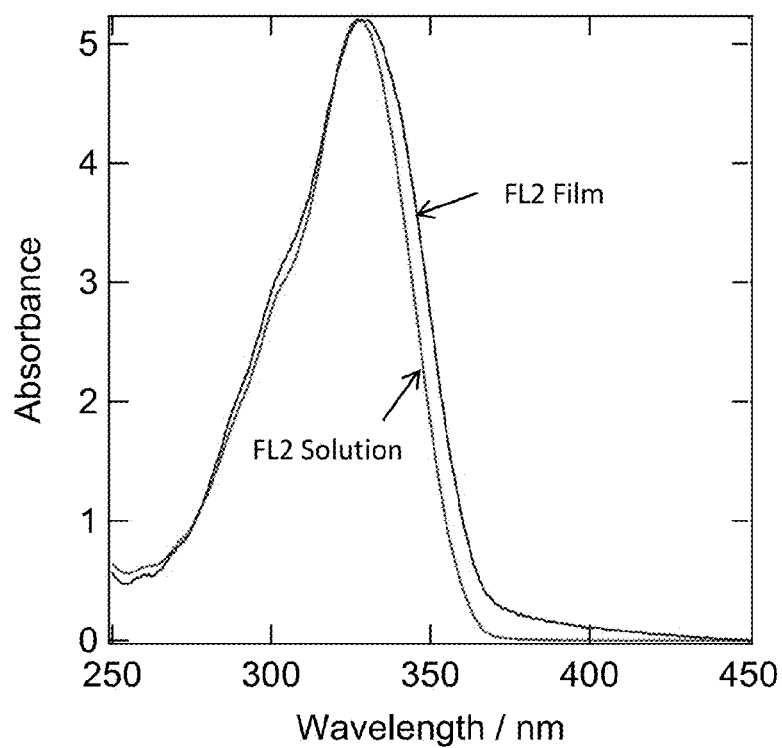
FIG. 65 shows the absorption spectrum and the luminescent state of FL2 according to Example 10.
Figure 65:
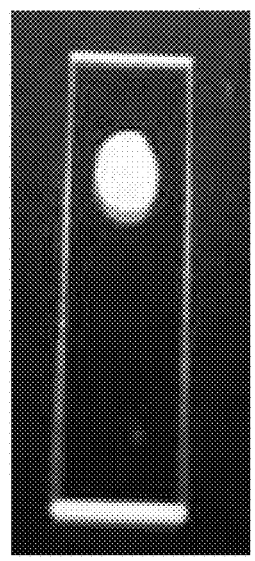

FIG. 65 shows the absorption spectrum and the luminescent state of FL2 according to Example 10.

FL2 Solution (FL2 dissolved in dichloromethane ($5 \times 10^{-5}$M) to form a solution, hereinafter referred to as FL2 Solution) absorption spectrum and FL2 spin coat film (FL2 Solution spin-coated onto a quartz substrate to form a film, hereinafter referred to as FL2 Film) absorption spectrum both exhibited similar state and were in a satisfactory agreement. It is indicated that the molecule in FL2 Film and the molecule in the FL2 Solution were both present in a single molecule dispersion state. Also, with regard to the luminescent state, when FL2 Film was excited at the excitation wavelength (365 nm), FL2 Film exhibited a pale blue luminescence.

Figure 66:
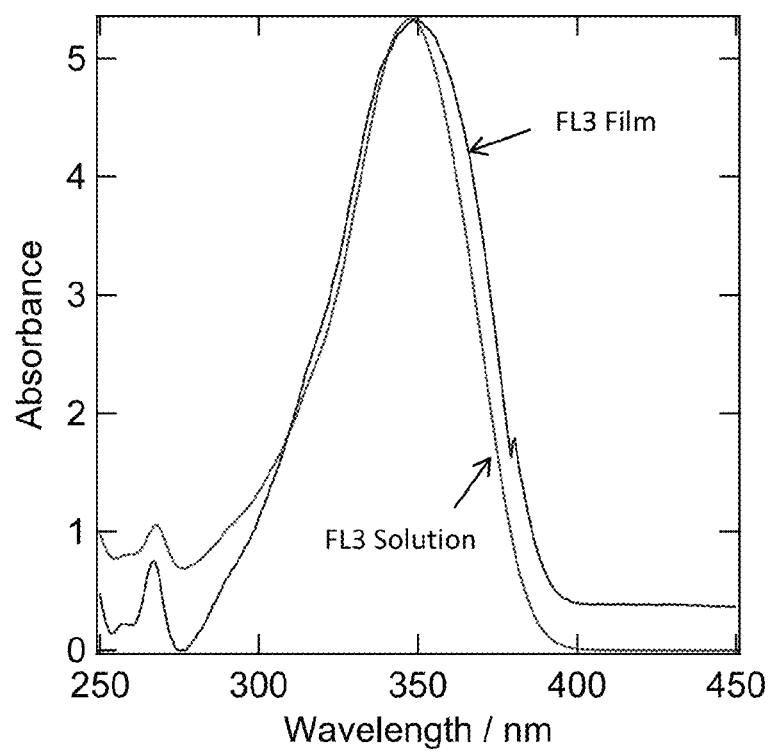
FIG. 66 shows the absorption spectrum and the luminescent state of FL3 according to Example 11.
Figure 66:
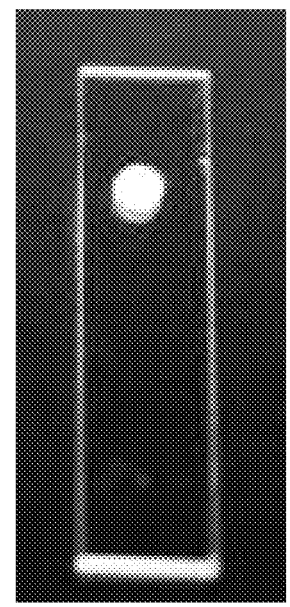

FIG. 66 shows the absorption spectrum and the luminescent state of FL3 according to Example 11.

FL3 Solution (FL3 dissolved in dichloromethane ($5 \times 10^{-5}$M) to form a solution, hereinafter referred to as FL3 Solution) absorption spectrum and FL3 spin coat film (FL3 Solution spin-coated onto a quartz substrate to form a film, hereinafter referred to as FL3 Film) absorption spectrum both exhibited similar state and were in a satisfactory agreement. It is indicated that the molecule in FL3 Film and the molecule in the FL3 Solution were both present in a single molecule dispersion state. Also, with regard to the luminescent state, when FL3 Film was excited at the excitation wavelength (365 nm) similarly to FL2, FL3 Film exhibited a pale blue luminescence.

As discussed above, it was confirmed, according to FIG. 46 to FIG. 66, that the ambient temperature liquid-form organic material of the present invention has a luminescent property, and can be utilized as a luminescent material. The ambient temperature liquid-form organic material of the present invention was found to be able to obtain a desired luminescent property depending on the selection of the π-conjugated molecule. Also based on each absorption spectrum, it was confirmed that the ambient temperature liquid-form organic material of the present invention is a material which does not allow the π-conjugated molecule to undergo aggregation (J-association). Accordingly, it is suggested that when using the ambient temperature liquid-form organic material of the present invention in a laser medium, a highly efficient laser oscillation can be accomplished without using any solvent such as a transparent polymer matrix for suppressing a reduction in the gain due to the aggregation of π-conjugated molecule.

Figure 67:
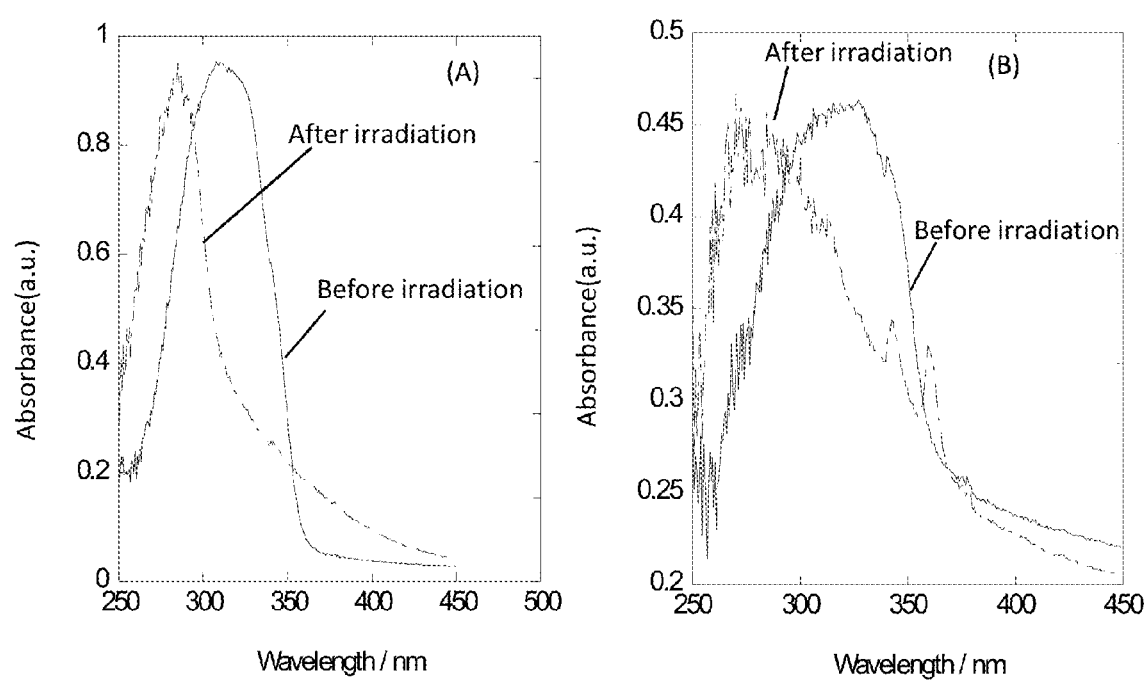
FIG. 67 shows an absorption spectrum of STLB according to Example 13.

FIG. 67 shows an absorption spectrum of STLB according to Example 13.

FIG. 67(A) is the absorption spectrum before and after the ultraviolet light (wavelength 365 nm) irradiation of STLB Solution (SLTB dissolved in chloroform ($1 \times 10^{-4}$M) to form a solution, hereinafter referred to as STLB Solution), and FIG. 67(B) is the absorption spectrum before and after the ultraviolet light irradiation of STLB spin coat film (STLB Solution spin-coated onto a quartz substrate to form a film, hereinafter referred to as STLB Film).

According to FIG. 67(A), STLB Solution exhibited, upon the ultraviolet light irradiation, an absorption spectrum which was shifted to the side of the shorter wavelength. This is because that a trans-cis photoisomerization served to change the molecular transition moment. Similarly, according to FIG. 67(B), SLTB Film also exhibited, upon the ultraviolet light irradiation, an absorption spectrum which was shifted to the side of the shorter wavelength. Also, the maximum absorption wavelengths before and after the ultraviolet light irradiation of STLB Solution and STLB Film were substantially the same. Accordingly, it is indicated that the molecule in STLB Film and the molecule in STLB Solution were both present in a single molecule dispersion state.

SLTB Solution and SLTB Film were both confirmed to be photoisomerized from trans to cis upon the ultraviolet light irradiation. It was also confirmed that the isomerization reverse reaction requires a photosensitizer and the photoisomerization from cis to trans did not occur readily.

FIG. 68 shows an absorption spectrum of AZO according to Example 14.

FIG. 68(A) is the absorption spectrum before and after the ultraviolet light (wavelength 365 nm) irradiation of AZO Solution (AZO dissolved in chloroform ($1 \times 10^{-4}$M) to form a solution, hereinafter referred to as AZO Solution), and FIG. 68(B) is the absorption spectrum before and after the ultraviolet light irradiation of AZO spin coat film (AZO Solution spin-coated onto a quartz substrate to form a film, hereinafter referred to as AZO Film).

According to FIG. 68(A), AZO Solution exhibited a marked change in the absorbance of the absorption spectrum before and after the ultraviolet light irradiation as well as after the room light irradiation, and the maximum absorption wavelength exhibited a change, such as, before irradiation: 371 nm, after irradiation: 361 nm, after room light irradiation: 369 nm. Thus, the ultraviolet light irradiation allowed the maximum absorption wavelength to shift to the side of the shorter wavelength.

On the other hand, according to FIG. 68(B), AZO Film showed a difference in the absorbance of the absorption spectra before and after the ultraviolet irradiation and after room light irradiation, but its maximum absorption wavelength (before irradiation: 372 nm, after irradiation: 372 nm, after room light irradiation: 372 nm) did not change substantially. The change in the absorbance was a marked reduction both for AZO Solution and AZO Film after the irradiation of the ultraviolet light. This indicates that the trans-cis isomerization leads to a reduced absorption band attributable to the trans form. Also, AZO Solution and AZO Film exhibited the maximum absorption wavelengths which were almost the same, and it is indicated that the molecule in AZO Film and the molecule in AZO Solution were both present in a single molecule dispersion state.

AZO Solution and AZO Film were both confirmed to be photoisomerized from trans to cis upon the ultraviolet light irradiation. Also, unlike to STLB, the isomerization reverse reaction does not need any photosensitizer, and only a room light irradiation allows the cis-to-trans photoisomerization to occur readily.

Table 3 shows the photoconductivity and the refractive index of each sample in Examples 1, 3 to 11 and 13 to 14.

TABLE 3

Photoconductivity and refractive index of Examples 1 to 14

| Example | Sample name | Photoconductivity ($\times 10^{-5}$ cm$^2$/Vs) | Refractive index (nD) |
|---|---|---|---|
| 1 | P1 | 1.50 | — |
| 3 | OPV1 | 1.30 | 1.537 |
| 4 | OPV2 | 1.18 | 1.532 |
| 5 | OPV3 | 0.77 | 1.530 |
| 6 | OPV4 | 1.40 | 1.520 |
| 7 | ACN1 | 0.85 | 1.533 |
| 8 | ACN2 | 1.04 | 1.518 |
| 9 | FL1 | 0.99 | 1.497 |
| 10 | FL2 | 1.06 | 1.522 |
| 11 | FL3 | 1.01 | 1.508 |
| 13 | STLB | — | 1.510 |
| 14 | AZO | — | 1.512 |
| | (2,4,6)F180NC$_{60}$ | 1.59 | — |

According to Table 3, the ambient temperature liquid-form organic material according to the present invention had a photoconductivity which was a small value in the order of about $10^{-5}$ cm$^2$/V. The photoconductivity is known to be an extremely high value when the π-conjugated molecules are stacked effectively. Accordingly, it is indicated that the ambient temperature liquid-form organic material according to the present invention allows the π-conjugated molecule to be dispersed. It was also found that the photoconductivity of the ambient temperature liquid-form organic material according to the present invention was smaller when compared with that of (2,4,6)F180NC$_{60}$.

According to Table 3, the ambient temperature liquid-form organic material according to the present invention had a refractive index which is larger than that of a paraffin oil (1.48), but tended to be close to the value attributable to the oil as the density of the π-conjugated molecule was reduced.

FIG. 69 shows a relationship between an emission peak intensity of P1 according to Example 1 and an amount of (2,4,6)F180NC$_{60}$ added.

According to FIG. 69, it was found that as the amount of (2,4,6)F180NC$_{60}$ was increased the P1 emission peak intensity (at a wavelength of 665 nm) was reduced. This is because that the excitation source served to excite an electron in P1 which underwent a charge transportation to (2,4,6)F180NC$_{60}$, resulting in a quenching of the luminescence of P1. Thus, it is indicated that P1 functions as an electron donor and (2,4,6)F180NC$_{60}$ functions as an electron acceptor, thus being a preferred combination. When P1 is supplemented with (2,4,6)F180NC$_{60}$ in an amount of 1 molar equivalent or more, an efficient charge transportation can be achieved.

Figure 70:
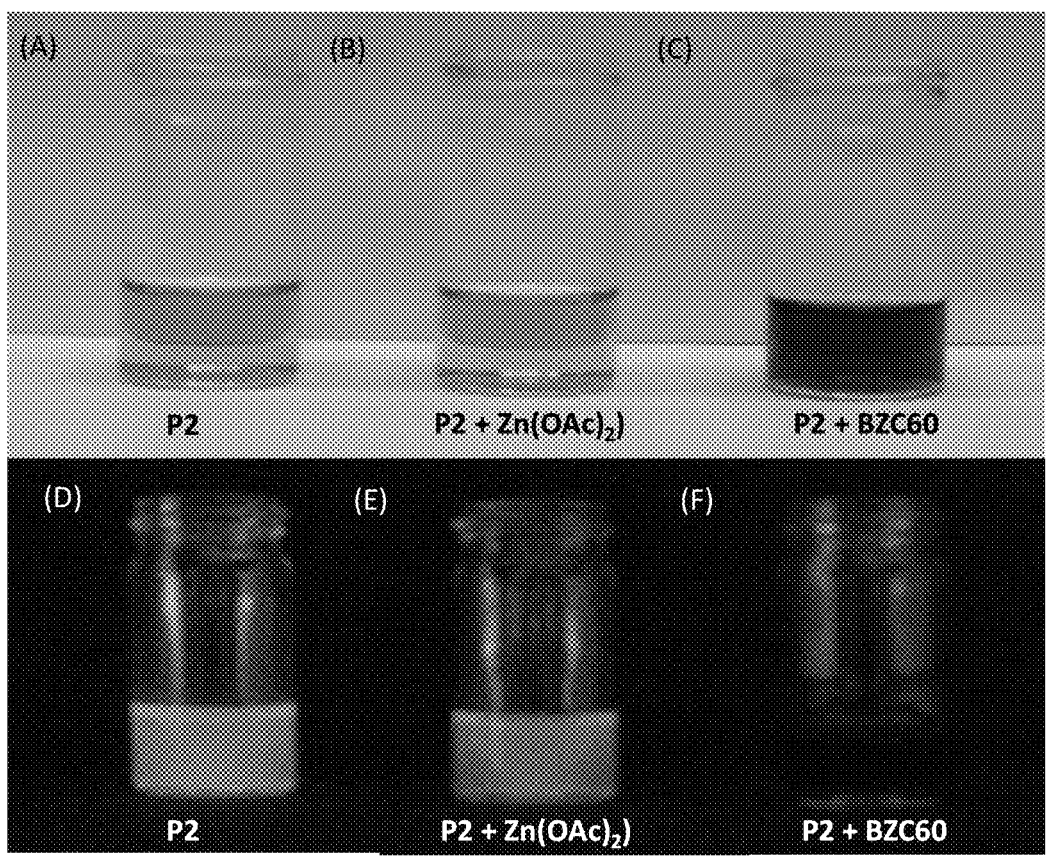
FIG. 70 is an image showing the luminescent state of P2 according to Example 2.

FIG. 70 is an image showing the luminescent state of P2 according to Example 2.

FIGS. 70(A) and (D) show, respectively, the state where P2 Solution is not irradiated with the ultraviolet light (under the visible light) and the state where the ultraviolet light was irradiated. FIGS. 70(B) and (E) show the state where a Zn(OAc)$_2$-supplemented P2 Solution (P2(Zn):Zn-coordinating P2 production) is not irradiated with the ultraviolet light and the state where the ultraviolet light is irradiated. FIGS. 70(C) and (F) show the state where a BZC60-supplemented P2 Solution is not irradiated with the ultraviolet light, and the state where the ultraviolet light is irradiated.

According to FIG. 70(A), P2 was confirmed to be purple under the visible light. According to FIG. 70(D), P2 was confirmed to exhibit a red luminescence upon the ultraviolet light excitation. Thus, it was confirmed that the ambient temperature liquid-form organic material of the present invention has a luminescent property, and can be utilized as a luminescent material.

FIGS. 70(A) and (D) and FIGS. 70(B) and (E) were compared and it was found that the Zn(OAc)$_2$-supplemented P2 Solution (Zn-coordinating P2 production) exhibited a red luminescence more intensely than P2 Solution. This means that the coordination of Zn to porphyrin allowed the luminescent wavelength to be shifted. Thus, it is suggested that by selecting a metal-coordinating molecule as a π-conjugated molecule and allowing a metal to be coordinated, the luminescent property can be controlled.

FIG. 70(D) and FIG. 70(F) were compared, and it was found that the BZC60-supplemented P2 Solution exhibited no luminescence upon the ultraviolet light irradiation. This is because that the excitation source served to excite an electron in P2 which underwent the charge transportation to BZC60, resulting in a quenching of the luminescence of P2. Thus, it is indicated that P2 functions as an electron donor and BZC60 functions as an electron acceptor, thus being a preferred combination.

Figure 71:
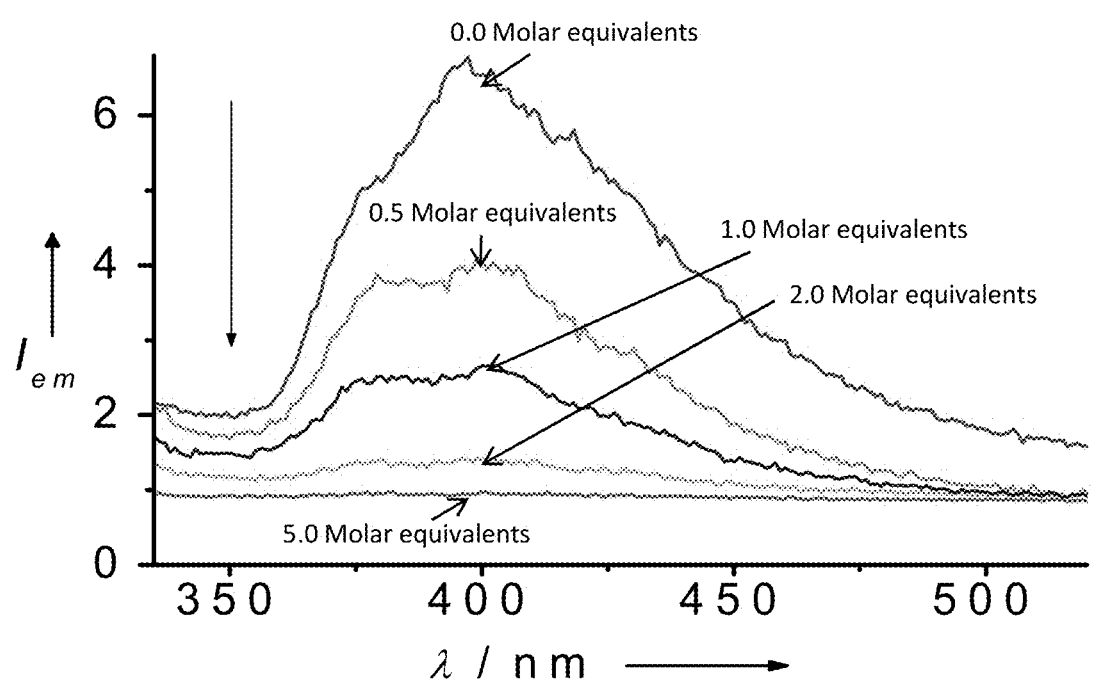
FIG. 71 shows the relationship between the emission peak intensity of OPV1 according to Example 3 and the amount of (2,4,6)F18ONC$_{60}$ added.

FIG. 71 shows the relationship between the emission peak intensity of OPV1 according to Example 3 and the amount of (2,4,6)F180NC$_{60}$ added.

According to FIG. 71, it was found that as the amount of (2,4,6)F180NC$_{60}$ was increased, the OPV1 emission peak intensity (at a wavelength of 397 nm) was reduced. This is because that the excitation source served to excite an electron in OPV1 which underwent a charge transportation to (2,4,6)F180NC$_{60}$, resulting in a quenching of the luminescence of OPV1. Thus, it is indicated that OPV1 functions as an electron donor and (2,4,6)F180NC$_{60}$ functions as an electron acceptor, thus being a preferred combination. When OPV1 is supplemented with (2,4,6)F180NC$_{60}$ in an amount of 2 molar equivalents or more, an efficient charge transportation can be achieved.

Although the figure is not shown, the quenching of the luminescence was confirmed also with a liquid form fullerene represented by the formula shown below when combined with P1, P2, OPV1 to OPV4.

[C.26]

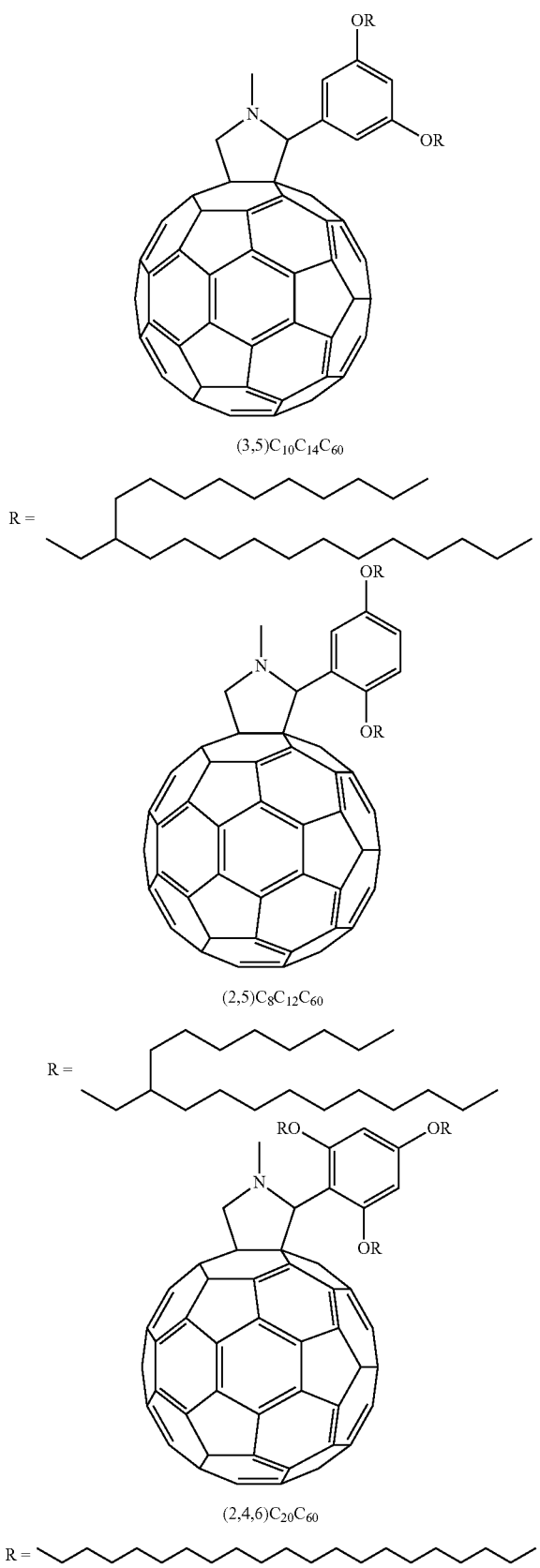

As discussed above, it was confirmed, according to FIG. 69 to FIG. 71, that the ambient temperature liquid-form organic material according to the present invention functions as an electron donor of a photovoltaic device, and can constitute a photovoltaic device when used together with the liquid form fullerene as an electron acceptor. It was also confirmed that a metal coordination to the π-conjugated molecule of the ambient temperature liquid-form organic material according to the present invention allows a further function (for example, control of luminescence) to be imparted.

FIG. 72 shows the luminescent spectrum of a white light luminescence using OPV2 according to Example 4 and the luminescent state.

When a solution of OPV2 and AlQ3 and rubrene mixed in a molar ratio of 1.0:1.65:0.25 was irradiated with an ultraviolet light (wavelength: 365 nm), an ideal white luminescent spectrum was shown and the white luminescence was observed. This had a CIE chromaticity coordinate of x=0.33, y=0.35.

Figure 73:
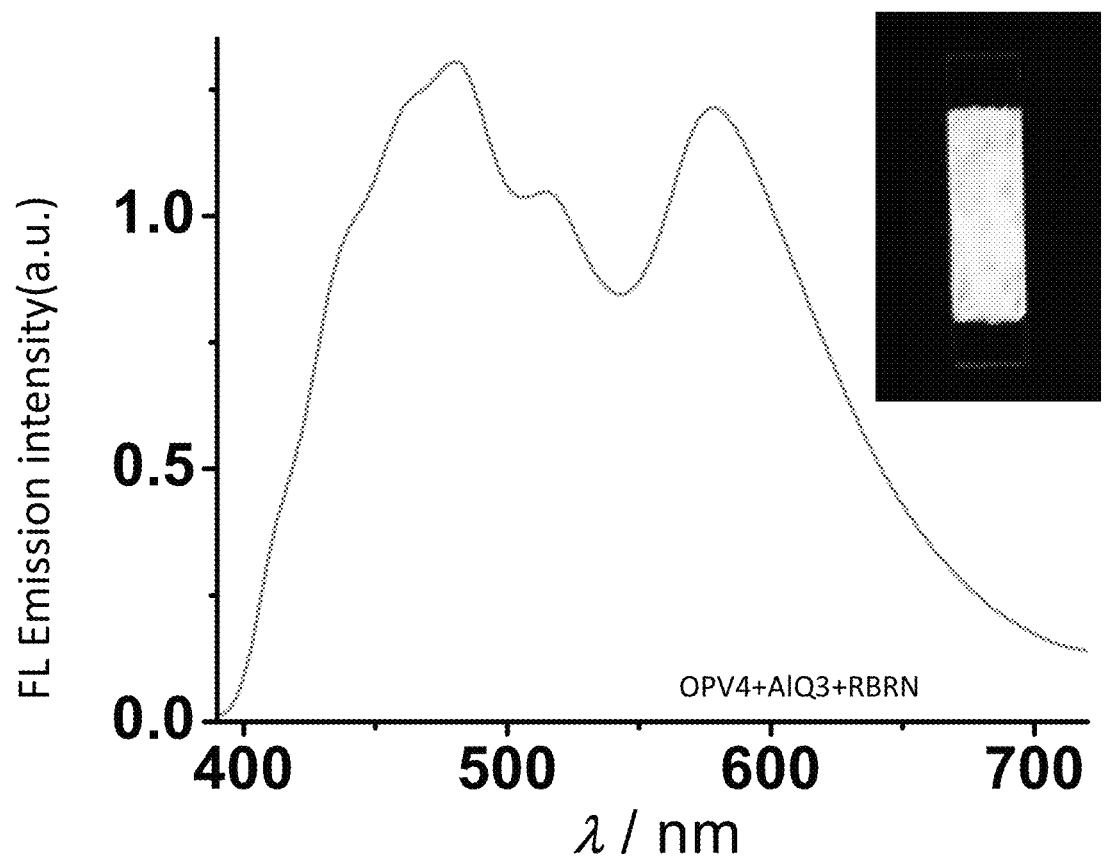
FIG. 73 shows the luminescent spectrum of the white light luminescence using OPV4 according to Example 6 and the luminescent state.

FIG. 73 shows the luminescent spectrum of the white light luminescence using OPV4 according to Example 6 and the luminescent state.

When a solution of OPV4 and AlQ3 and rubrene mixed in a molar ratio of 1.0:1.65:0.24 was irradiated with an ultraviolet light (wavelength: 365 nm), an ideal white luminescent spectrum was shown and the white luminescence was observed. This had a CIE chromaticity coordinate of x=0.33, y=0.34.

Any of OPV2 and OPV4 was able to emit a reddish warm color-based white color or a bluish sharp white color only by changing the mixing ratio. A benefit in a practical use is also realized since AlQ3 and rubrene can readily be in a solid solution form without using a solvent when the ambient temperature liquid-form organic materials OPV2 and OPV4 are used.

As discussed above, it was confirmed, according to FIG. 72 to FIG. 73, that the ambient temperature liquid-form organic material according to the present invention can be used to constitute a white lighting apparatus.

FIG. 74 shows a luminescent state of a white luminescent ink using OPV4 according to Example 6.

FIG. 74(A) shows the luminescent state when using a white luminescent ink in a ball-point pen, and FIG. 74(B) shows the luminescent state when using the white luminescent ink with a brush. According to FIGS. 74(A) and (B), each was confirmed to be white luminescent upon the ultraviolet light irradiation, and can preferably be used as an ink material for a fine character or as a paint for painting a large area.

As discussed above, it was confirmed, according to FIG. 74, that the ambient temperature liquid-form organic material according to the present invention can be an ink material (white luminescent ink material).

INDUSTRIAL APPLICABILITY

The ambient temperature liquid-form organic material according to the present invention consists of a π-conjugated molecule having 2 or more certain side chains directly or via substituents, thereby achieving the ambient temperature liquefaction. The ambient temperature liquid-form organic material according to the present invention can be used in a luminescent material utilizing the luminescent property of the π-conjugated molecule, in an ink material utilizing the pigment (color development) of the π-conjugated molecule, and in a conductive material utilizing the (photo)conductivity of the π-conjugated molecule. Also, the ambient temperature liquid-form organic material according to the present invention can be used as a photovoltaic part of a photovoltaic device to allow for a thin or compact-sized photovoltaic device or a solar battery.

REFERENCE SIGNS LIST

100 Photovoltaic device
110 Transparent electrode
120 Photovoltaic part
130 Counter electrode
140 Electron donor
150 Electron acceptor
160 Electrolyte solution
200 Lighting apparatus
210 Excitation light source
220 Wavelength conversion part
230, 240 Lead wire
250 Fine gold wire
260 Transparent substance
300 Laser device
310 Excitation source
320 Laser medium
330 Excitation light
340 Visible light
400 Color barcode
410, 420, 430, 440, 450, 460 Region

CITATION LIST

Patent Literature

Patent Literature 1: International Publication No. WO2009/113511 pamphlet

The invention claimed is:

1. An ambient temperature liquid-form organic material consisting of a π-conjugated molecule having 2 or more branched alkyl chains, wherein:
the π-conjugated molecule is selected from the group consisting of oligo(p-)phenylene vinylene and stilbene,
each of the 2 or more branched alkyl chains is bound to the π-conjugated molecule directly or via a substituent,
each of the 2 or more branched alkyl chains is independently represented by any one of the following formulae:

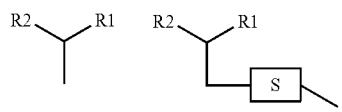

[C.1]

wherein S is a substituent that is at least one selected from the group consisting of phenyl, benzyl, methylene, amido, ester, ether, thioether and urea, and the combination of the R1 and R2 is selected from the group consisting of the following formulae:

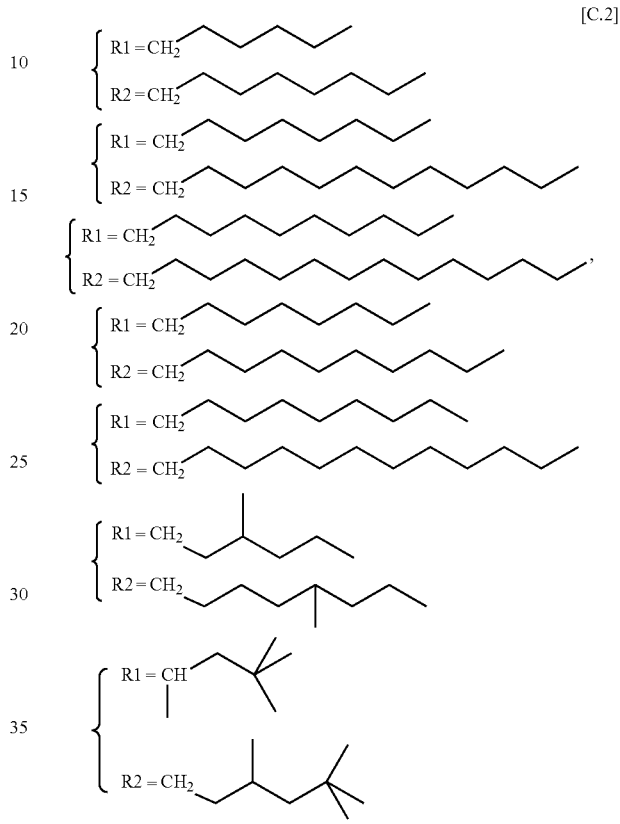

[C.2]

and the 2 or more branched alkyl chains are bound to the π-conjugated molecule in such a manner that the π-π interaction between π-conjugated molecules is inhibited.

2. The ambient temperature liquid-form organic material according to claim 1, wherein the π-conjugated molecule has an absorption in a ultraviolet or visible wavelength region.

3. The ambient temperature liquid-form organic material according to claim 1, wherein the π-conjugated molecule is oligo(p-)phenylene vinylene and represented by any of the following formulae:

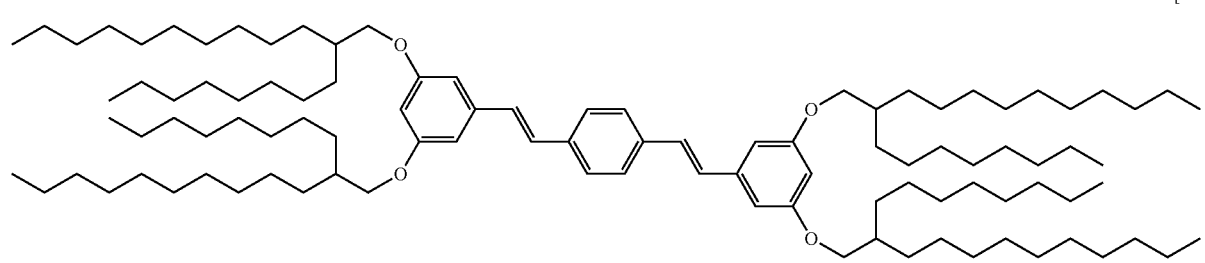

[C.5]

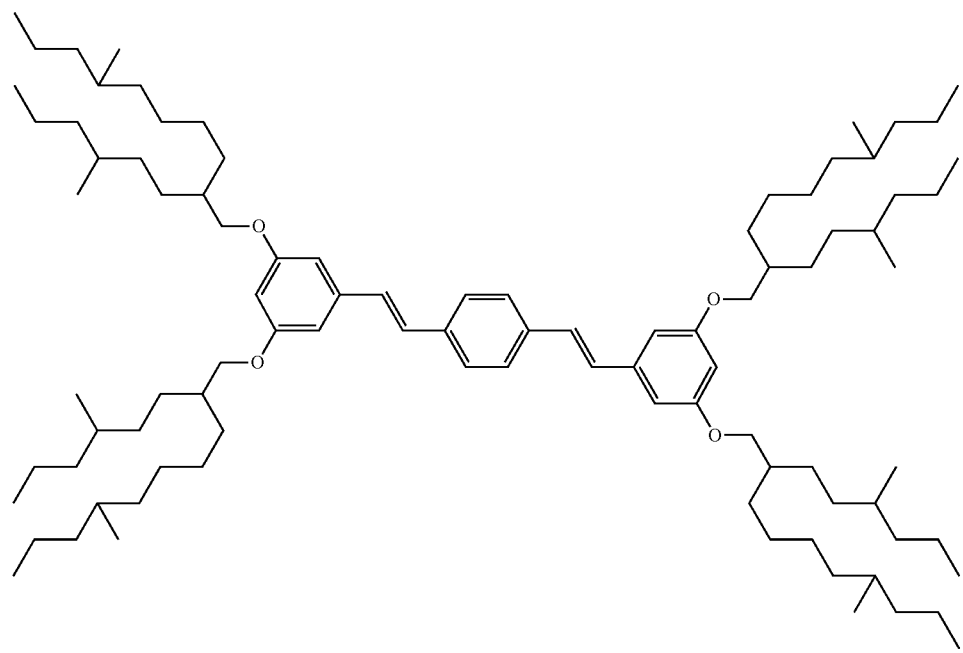
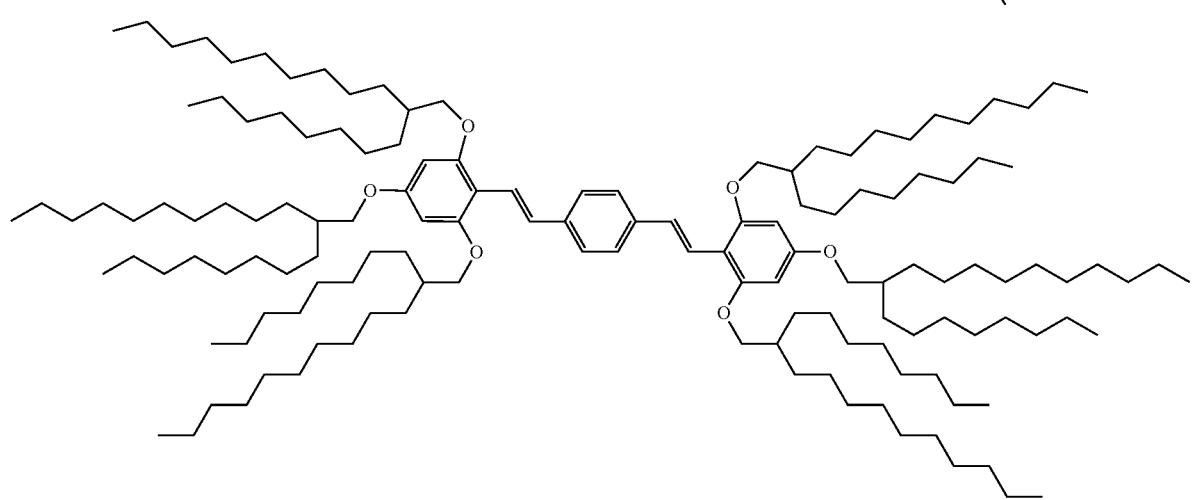
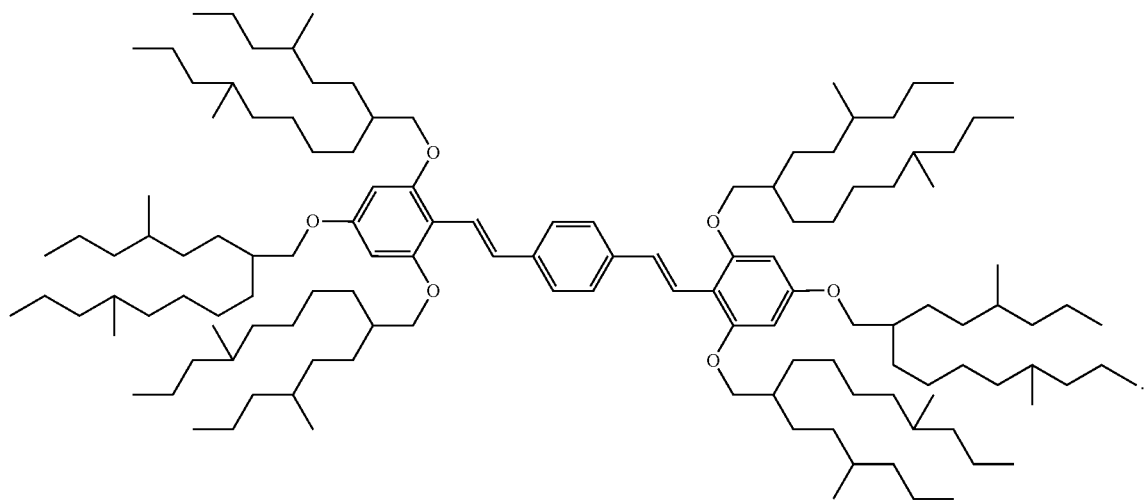 [SMILES: CCCC(C)CCCCC(CCC(C)CCC)COc1cc(OCC(CCCCC(C)CCC)CCC(C)CCC)c(/C=C/c2ccc(/C=C/c3c(OCC(CCCCC(C)CCC)CCC(C)CCC)cc(OCC(CCCCC(C)CCC)CCC(C)CCC)cc3OCC(CCCCC(C)CCC)CCC(C)CCC)cc2)c(OCC(CCCCC(C)CCC)CCC(C)CCC)c1]

4. A luminescent material comprising the ambient temperature liquid-form organic material according to claim 1.

5. An ink material comprising the ambient temperature liquid-form organic material according to claim 1.

6. A photovoltaic device comprising a transparent electrode, a photovoltaic part and a counter electrode,
wherein the photovoltaic part includes the ambient temperature liquid-form organic material according to claim 1.

7. The photovoltaic device according to claim 6,
wherein the photovoltaic part comprises an electron donor and an electron acceptor, and
a solvent for the electron donor and electron acceptor is the ambient temperature liquid-form organic material.

8. The photovoltaic device according to claim 6,
wherein the photovoltaic part comprises an electron donor and an electron acceptor,
the electron donor is the ambient temperature liquid-form organic material, and
the electron acceptor is an ambient temperature liquid-form fullerene.

* * * * *